United States Patent
Barlow et al.

(10) Patent No.: US 9,993,605 B2
(45) Date of Patent: Jun. 12, 2018

(54) PAP SYSTEM

(75) Inventors: Adam Francis Barlow, Sydney (AU); Michael Stephen Cheung, New York, NY (US); Thomas M. Dair, New York, NY (US); Aaron Samuel Davidson, Sydney (AU); Justin John Formica, Sydney (AU); Samuel Aziz Mebasser, Chatsworth, CA (US); Michael Murillo, New York, NY (US); Andrew Martin Price, Sydney (AU); Jose Ignacio Romagnoli, Sydney (AU); Gerard Michael Rummery, Woodford (AU); Allan Freas Velzy, Burlingame, CA (US)

(73) Assignee: ResMed Limited, Bella Vista (AU)

( * ) Notice: Subject to any disclaimer, the term of this patent is extended or adjusted under 35 U.S.C. 154(b) by 607 days.

(21) Appl. No.: 14/128,053

(22) PCT Filed: Jun. 21, 2012

(86) PCT No.: PCT/AU2012/000720
§ 371 (c)(1),
(2), (4) Date: Dec. 20, 2013

(87) PCT Pub. No.: WO2012/174602
PCT Pub. Date: Dec. 27, 2012

(65) Prior Publication Data
US 2014/0137870 A1 May 22, 2014

Related U.S. Application Data

(60) Provisional application No. 61/457,858, filed on Jun. 21, 2011.

(51) Int. Cl.
*A61M 16/00* (2006.01)
*A61M 16/06* (2006.01)
(Continued)

(52) U.S. Cl.
CPC .... *A61M 16/0051* (2013.01); *A61M 16/0057* (2013.01); *A61M 16/0066* (2013.01);
(Continued)

(58) Field of Classification Search
CPC .......... A61M 16/0051; A61M 16/0666; A61M 16/0875; A61M 16/0605; A61M 16/0057;
(Continued)

(56) References Cited

U.S. PATENT DOCUMENTS 2,999,497 A * 9/1961 Hamilton ................. A62B 9/00
128/204.18
4,671,271 A * 6/1987 Bishop ............... A41D 13/1161
128/206.11
(Continued)

FOREIGN PATENT DOCUMENTS

CN 101396576 4/2009
CN 101460211 6/2009
(Continued)

OTHER PUBLICATIONS

Partial Supplementary European Search Report issued in corresponding EP 12 80 2625.9 dated Nov. 14, 2014.
(Continued)

*Primary Examiner* — Annette Dixon
(74) *Attorney, Agent, or Firm* — Nixon & Vanderhye P.C.

(57) ABSTRACT

A PAP system includes a PAP device to generate a supply of pressurized air, a patient interface adapted to form a seal with the patient's face, air delivery tubing to interconnect the patient interface and the PAP device, and a cover that substantially encloses at least a portion of the PAP device and a portion of the air delivery tubing. The cover allows the PAP device to be carried by and/or supported on the patient's head.

39 Claims, 95 Drawing Sheets

(51) Int. Cl.
*A61M 16/08* (2006.01)
*A61M 16/10* (2006.01)

(52) U.S. Cl.
CPC .......... *A61M 16/024* (2017.08); *A61M 16/06* (2013.01); *A61M 16/0605* (2014.02); *A61M 16/0666* (2013.01); *A61M 16/0683* (2013.01); *A61M 16/08* (2013.01); *A61M 16/0875* (2013.01); *A61M 16/0633* (2014.02); *A61M 16/0816* (2013.01); *A61M 16/0825* (2014.02); *A61M 16/107* (2014.02); *A61M 2205/10* (2013.01); *A61M 2205/15* (2013.01); *A61M 2205/332* (2013.01); *A61M 2205/3375* (2013.01); *A61M 2205/42* (2013.01); *A61M 2205/502* (2013.01); *A61M 2205/52* (2013.01); *A61M 2205/583* (2013.01); *A61M 2205/59* (2013.01); *A61M 2205/75* (2013.01); *A61M 2205/82* (2013.01); *A61M 2205/825* (2013.01); *A61M 2205/8243* (2013.01); *A61M 2209/082* (2013.01); *A61M 2209/088* (2013.01); *A61M 2230/62* (2013.01); *A61M 2230/63* (2013.01)

(58) Field of Classification Search
CPC .............. A61M 16/0066; A61M 16/06; A61M 16/0683; A61M 16/08; A61M 2205/825; A61M 2205/3375; A61M 2205/502; A61M 2205/52; A61M 16/00; A61M 16/0009; A61M 16/0069; A61M 16/0075; A61M 16/0084; A61M 16/0611; A61M 16/0616; A61M 16/0622; A61M 16/0627; A61M 16/0633; A61M 16/0638; A61M 16/0644; A61M 16/0672; A61M 16/0694; A61M 16/0816; A61M 16/0825; A61M 16/0833; A61M 16/0858; A61M 16/101; A61M 16/1015; A61M 16/1045; A61M 16/1055; A61M 16/107; A61M 16/1075; A61M 16/109; A61M 16/142; A61M 16/16; A61M 16/161; A61M 16/162; A61M 16/20; A61M 16/208; A61M 2016/0021; A61M 2016/0027; A61M 2016/0033; A61M 2016/0036; A61M 2205/02; A61M 2205/0216; A61M 2205/0227; A61M 2205/0238; A61M 2205/273; A61M 2205/3331; A61M 2205/3365; A61M 2205/3368; A61M 2205/3561; A61M 2205/3569; A61M 2205/3584; A61M 2205/3592; A61M 2205/3653; A61M 2205/42; A61M 2205/50; A61M 2205/505; A61M 2205/581; A61M 2205/582; A61M 2205/583; A61M 2205/588; A61M 2205/59; A61M 2205/8206; A61M 2205/8237; A61M 2209/06; A61M 2209/086; A61M 2209/088; A61M 2210/0618; A61M 2210/0625; A61M 2230/432; A61M 2230/435; A61M 2230/50; A61B 5/087; A61B 5/1118; A61B 5/411; A61B 5/415; A61B 5/4815; A61B 5/4818; A61B 5/681; A61B 5/742
USPC ............ 128/207.18, 205.25, 206.24, 200.24, 128/204.18, 204.21, 204.23, 205.24, 128/206.21, 207.11, 207.13
See application file for complete search history.

(56) References Cited

U.S. PATENT DOCUMENTS

| | | | | |
|---|---|---|---|---|
| 5,503,147 | A | * | 4/1996 | Bertheau .............. A62B 18/084 128/201.22 |
| 6,014,971 | A | * | 1/2000 | Danisch .............. A62B 18/045 128/201.25 |
| 6,192,886 | B1 | * | 2/2001 | Rudolph .............. A61M 16/06 128/205.25 |
| 6,250,299 | B1 | * | 6/2001 | Danisch .............. A62B 18/045 128/201.25 |
| 6,279,572 | B1 | * | 8/2001 | Danisch .............. A62B 18/045 128/201.25 |
| 8,327,851 | B2 | * | 12/2012 | Connor ................. A61M 16/06 128/201.23 |
| 8,667,962 | B2 | * | 3/2014 | Kenyon ............ A61M 16/0057 128/200.24 |
| 9,687,619 | B2 | * | 6/2017 | Stuebiger .......... A61M 16/0683 |
| 2002/0043264 | A1 | * | 4/2002 | Wickham .............. A61M 16/00 128/204.18 |
| 2004/0087878 | A1 | | 5/2004 | Krausman et al. |
| 2005/0103342 | A1 | | 5/2005 | Jorczak et al. |
| 2006/0096596 | A1 | | 5/2006 | Occhialini et al. |
| 2006/0102184 | A1 | * | 5/2006 | Kullik ................... A61M 16/06 128/206.24 |
| 2006/0212273 | A1 | | 9/2006 | Krausman et al. |
| 2006/0213516 | A1 | * | 9/2006 | Hoffman .............. A61M 16/00 128/204.18 |
| 2006/0237013 | A1 | | 10/2006 | Kwok |
| 2007/0215161 | A1 | * | 9/2007 | Frater ................... A61M 16/06 128/206.24 |
| 2007/0277827 | A1 | | 12/2007 | Bordewick et al. |
| 2007/0277828 | A1 | | 12/2007 | Ho et al. |
| 2008/0047560 | A1 | * | 2/2008 | Veliss ................... A61M 16/06 128/206.24 |
| 2008/0060649 | A1 | * | 3/2008 | Veliss ................... A61M 16/06 128/205.25 |
| 2009/0078259 | A1 | * | 3/2009 | Kooij ................ A61M 16/0875 128/205.25 |
| 2009/0320842 | A1 | | 12/2009 | Doherty et al. |
| 2010/0170513 | A1 | * | 7/2010 | Bowditch .............. A61M 16/00 128/204.23 |
| 2010/0224276 | A1 | | 9/2010 | Forrester et al. |
| 2012/0152255 | A1 | * | 6/2012 | Barlow ............ A61M 16/0066 128/205.25 |

FOREIGN PATENT DOCUMENTS

| | | |
|---|---|---|
| CN | 101466429 | 6/2009 |
| CN | 101502690 | 8/2009 |
| CN | 101516427 | 8/2009 |
| CN | 101951984 | 1/2011 |
| CN | 101977656 | 2/2011 |
| CN | 202335364 | 7/2012 |
| EP | 2 039 386 | 3/2009 |
| EP | 2 085 106 | 8/2009 |
| GB | 2491897 | 12/2012 |
| JP | H07-503164 | 4/1995 |
| JP | 2009-072596 | 4/2009 |
| JP | 2009-523055 | 6/2009 |
| JP | 2009-178557 | 8/2009 |
| JP | 2009-544371 | 12/2009 |
| JP | 2009-544372 | 12/2009 |
| WO | WO 2007/068044 | 6/2007 |
| WO | WO 2008/011682 A1 | 1/2008 |
| WO | PCT/AU2010/000684 | 6/2010 |
| WO | PCT/AU2010/001031 | 8/2010 |
| WO | PCT/AU2010/001106 | 8/2010 |
| WO | WO 2011/051838 | 5/2011 |
| WO | PCT/AU2012/000720 | 6/2012 |

OTHER PUBLICATIONS

Patent Examination Report No. 2 issued in corresponding Australian Appln. No. 2012272510, dated Jan. 20, 2015.

(56) References Cited

OTHER PUBLICATIONS

Notice of Acceptance issued in corresponding Australian Appln. No. 2012272510 dated Apr. 17, 2015.
Extended European Search Reported issued in corresponding European Appln. No. 12 80 2625.9 dated Apr. 29, 2015.
First Office Action issued in corresponding Chinese Appln. No. 201280031048.8 dated May 27, 2015 with English translation thereof.
Patent Examination Report No. 1 issued in corresponding Australian Appln. No. 2012272510, dated Jul. 17, 2014.
First Examination Report issued in New Zealand Appln. No. 618892, dated Jul. 24, 2014.
First Examination Report issued in corresponding Application No. 709784 dated Jul. 30, 2015.
First Office Action issued in corresponding Japanese Patent Application No. 2014-516134 dated Mar. 7, 2016, with English translation thereof.
Communication pursuant to Article 94(3) EPC issued in corresponding European Patent Application No. 12 802 625.9 dated Mar. 22, 2016.
Examination Report dated Jan. 20, 2017 issued in New Zealand Application No. 727624 (6 pages).
U.S. Appl. No. 13/321,981, filed Nov. 2011, Barlow et al., 2012/0067349, Mar. 2012.
International Search Report issued in a PCT Application No. PCT/AU2010/000720, dated Sep. 12, 2012.
Notice of Reasons for Rejection dated Nov. 7, 2016 issued in Japanese Application No. 2014-516134 with English translation (9 pages).
Notice of Allowance dated Jul. 24, 2017 issued in Japanese Application No. 2014-516134 with English translation (6 pages).
Extended European Search Report dated Mar. 29, 2018 issued in European Application No. 17182844.5 (10 pages).

\* cited by examiner

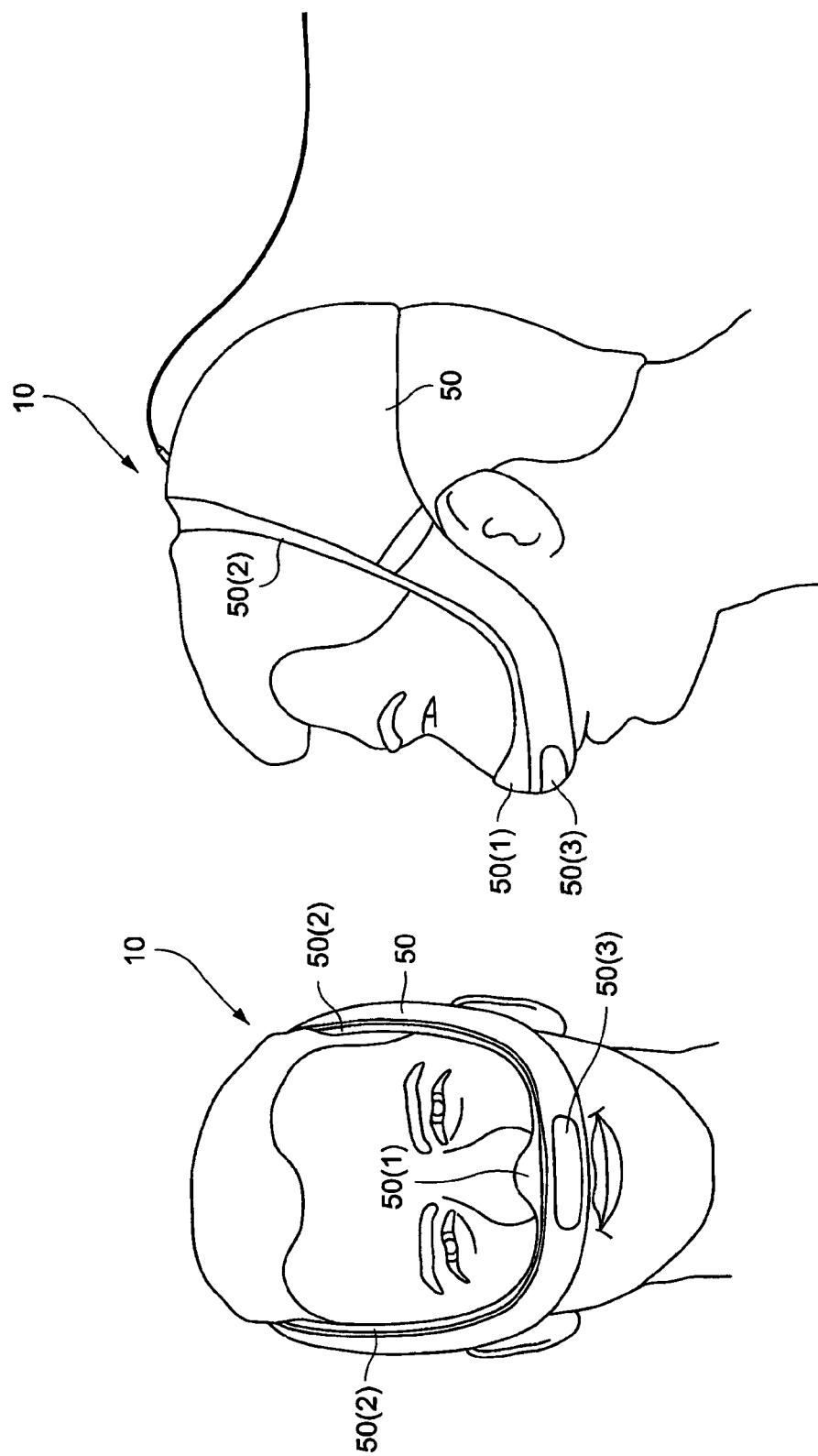

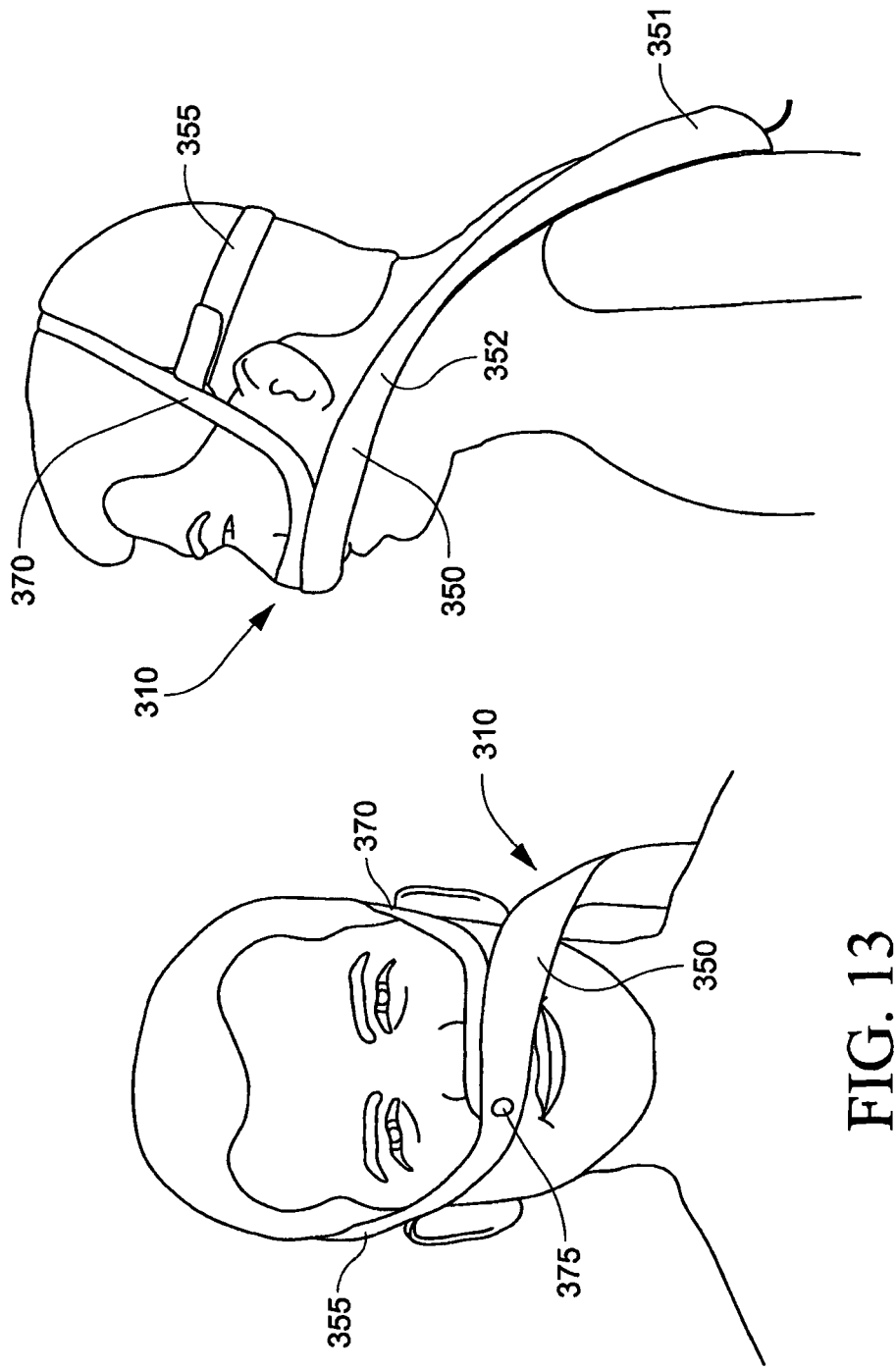

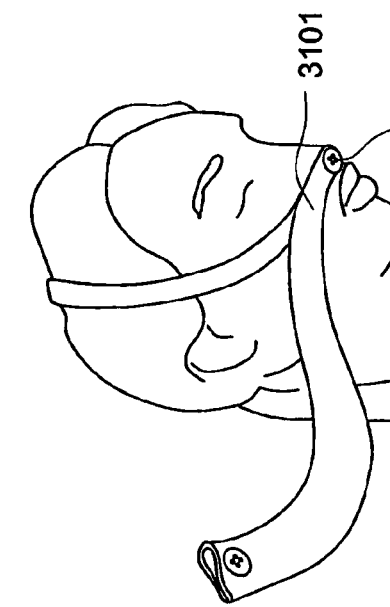
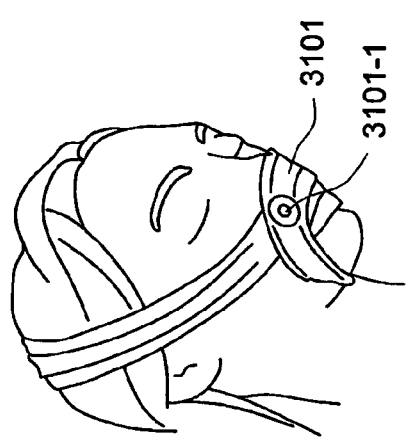
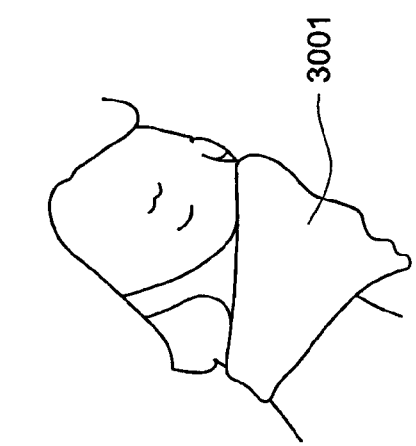
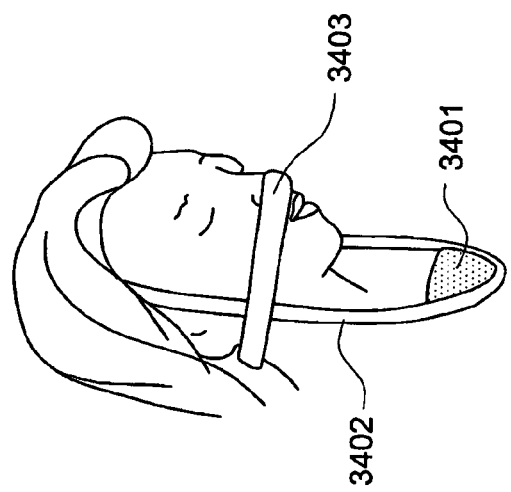
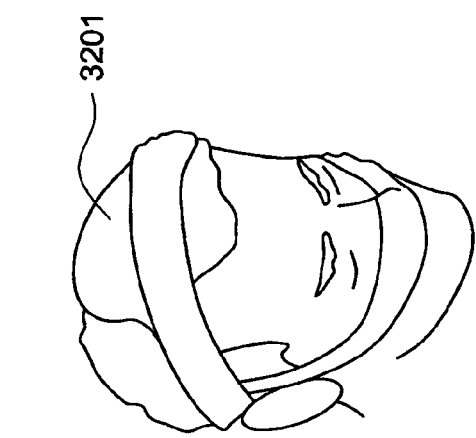

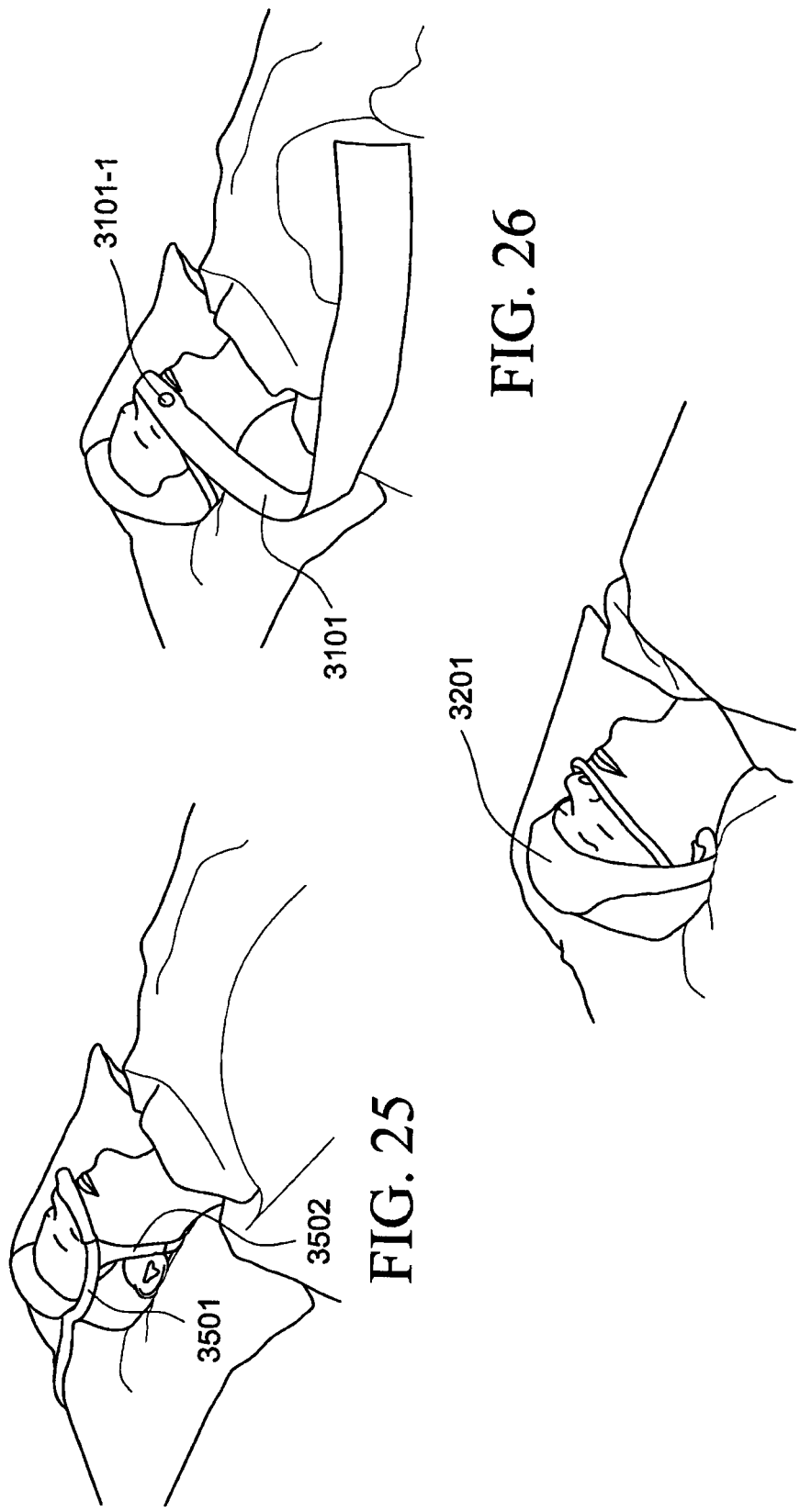

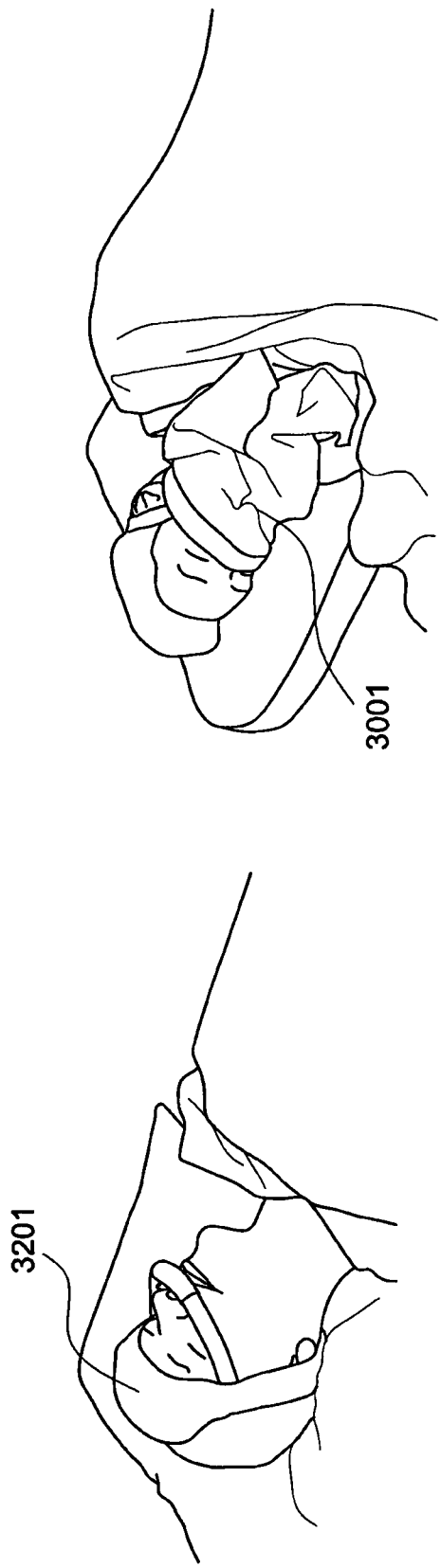
FIG. 29
FIG. 28
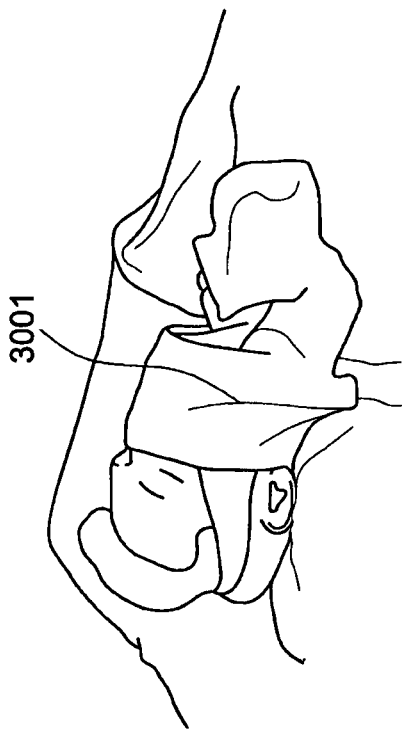
FIG. 30

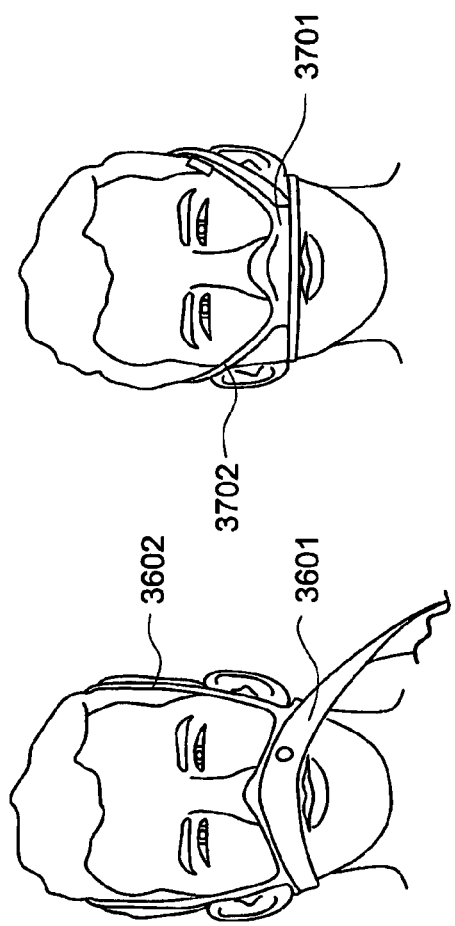
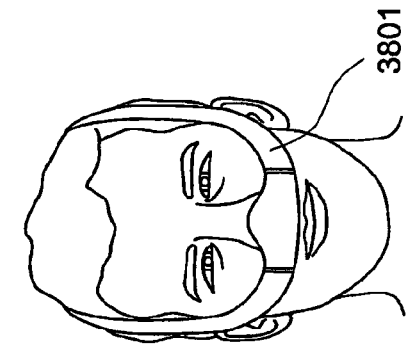
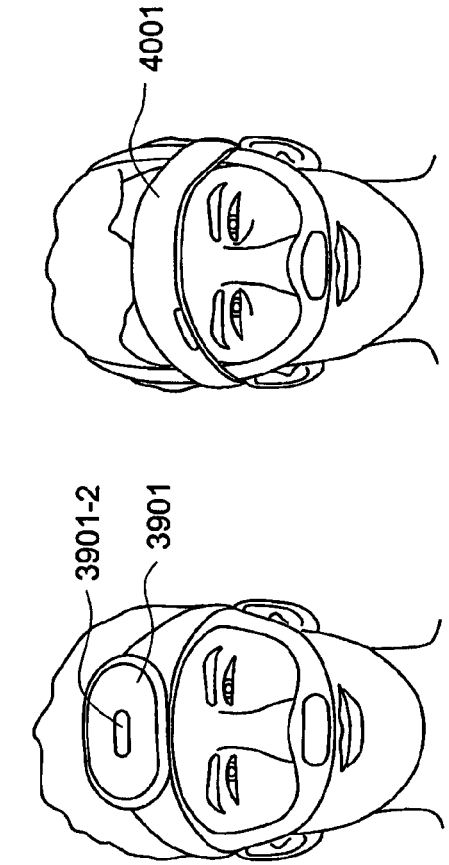
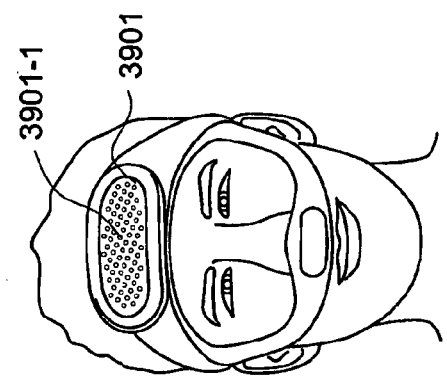

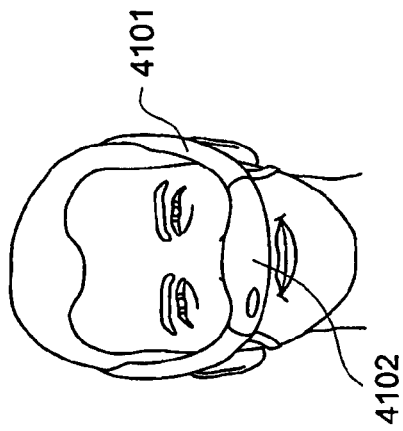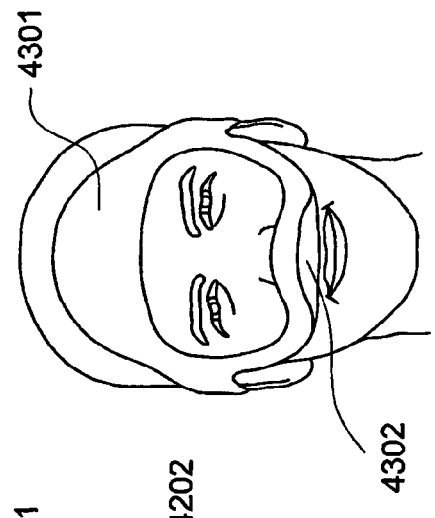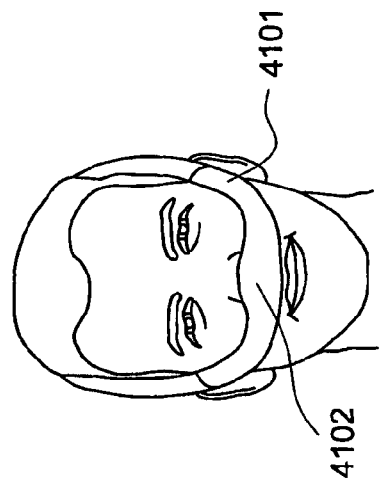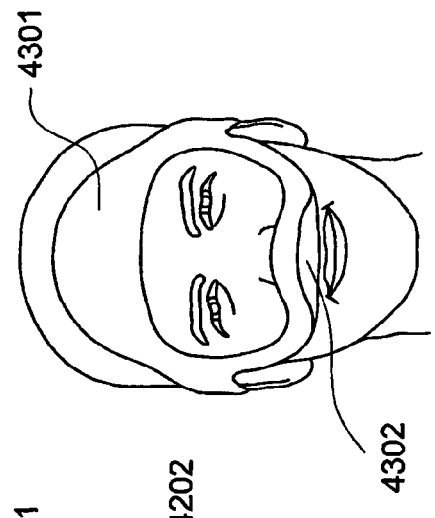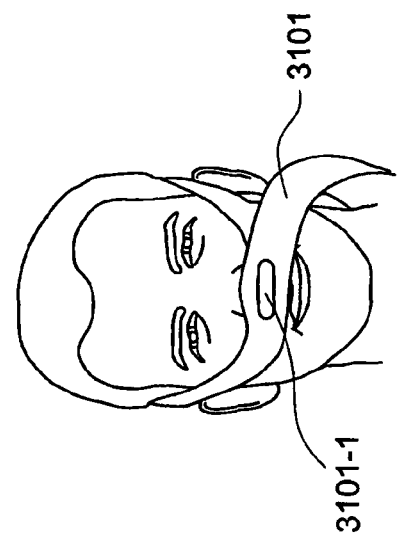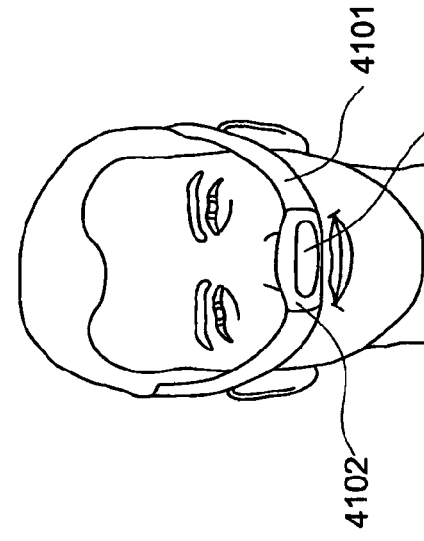

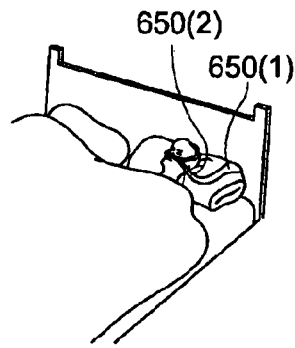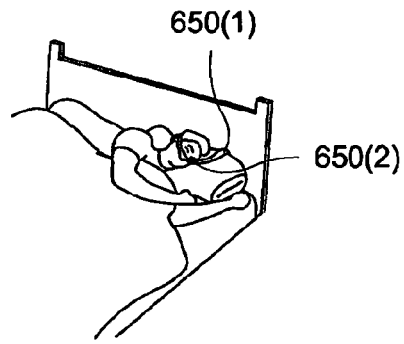
FIG. 46  FIG. 47
FIG. 48
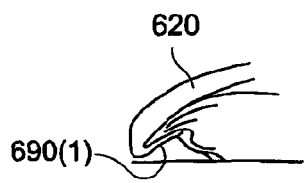 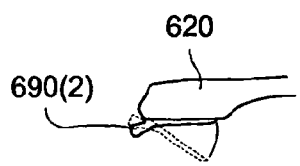 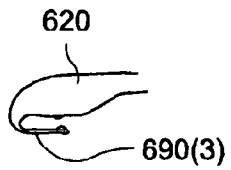
FIG. 49-1  FIG. 49-2  FIG. 49-3
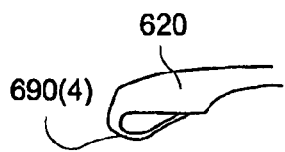  
FIG. 49-4  FIG. 49-5  FIG. 49-6

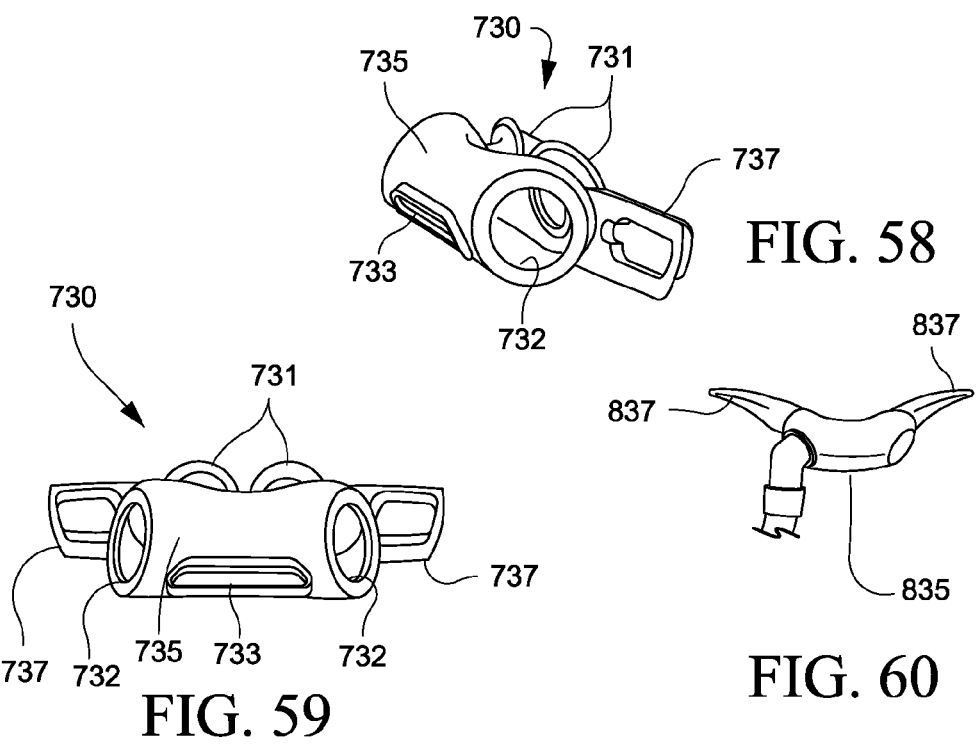
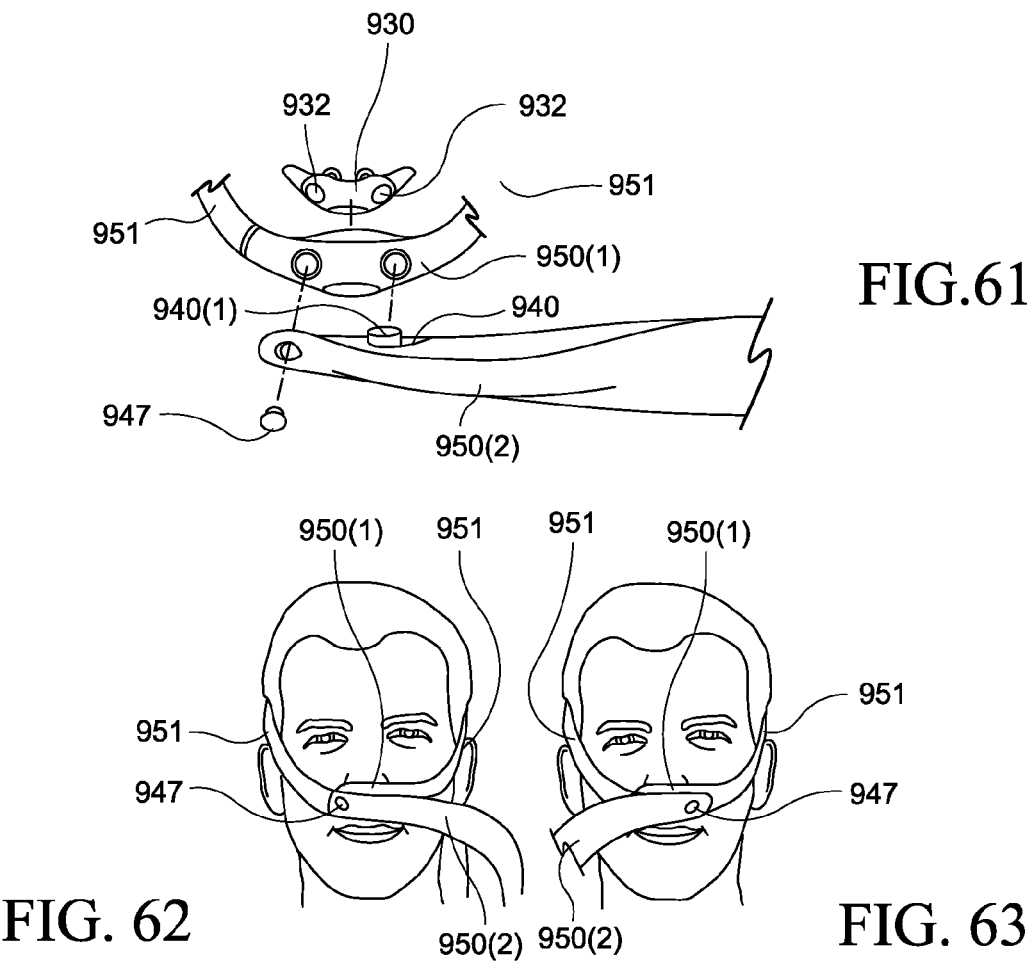
FIG. 58
FIG. 59
FIG. 60
FIG. 61
FIG. 62
FIG. 63

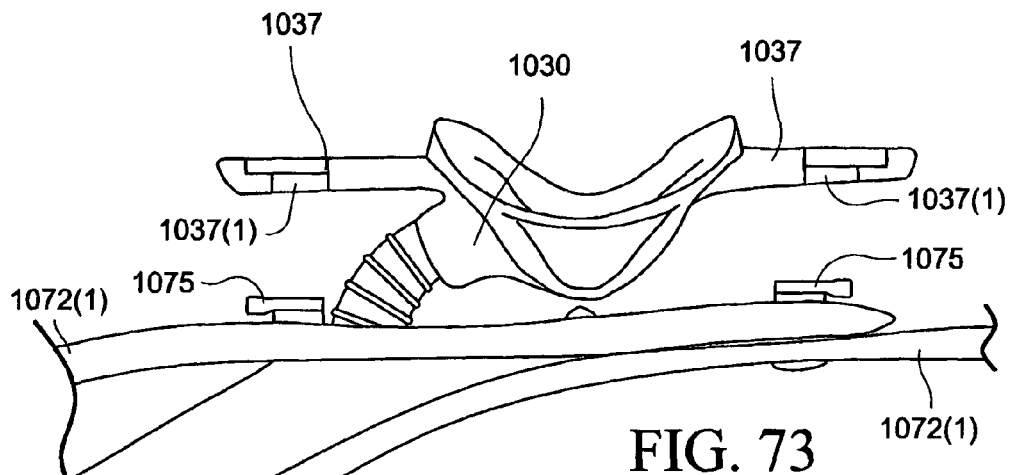
FIG. 73
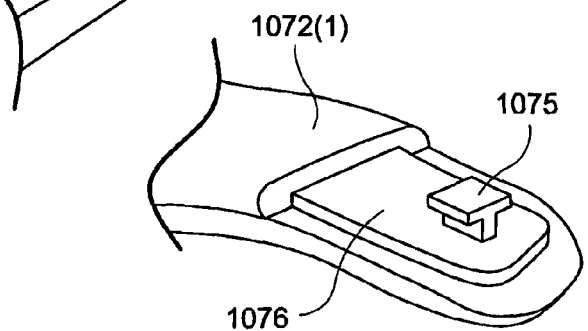
FIG. 72
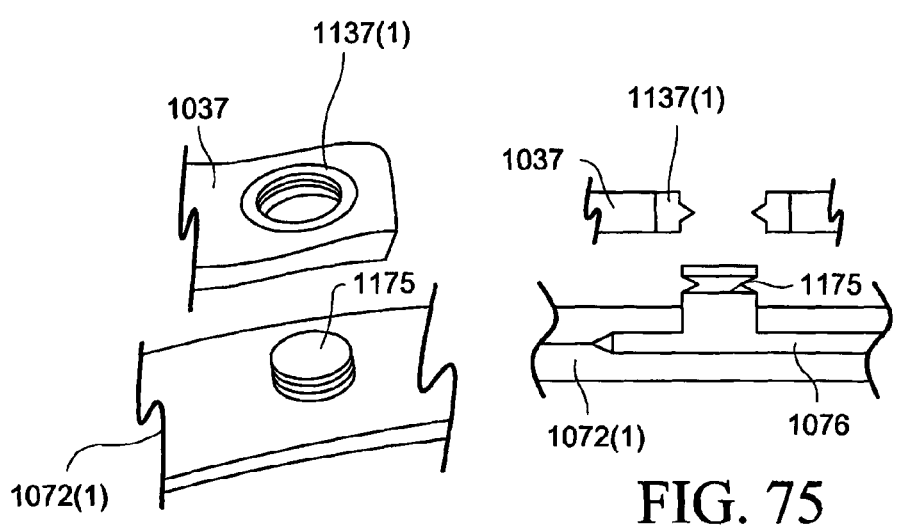
FIG. 75
FIG. 74

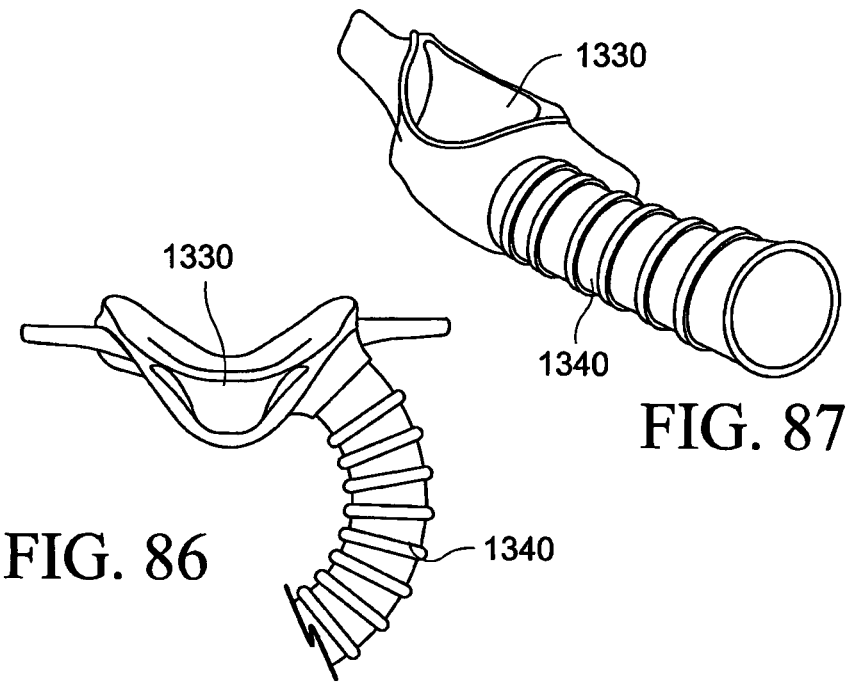
FIG. 86
FIG. 87
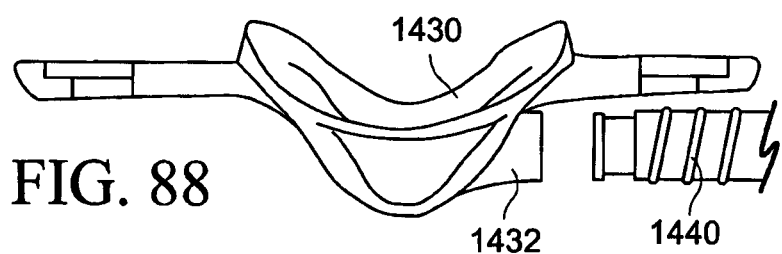
FIG. 88
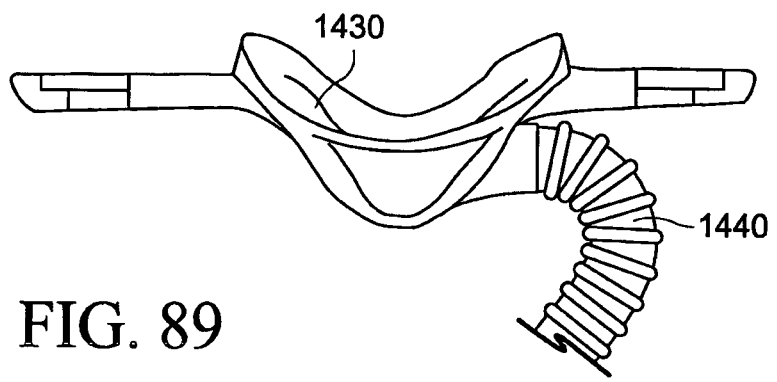
FIG. 89

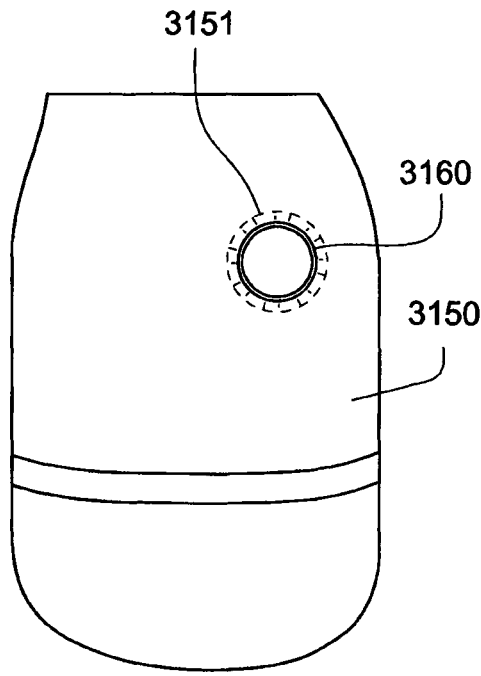
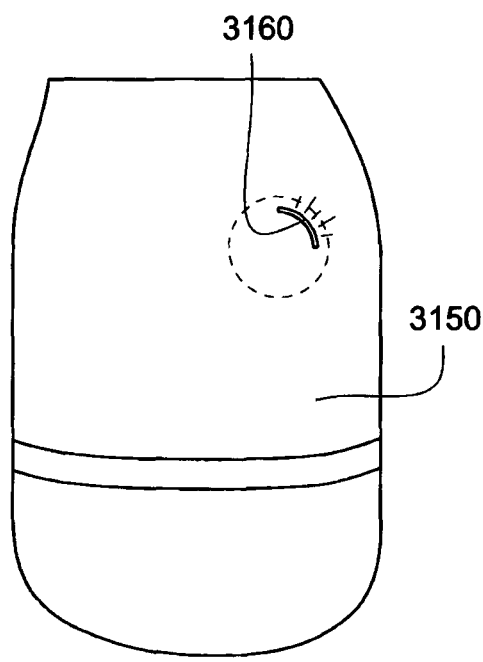
FIG. 131    FIG. 132
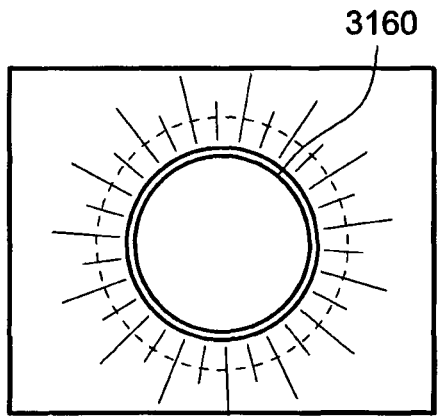
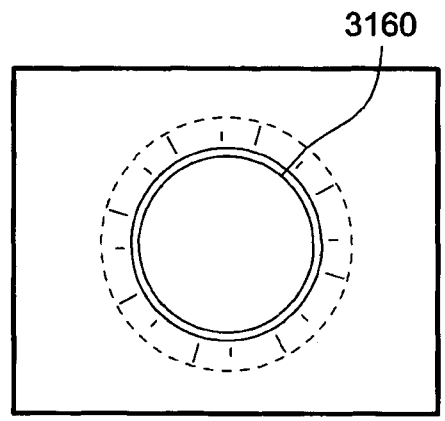
FIG. 133    FIG. 134

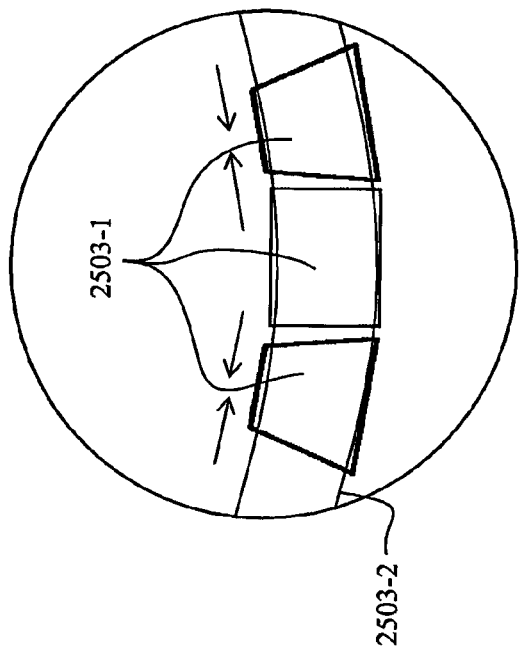
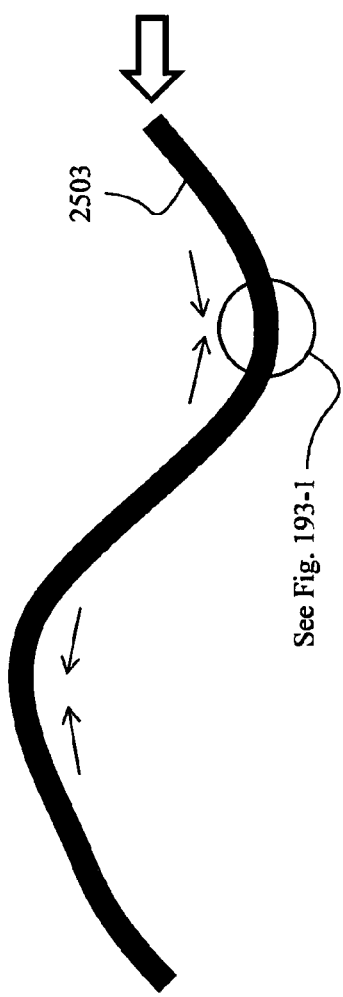
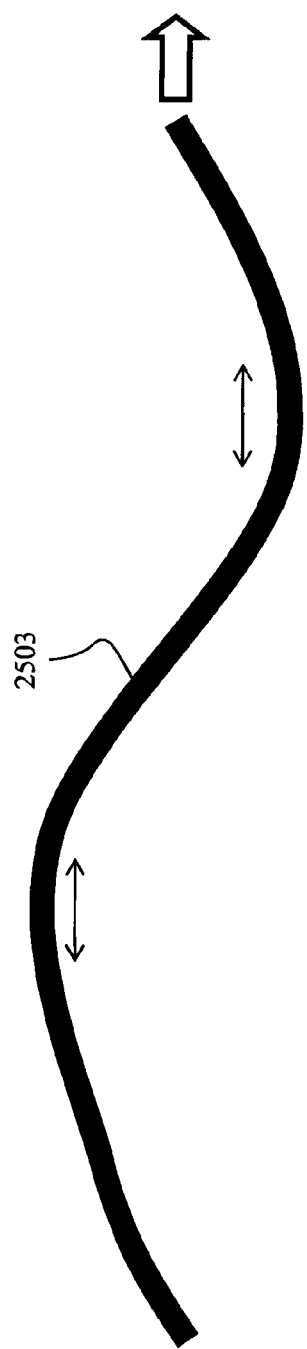
Fig. 193-1
Fig. 193-2
Fig. 193-3

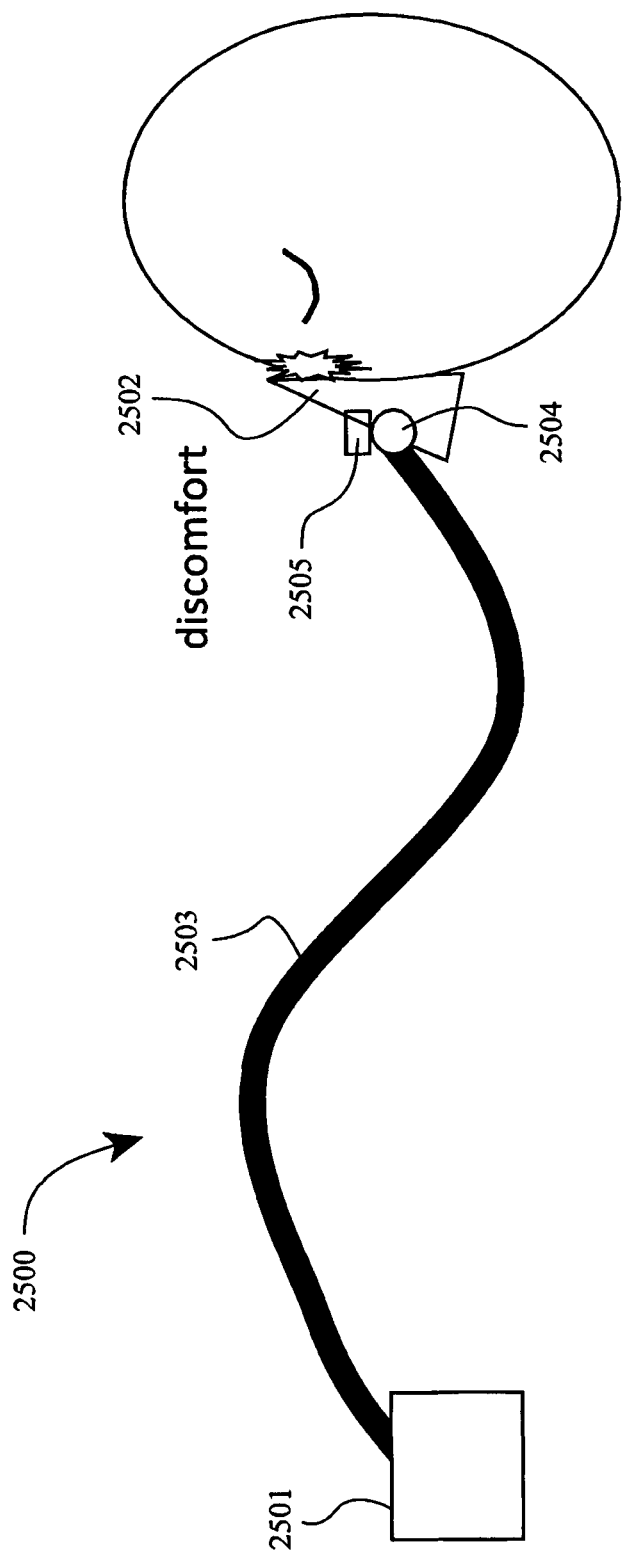

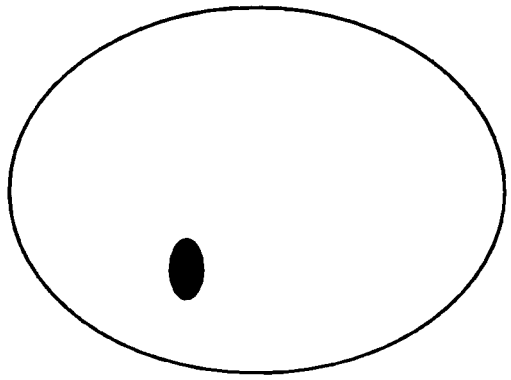
Patient awake
Fig. 197-1
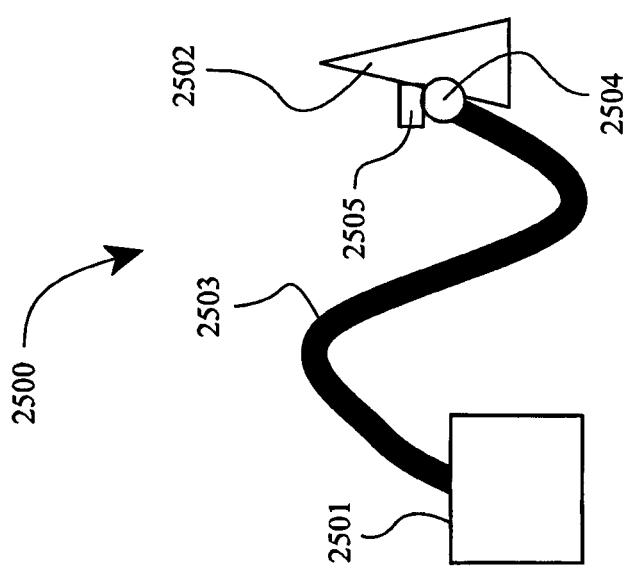

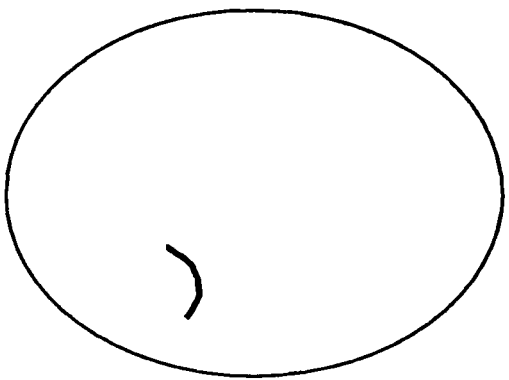
Patient asleep
Fig. 197-2
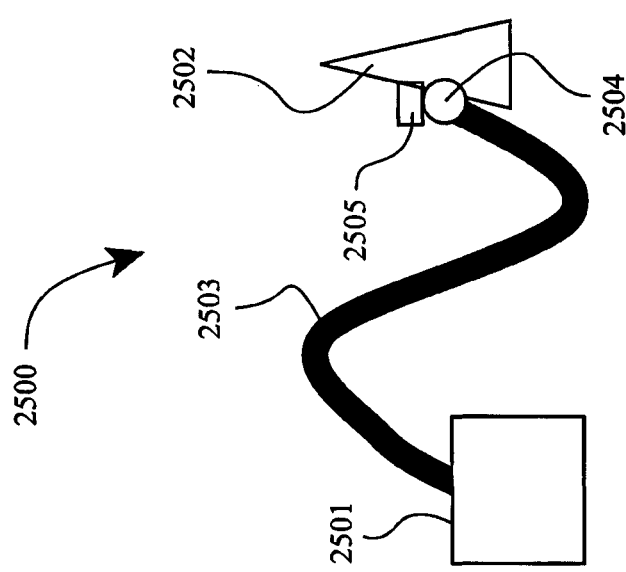

PAP SYSTEM

CROSS-REFERENCE TO APPLICATION

The application is the U.S. national phase of International Application No. PCT/AU2012/000720 filed 21 Jun. 2012 which designated the U.S. and claims the benefit of U.S. Provisional Application No. 61/457,858, filed Jun. 21, 2011, which are incorporated herein by reference in their entirety.

This application claims the benefit of U.S. Provisional Application No. 61/457,858, filed Jun. 21, 2011, which is incorporated herein by reference in its entirety.

FIELD OF TECHNOLOGY

The present technology relates to Positive Airway Pressure (PAP) systems and/or methods of use for treatment, e.g., of Sleep Disordered Breathing (SDB) with Continuous Positive Airway Pressure (CPAP) or Non-Invasive Positive Pressure Ventilation (NIPPV).

BACKGROUND OF TECHNOLOGY

Examples of head mounted blowers, wearable CPAP, or portable CPAP are known in the art. For example, see U.S. Patent Application Publications 2006/0237013 A1 and 2009/0320842 A1, each incorporated herein by reference, and the BreatheX™ system.

SUMMARY OF TECHNOLOGY

One aspect of the disclosed technology relates to PAP system including a PAP device for delivering pressurized air.

Another aspect of the disclosed technology relates to a PAP system including a cover that substantially encloses one or more portions of the PAP device and air delivery tubing.

Another aspect of the disclosed technology relates to a PAP system that is comfortable, less obtrusive, low impact, simplistic, easy to disassemble and clean, and/or low profile.

Another aspect of the disclosed technology relates to a PAP system that is comfortable to sleep with regardless of sleeping position.

Another aspect of the disclosed technology relates to a wearable PAP system that is minimal and appears wearable, so overall perception is improved (not like medical plumbing).

Another aspect of the disclosed technology is directed towards moving from a PAP system being used for "medical" reasons (e.g., CPAP for treatment of OSA) to a PAP system being used for general health reasons (e.g., snoring, asthma, occupational, allergies, sports, self-analysis of sleep). In an example, the PAP system may be obtained without a prescription, i.e., shift away from a physician and towards the consumer.

Another aspect of the disclosed technology relates to a PAP system including one or more components (e.g., patient interface, air delivery tubing, headgear) constructed of materials including different colors, patterns, and/or surface texture so as to blend in with the patient's skin and/or hair.

Another aspect of the disclosed technology relates to PAP systems including headgear straps and/or covers that wrap around the patient's head, a PAP device positioned on or adjacent the patient's head, bandana or scarf-like covers that cover the patient's face, and/or air delivery tubing passing along the patient's head.

Another aspect of the disclosed technology relates to a PAP system including a PAP device to generate a supply of pressurized air, a patient interface adapted to form a seal with the patient's face, air delivery tubing to interconnect the patient interface and the PAP device, and a cover that substantially encloses at least a portion of the PAP device and a portion of the air delivery tubing. The cover may allow the PAP device to be carried by and/or supported on the patient's body or head.

Another aspect of the disclosed technology relates to a system for delivery of pressurized air to a patient including a base unit including a blower to generate a supply of air at positive pressure, a patient interface adapted to be provided to a patient's face, and a tube to deliver the supply of pressurized air to the patient interface. The tube is structured to selectively modify its shape in order to move the patient interface and/or modify the amount of force exerted between the patient interface and the patient.

Another aspect of the disclosed technology relates to a mask system including a patient interface to communicate with at least one of the patient's airways, a sensor to generate a signal, e.g., related to patient breathing and/or movement, and a controller to receive the signal and to initiate a response, e.g., to adjust force, seal, and/or position of the patient interface relative to the patient. In an example, the signal may include patient movement and/or sleeping pattern, leak, leak location, and/or torque. In an example, the response may include angle adjustment of the patient interface and/or force provided by the patient interface. In an example, the response may be customized by the patient and/or physician.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIGS. 3A and 3B are exemplary cross-sections through the PAP system of FIG. 3;

FIG. 9A is an exemplary cross-section through the PAP system of FIG. 9;

FIG. 13 is a front view of a PAP system according to another example of the present technology;

FIG. 14 is a side view of the PAP system of FIG. 13;

FIGS. 19 to 42 show PAP systems according to alternative examples of the present technology;

FIG. 46 is a perspective view of a PAP system in use according to an example of the present technology;

FIG. 47 is another perspective view of the PAP system of FIG. 46 in use;

FIG. 48 is another perspective view of the PAP system of FIG. 46 in use;

FIGS. 49-1 to 49-6 show a retaining structure for a PAP device according to alternative examples of the present technology;

FIGS. 58 and 59 are perspective views of a patient interface according to an example of the present technology;

FIG. 60 is a perspective view of a base portion of a patient interface according to an example of the present technology;

FIG. 61 is a perspective view of a PAP system according to an example of the present technology;

FIGS. 62 and 63 show reversible positions of the PAP system of FIG. 61;

FIG. 72 is a perspective view of a connection tab within headgear of a PAP system according to an example of the present technology;

FIG. 73 is a perspective view of connection tabs within headgear of a PAP system according to an example of the present technology;

FIG. 74 is a perspective view of a connection post within headgear of a PAP system according to an example of the present technology;

FIG. 75 is a cross-sectional view showing the connection post of FIG. 74;

FIGS. 86 and 87 are various views of a one piece patient interface and air delivery tube according to an example of the present technology;

FIGS. 88 and 89 are various views of a patient interface with a direct connection to an air delivery tube according to an example of the present technology;

FIGS. 131 to 134 show a PAP system including a user interface according to another example of the present technology;

FIGS. 141-1 to 141-3 show a PAP device with a non-numeric display that changes color/intensity according to an example of the present technology;

FIGS. 142-1 and 142-2 show a PAP device with a non-numeric display including a bar graph according to an example of the present technology;

FIGS. 145-1 to 145-3 show a PAP system with a cover according to an example of the present technology;

FIGS. 146-1 to 146-2 show a PAP system with a cover according to an example of the present technology;

FIGS. 147-1 to 147-3 show a PAP system with a cover according to an example of the present technology;

FIGS. 148-1 to 148-3 show alternative examples for assembling the PAP device and tubing into the cover of the PAP system;

FIGS. 152-1 to 152-3 show a PAP system with a cover according to another example of the present technology;

FIGS. 153-1 to 153-3 show a PAP system with a cover according to another example of the present technology;

FIGS. 154-1 to 154-3 show a PAP system with a cover according to another example of the present technology;

FIGS. 155-1 to 155-3 show a PAP system with a cover according to another example of the present technology;

FIG. 193-1 is an enlarged schematic view of active elements of an active tube or smart tube according to an example of the present technology;

FIGS. 193-2 and 193-3 are schematic views of an active tube or smart tube in contracted and extended positions according to an example of the present technology;

FIGS. 195-1 to 195-4 show schematic views of a system adjusting the total force applied to the patient's face by the patient interface in response to leak or patient discomfort according to an example of the present technology;

FIGS. 196-1 to 196-4 show schematic views of a system adjusting the force angle applied to the patient's face by the patient interface in response to leak or patient discomfort according to an example of the present technology;

FIGS. 197-1 to 197-3 show schematic views of a system including a patient interface structured to automatically locate the patient's face and fit itself after the patient falls asleep according to an example of the present technology;

FIG. 198 is a schematic view of a system according to another example of the present technology;

FIG. 199 is a schematic view of a system according to another example of the present technology;

FIG. 200 is a schematic view of a system according to another example of the present technology;

FIG. 201 is a graph showing duration of use for determining an evaluation result according to an example of the present technology; and FIG. 202 is a graph showing noise free duration for determining an evaluation result according to an example of the present technology.

DETAILED DESCRIPTION OF ILLUSTRATED EXAMPLES

Figure 4:
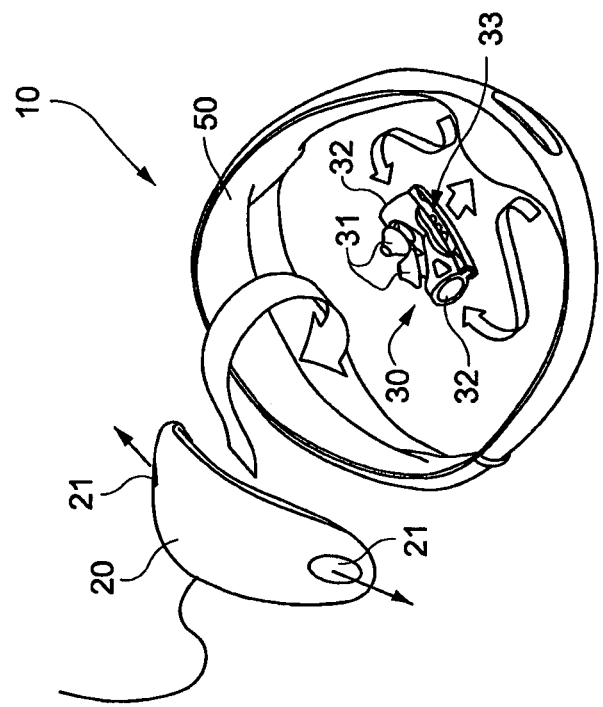
FIG. 4 is an exploded view of the PAP device of FIG. 1.

The following description is provided in relation to several examples (most of which are illustrated, some of which may not be) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The term "wearable" will be taken to refer to a system that is portable, lightweight and/or small to consequently allow the user to move around while wearing the system.

The subject headings used in the detailed description are included only for the ease of reference of the reader and should not be used to limit the subject matter found throughout the disclosure or the claims. The subject headings should not be used in construing the scope of the claims or the claim limitations.

1. PAP System

A PAP system typically includes a PAP device (including a blower for generating air at positive pressure), an air delivery conduit (also referred to as a tube or tubing), and a patient interface (e.g., mask). In use, the PAP device generates a supply of pressurized air (e.g., 2-30 cm $H_2O$) that is delivered to the patient interface via the air delivery conduit. The patient interface or mask may have suitable configurations as is known in the art, e.g., full-face mask, nasal mask, oro-nasal mask, mouth mask, nozzles, nasal prongs, nasal pillows, cannula, nasal cradle, etc. Also, headgear may be utilized to comfortably support the patient interface in a desired position on the patient's face.

Certain examples relate to PAP systems in which the PAP device or blower is adapted to be worn on the patient's head, is built into or incorporated into the patient interface or mask, is wearable or carried by the patient, is portable, is reduced in size or combinations thereof. In certain examples, the PAP system may be of the type described in PCT Application Nos. PCT/AU2010/001031 and/or PCT/AU2010/001106, each of which is incorporated herein by reference in their entirety.

In an example, the PAP system is intended to be worn during sleep as a single patient use device to provide relief for snoring disorders associated with reduced airflow. The PAP system decreases airway resistance and increases airflow through the nasal passages.

In an example, the PAP system may be structured to deliver pressurized gas at a pressure of about 6 $cmH_2O$ (e.g., this may be the maximum pressure) at 60 lpm at mask, constant flow. In an example, the PAP system may include 90-260 Volts Alternating Current (VAC), 50-60 Hz mains input power, power cord/plug selected to source. In an example, the target audible noise level may be comparable to standard CPAP systems. In an example, the PAP system appearance may be sleek and non-medical, unlike a traditional CPAP system. In an example, the PAP system may provide simple and intuitive use and connections that incorporate a single ON/OFF switch. In an example, the PAP system may provide a patient interface or mask that is easy to fit and prevents leak without any special training.

2. Exemplary Headworn PAP System—Loop Example

FIGS. 1 to 6 illustrate a headworn PAP system 10 including a PAP device 20 (also referred to as a flow generator or blower), a patient interface 30 (e.g., nozzles, pillows, prongs, or nasal cushion arrangement), and air delivery tubing 40 (e.g., one or more tubes or inlet conduits) that interconnect the patient interface and the PAP device. A cover 50 substantially encloses one or more portions of the PAP device, patient interface, and air delivery tubing to secure such components in position on the patient's head in use. In an example, the components may be easily disassembled, e.g., for cleaning, replacement, etc.

As illustrated, the PAP system defines a loop that passes generally along an underside of the patient's nose, along the cheek region, above the ears, and over the crown and parietal portion of the patient's head so as to stabilize the PAP system on the patient's head and provide sealing forces against the patient's nose. In an alternative example, the loop may pass below the patient's ears and then over the crown and parietal portion of the patient's head.

2.1 PAP Device

Figure 5:
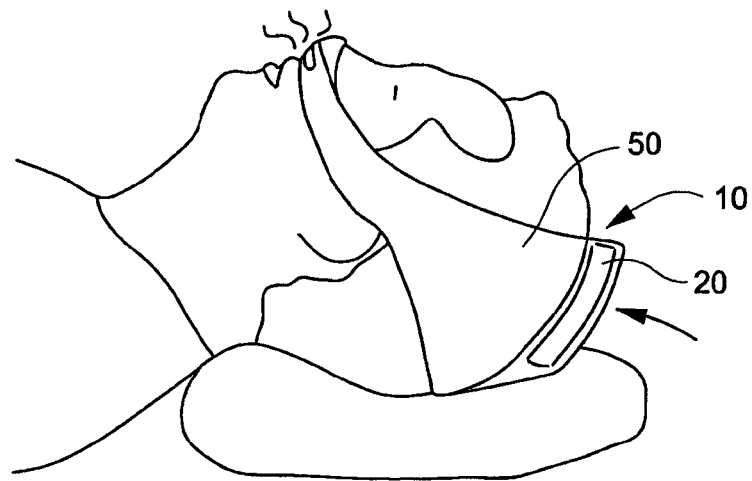
FIG. 5 is a side view of the PAP system of FIG. 1 in use.
Figure 6:
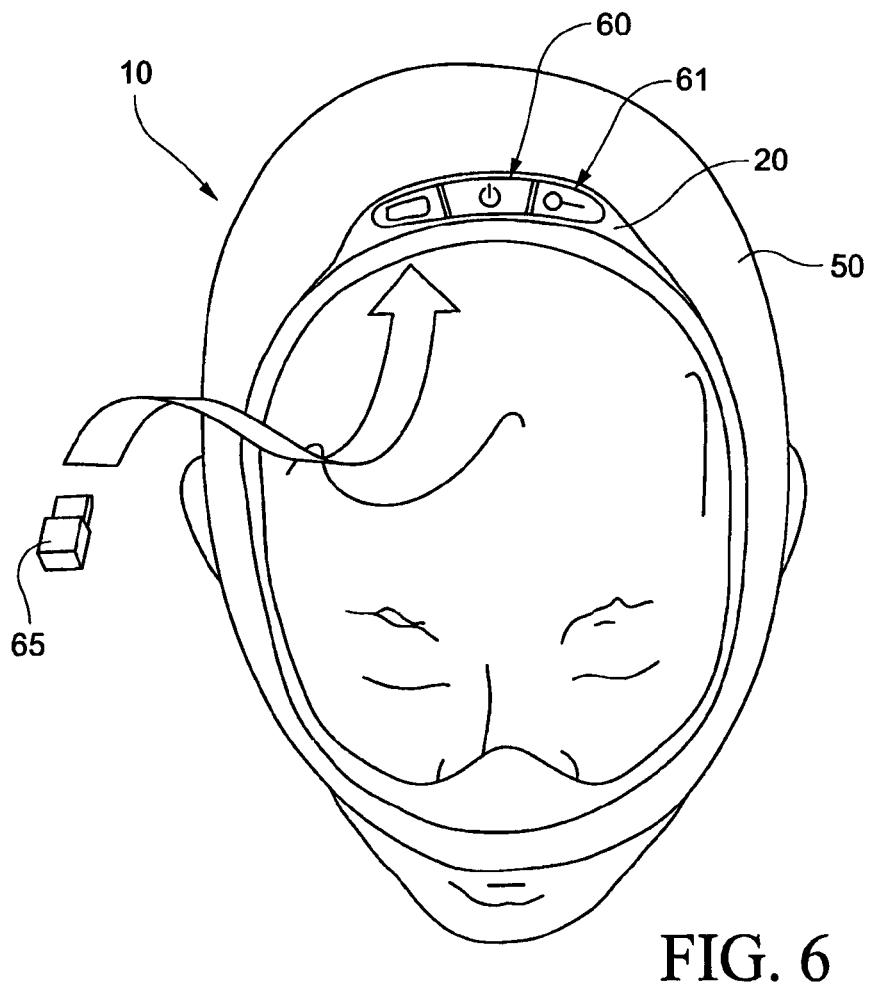
FIG. 6 is a front perspective view of the PAP system of FIG. 1.
Figure 8:
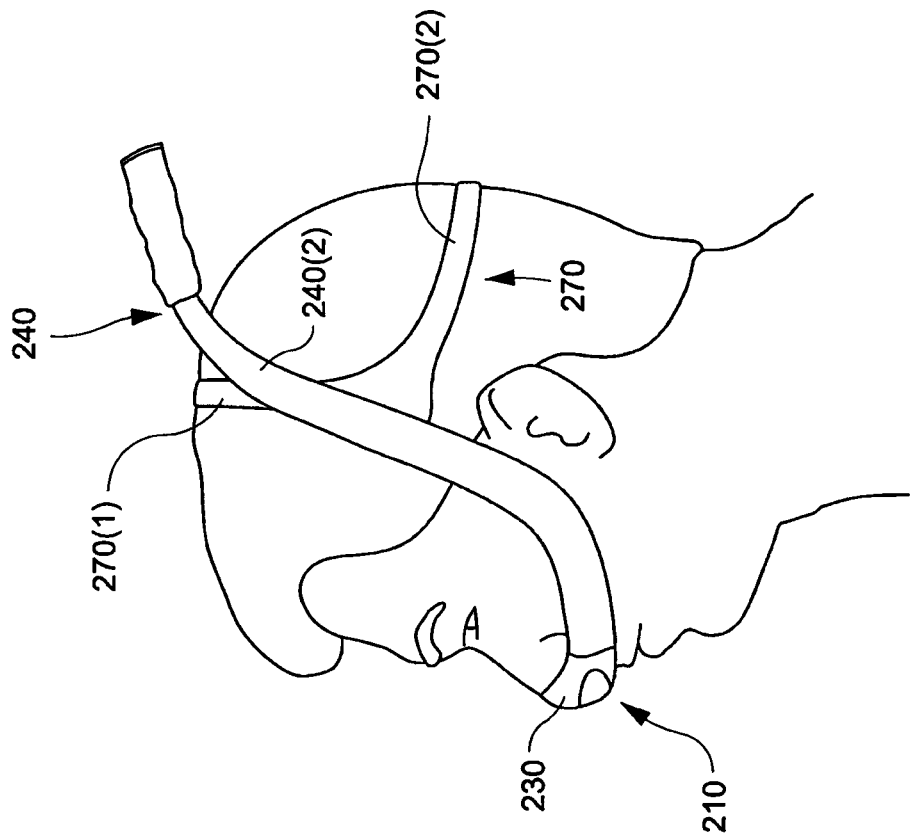
FIG. 8 is a side view of the PAP system of FIG. 7.
Figure 7:
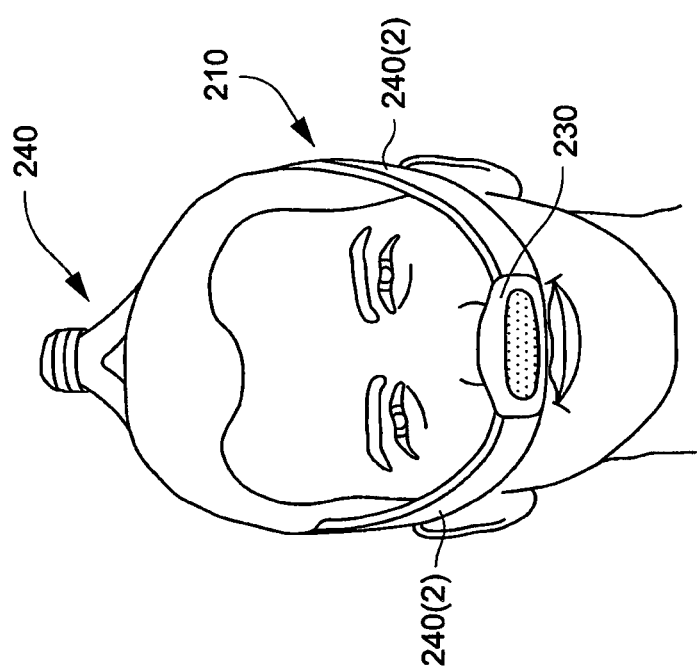
FIG. 7 is a front view of a PAP system according to another example of the present technology.

The PAP device 20 is supported within the cover 50 so it sits on top of the patient's head in use, e.g., supported on the crown and/or parietal portion of the patient's head. As shown in FIG. 5, such positioning does not obstruct the inlet or air intake of the PAP device (e.g., provided along a top portion of the PAP device) in use, i.e., air intake is unrestricted regardless of the sleeping position of the patient, e.g., lying on back or his/her side. Each side of the PAP device 20 includes an outlet or outlet opening 21 (e.g., see FIG. 4) structured to communicate with a respective air delivery tube such that the PAP device delivers air along both sides of the patient's head in use. As shown in FIG. 6, one or more controls 60 for the system (e.g., controls for PAP device) may be provided on the top of the patient's head, e.g., for easy access by the patient and/or health care professional.

As illustrated (e.g., see FIG. 4), the outer casing of the PAP device may be suitably contoured and configured to substantially match the contours of the patient's head, e.g., for comfort, less obtrusive, low impact, low profile, etc.

2.2 Patient Interface

In the illustrated example, the patient interface 30 may include a nozzle, nasal prong, pillows, or cushion arrangement (e.g., constructed of silicone) including nozzles, nasal prongs, pillows, or cushion 31 adapted to form a seal with the patient's nares. Each side of the nozzle arrangement includes an inlet or inlet opening 32 structured to communicate with a respective air delivery tube. The nozzle arrangement may include a vent 33 to allow the exhalation of gases from the patient interface and patient.

While the illustrated patient interface is of the nozzle type, it should be appreciated that such interface type is merely exemplary, and other interfaces are possible, e.g., nasal mask, full-face mask, mouth mask, under-the-nose interface, etc. In addition, the patient interface may be constructed of other suitable materials, e.g., silicone, foam, gel, textile, etc. In an example, the patient interface may include a "flower" type interface as described in WO 2010/139014, which is incorporated herein by reference in its entirety.

2.3 Air Delivery Tubing

Each air delivery tube 40 includes a first end configured to connect to a respective outlet of the PAP device 20 and a second end configured to connect to a respective inlet of the patient interface 30. In use, the tubes are supplied with pressurized breathable gas from the PAP device, and the pressurized breathable gas is delivered into opposing ends of the interface.

As shown in FIG. 3A, each tube 40 may have a non-cylindrical cross-sectional shape structured such that it may move between two phases, i.e., a first open phase (FIG. 3A) and a second at least partially collapsed phase (FIG. 3B) in which the tube is at least partially collapsed and comfortable to lie on. In the second at least partially collapsed phase (FIG. 3B), opposing walls of the tube may engage one another at one or more points or surfaces along their length such that conductance through the at least partially collapsed tube may be minimized. Each tube is structured to handle full pressure in use. Further examples of such tubing are disclosed in U.S. Publication No US-2008-0060649, which is incorporated herein by reference in its entirety.

It is preferred that two tubes be used, so that a sufficient supply of breathable gas can still be delivered to the patient interface when one of the tubes is at least partially collapsed, e.g., due to the patient lying on his/her side. That is, when two tubes are used, one or both of the tubes may be open in use. However, it should be appreciated that a single tube or more than two tubes may be used, e.g., three or more tubes.

2.4 Cover

One or more portions of the cover 50 may be constructed of a textile material, e.g., breathable fabric to reduce perception of heat and demonstrate performance.

One or more portions of the cover 50 may include a clear portion or window/opening, e.g., to show the patient's face and reveal technology. For example, the cover may include clear portions 50(1), 50(2) to expose portions of the seal of the patient interface and air delivery tubing and an opening 50(3) to expose the vent of the patient interface.

One or more portions of the cover may have different colors (color contrast), patterns, and/or surface texture. For example, a blue pinstripe may be provided along the cover to provide a performance element that shows air flow. Also, a hang tag may be provided to the cover to provide apparel aesthetic and soft brand treatment. In addition, the cover may include a two-tone color scheme to reduce visual thickness or provide orientation, e.g., distinct inside and outside surfaces.

Further examples of covers are disclosed in U.S. Publication No. US-2008-0047560, which is incorporated herein by reference in its entirety.

In an example, the cover may be formed in one piece (e.g., co-molded) with the air delivery tubing. In an example, the cover may constitute or otherwise provide the air delivery path from the PAP device to the patient interface, i.e., textile-type tubing in lieu of silicone-type air delivery tubing.

3. Exemplary PAP System—Pillow Example

FIGS. 7 to 12 illustrate a PAP system 210 according to another example of the disclosed technology. In this example, the PAP system includes a PAP device 220 adapted to be positioned in, under, or adjacent the patient's pillow in use, a patient interface 230 (e.g., nozzle/nasal prong arrangement), and air delivery tubing 240 (e.g., outlet tube 240(1) that bifurcates into two inlet tubes 240(2)) that interconnect the patient interface and the flow generator. Headgear including a single generally circular strap 270 (e.g., crown strap portion 270(1) and back strap portion 270(2)) is provided to stabilize and support the patient interface and inlet tubes on the patient's head. The single generally circular strap simplifies taking the PAP system on and off the patient's head. A cover 250 substantially encloses one or more portions of the PAP device 220 and the outlet tube 240(1) of the air delivery tubing. In an example, the components may be easily disassembled, e.g., for cleaning, replacement, etc.

The patient interface and inlet tubes may define a loop that passes generally along an underside of the patient's nose, along the cheek region, above the ears, and over the crown of the patient's head. The system provides seamless transitions, i.e., simple flowing shape is minimal and appears wearable, so overall perception is improved (not like medical plumbing). Also, the system provides an aesthetic which is transparent about the air sensation provided by the system. In an alternative example, the tubes may pass below the patient's ears and then over the crown of the patient's head.

In this example, the patient interface, inlet tubes, and headgear may be constructed of materials including different colors, patterns, and/or surface texture so as to blend in with the patient's skin and hair (e.g., "disappearing" materials). For example, the patient interface and inlet tubes may be constructed of a substantially transparent material (e.g., silicone) such that it is transparent or blends in with the patient's face. The headgear (generally circular strap) may be constructed of a material to blend in with the patient's hair, e.g., warm grey fabric which is disguised by the patient's hair. It should be appreciated that the materials may be suitably selected for different users.

3.1 PAP Device

Figure 9:
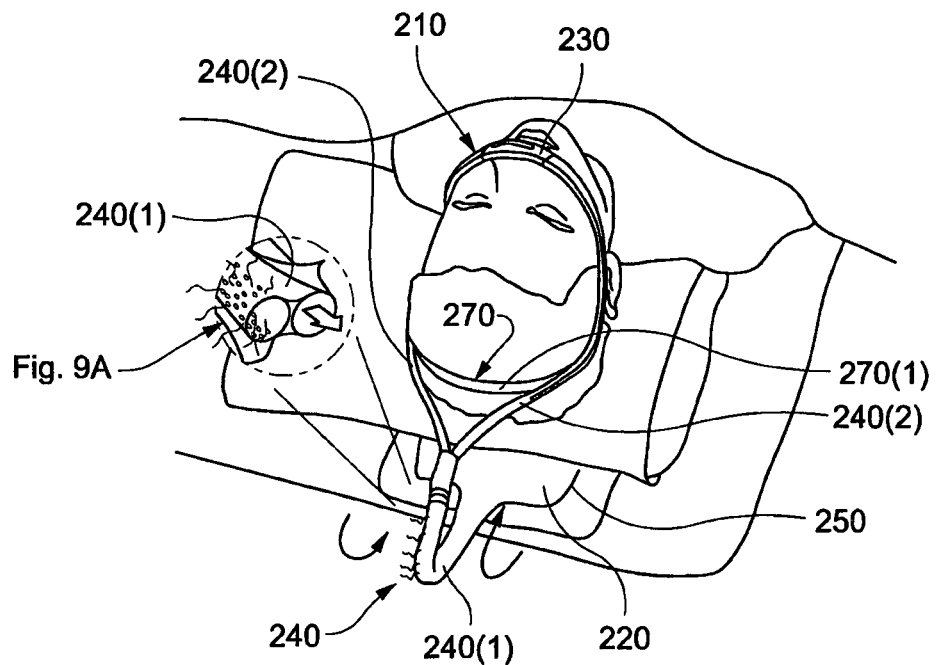
FIG. 9 is a top perspective view of the PAP system of FIG. 7 in use.
Figure 10:
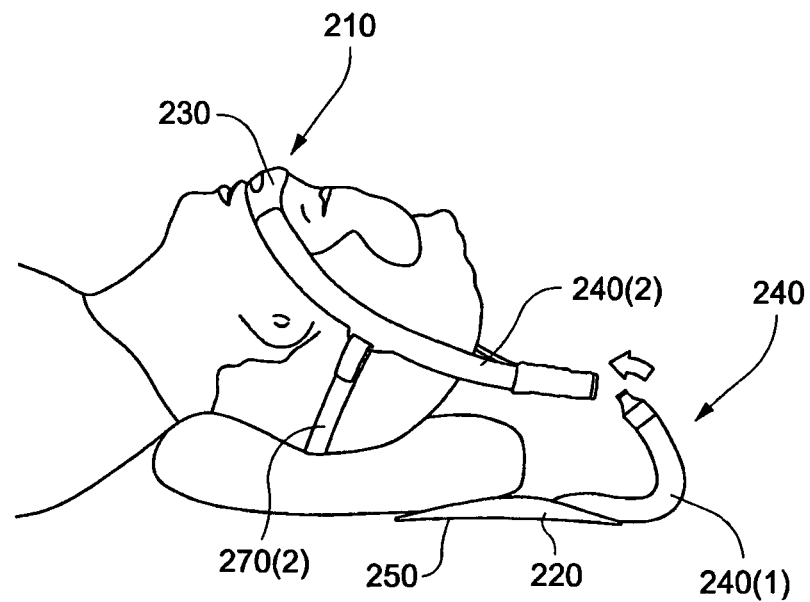
FIG. 10 is a side view of the PAP system of FIG. 7 in use.

As best shown in FIGS. 9 and 10, the PAP device 220 is located within the cover 250 and adapted to be positioned under or adjacent the patient's pillow in use. The PAP device provides a substantially low profile so it is not obtrusive and does not significantly affect the patient's sleeping position.

Figure 45:
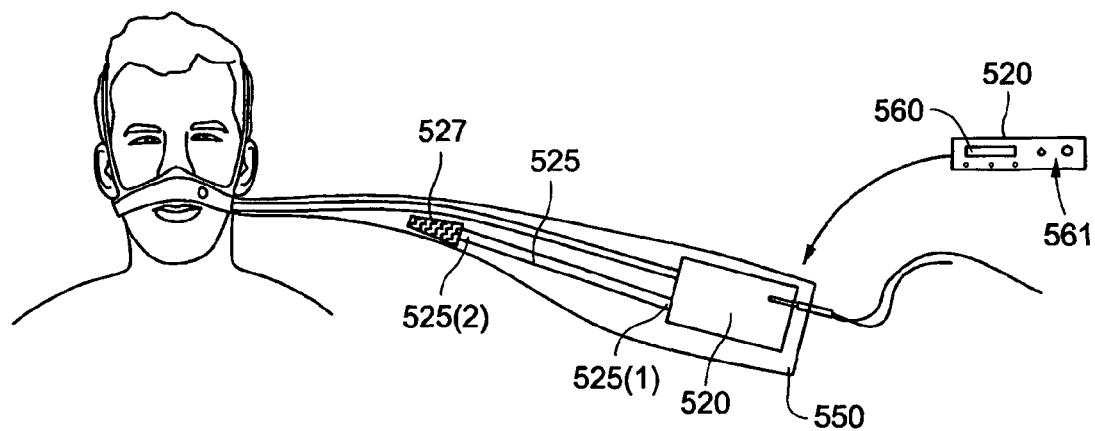
FIG. 45 is a schematic view of a PAP system according to another example of the present technology.

The PAP device may include an extended feature for drawing air through the inlet or air intake of the PAP device in use (e.g., see FIG. 45 embodiment). The extended feature may include an elongated inlet or air intake (not shown) having a first end attached to the inlet of the PAP device 220 and a second end adapted to be positioned to receive air from the surroundings. The second end of the elongated inlet or air intake may also have an inlet filter 527 to remove particulates. In an example, the elongated inlet or air intake and the air delivery tubing may run in parallel directions or alternatively in different directions.

Figure 11:
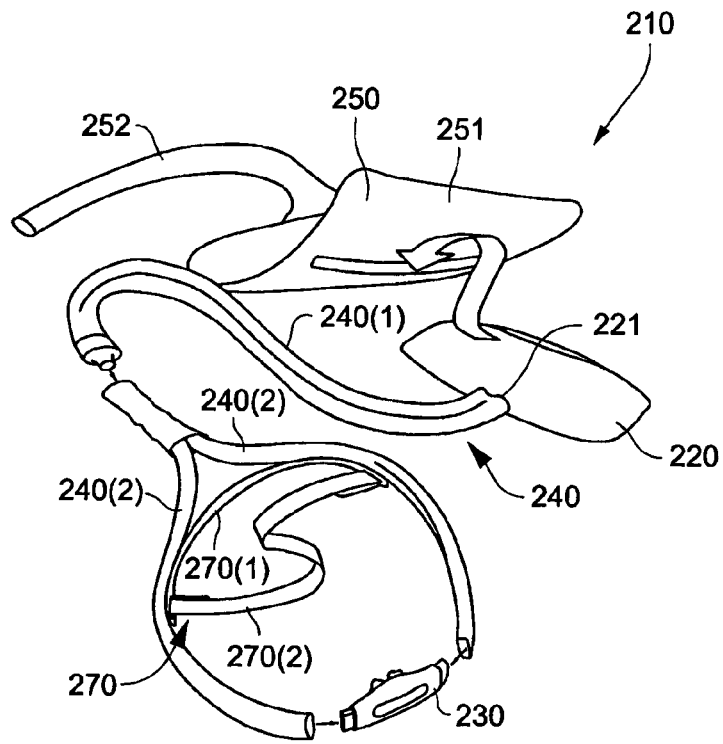
FIG. 11 is an exploded view of the PAP device of FIG. 7.
Figure 12:
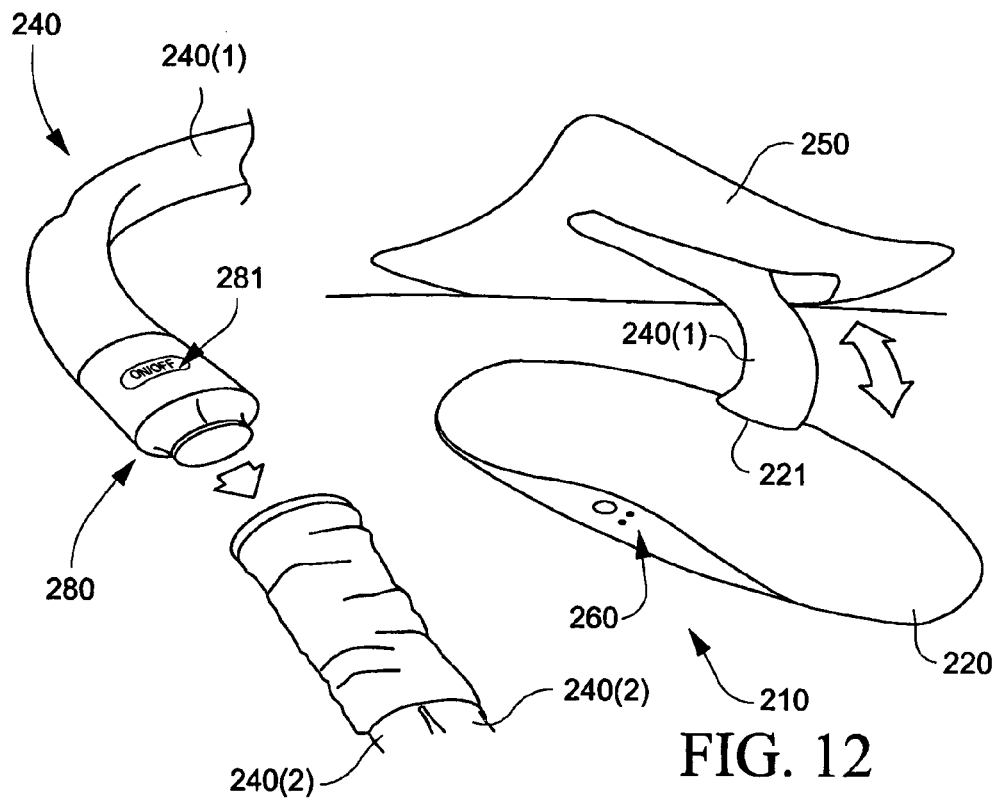
FIG. 12 is another exploded view of the PAP device of FIG. 7.

The PAP device includes an outlet or outlet opening 221 structured to communicate with the outlet tube 240(1) of the air delivery tubing (e.g., see FIGS. 11 and 12).

As shown in FIG. 12, a Hi/Low pressure control/toggle 260 may be located on the PAP device. It should be appreciated that additional controls for the system may be provided to the PAP device.

3.2 Patient Interface

In the illustrated example, the patient interface 230 includes a nozzle/nasal prong arrangement as described above (e.g., see FIG. 11). However, other suitable interfaces are possible, e.g., nasal mask, full-face mask, mouth mask, under-the-nose interface, etc.

3.3 Air Delivery Tubing

In the illustrated example, the air delivery tubing 240 includes an outlet tube 240(1) having two tubes joined together (e.g., see FIG. 9A) at the outlet of the PAP device (e.g., both tubes adapted to be coupled to a single outlet of the PAP device), and then the tubes bifurcate (i.e., split or divide into separated inlet tubes 240(2)) towards respective ends of the patient interface.

As described above, the inlet tubes 240(2) may have a non-cylindrical cross-sectional shape structured such that it may move between open and at least partially collapsed phases. In addition, the cross-section shape includes a blending contour that is smooth, streamlined, sleek, and blends or tapers the tubes with or into the contours of the patient's head (not like standard medical plumbing or tubing).

In an example as best shown in FIG. 12, a quick disconnect 280 may be provided between the inlet tubes 240(2) and the outlet tube 240(1) extending from the PAP device, e.g., to allow the patient to get up during the night without having to remove the entire patient interface. In an example, an On/Off control 281 may be provided or coupled to the quick disconnect 280, e.g., to easily turn off the PAP device when arising.

3.4 Cover

As shown in FIG. 11, the cover 250 includes a pouch portion 251 to substantially enclose one or more portions of the PAP device 220 and a tube portion 252 to substantially enclose one or more portions of the outlet tube 240(1).

4. Exemplary PAP System—Wrap Example

FIGS. 13-18 illustrate a PAP system 310 according to another example of the disclosed technology. In this example, the PAP system 310 includes a PAP device 320, a patient interface 330 (e.g., nozzle/nasal prong/cushion arrangement), and air delivery tubing 340 to interconnect the patient interface and the flow generator. A cover 350 substantially encloses one or more portions of the PAP device and the air delivery tubing. In addition, the cover includes a headgear strap portion 355 that cooperates with another headgear strap 370 to wrap around the patient's head to stabilize and support the system on the patient's head. In an example, the components may be easily disassembled, e.g., for cleaning, replacement, etc. Also, the system provides human asymmetry, which may help to eliminate "face widening" effect, and show orientation.

4.1 PAP Device

Figure 16:
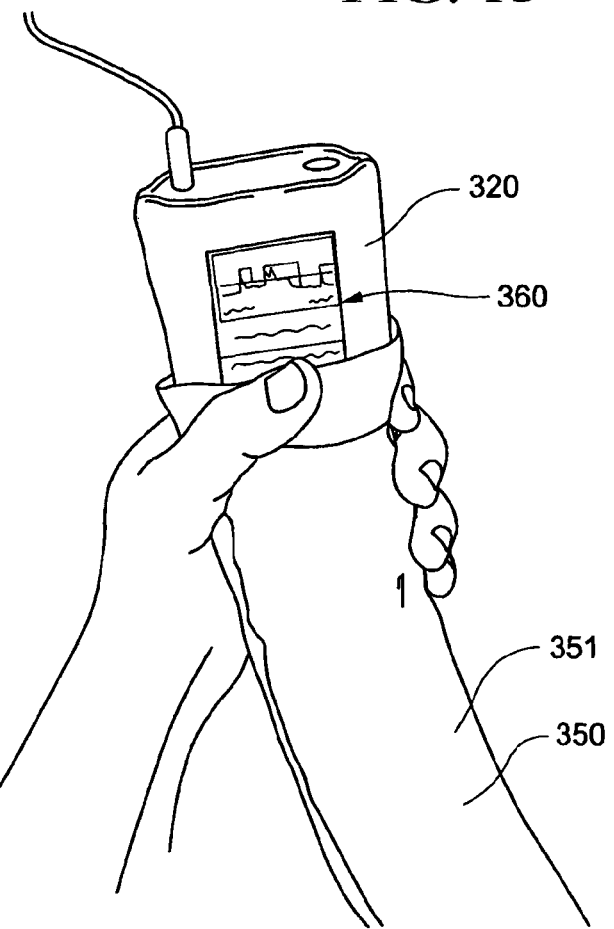
FIG. 16 is a perspective view of a PAP device and cover of the PAP system of FIG. 13.

The PAP device 320 is supported within the cover 350. In an example, as shown in FIG. 16, the PAP device 320 may extend out of the end of the cover to allow access to one or more controls 360 provided to the PAP device.

Figure 15:
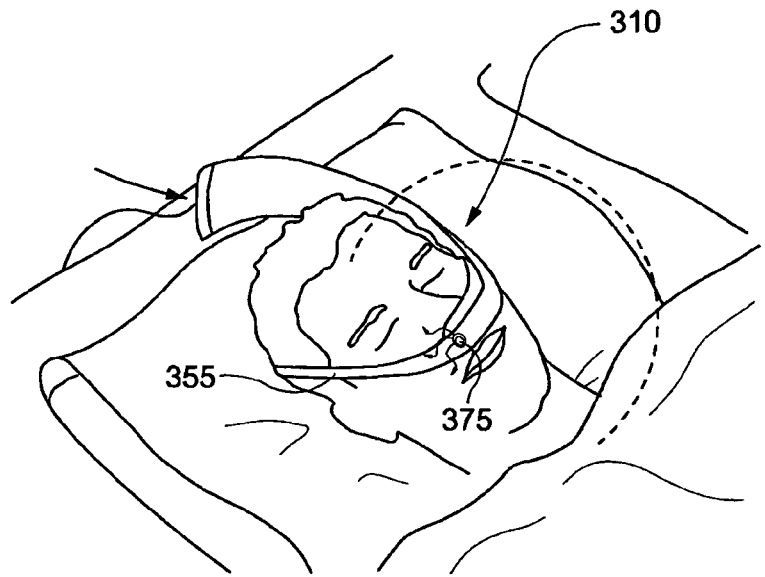
FIG. 15 is a front perspective view of the PAP system of FIG. 13 in use.

When the patient is standing as shown in FIG. 14, the PAP device may be suspended from the patient's head by the tubing so it is positioned adjacent to and/or supported by the patient's shoulder. When the patient is lying in bed as shown in FIG. 15, the PAP device may be positioned adjacent the patient's head (e.g., on, under or adjacent the patient's pillow). The PAP system 310 is illustrated as being configured to wrap across to the left side of a patient's body or face. However, it is to be understood that the PAP system 310 may also be configured to wrap across to the right side of a patient's body or face.

Figure 18:
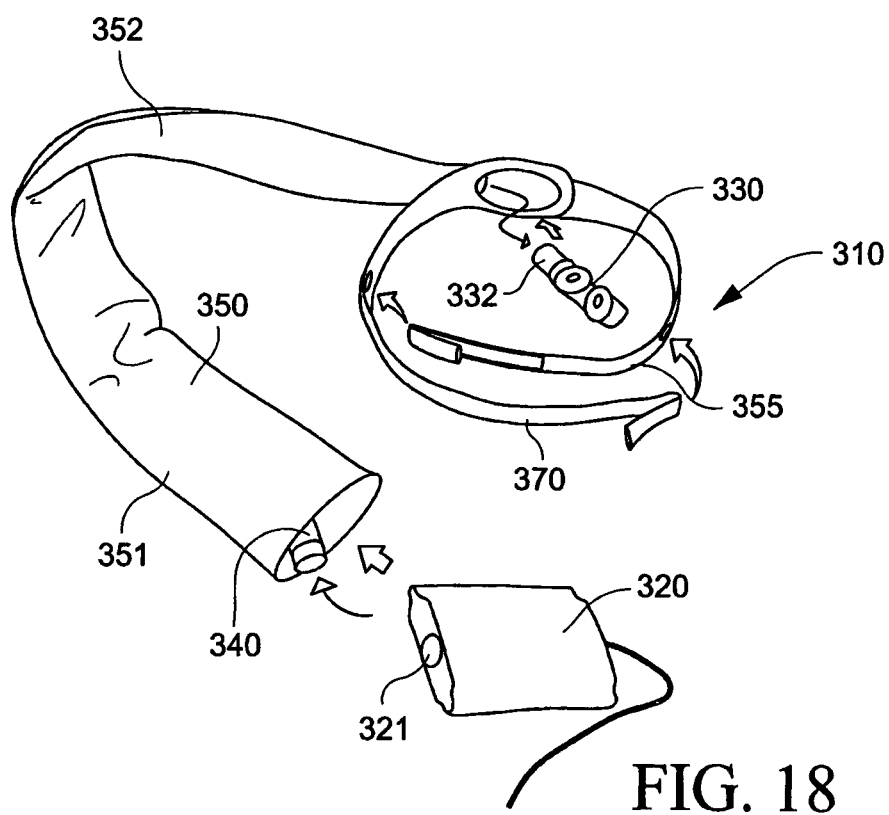
FIG. 18 is an exploded view of the PAP device of FIG. 13.

The PAP device 320 includes an outlet or outlet opening 321 structured to communicate with the air delivery tubing 340 (e.g., see FIG. 18). As shown in FIG. 15, the suspended arrangement of the PAP device from the patient's head allows for a flexible sleeping position, e.g., PAP device may be pivoted 180° with respect to the patient's head.

4.2 Patient Interface

In the illustrated example, the patient interface 330 includes a nozzle/nasal prong arrangement (e.g., constructed of silicone) including nozzles/nasal prongs adapted to form a seal with the patient's nares (e.g., see FIG. 18). In this example, only one side of the nozzle arrangement includes an inlet or inlet opening 332 structured to communicate with the air delivery tubing. The nozzle arrangement may include a vent to allow the exhalation of gases from the patient interface and patient. However, other suitable interfaces and interface arrangements are possible, e.g., nasal mask, full-face mask, mouth mask, under-the-nose interface, etc.

4.3 Air Delivery Tubing

In the illustrated example, the air delivery tubing 340 includes a single tube supported within the cover 350 and connected between the outlet of the PAP device and the inlet of the nozzle arrangement. As shown in FIGS. 13 to 15, the covered tube wraps around the patient's head, e.g., like a scarf.

4.4 Cover

As best shown in FIGS. 14 and 18, the cover 350 includes a pouch portion 351 to substantially enclose one or more portions of the PAP device, a tube portion 352 to substantially enclose one or more portions of the air delivery tube, and a headgear strap portion 355 that cooperates with another headgear strap to wrap around the patient's head to stabilize and support the system on the patient's head.

The headgear strap portion 355 is structured to wrap along the cheek region, above the ears, and around the back of the patient's head, and connect to an intermediate portion of the headgear strap 370 (e.g., headgear strap includes loop that allows headgear strap portion to wrap therearound) so as to define a back strap for supporting the system. The headgear strap 370 is structured to wrap under the patient's nose, along the cheek region, above the ears, and over the crown of the patient's head, and connect to an intermediate portion of the headgear strap portion 355 (e.g., headgear strap portion includes loop that allows headgear strap to wrap therearound) so as to define a crown strap for supporting the system. In an alternative example, the strap may pass below the patient's ears and then over the crown of the patient's head.

The headgear strap portion 355 and headgear strap 370 overlap by the patient's nose. The headgear strap portion and headgear strap may be connected to one another at the overlap, e.g., by a button 375 (e.g., reminiscent of a beauty mark), which may also serve as a vent from the patient interface (e.g., see FIGS. 13 and 15). The overlapped connection may reduce visual weight in the nose area.

Figure 17:
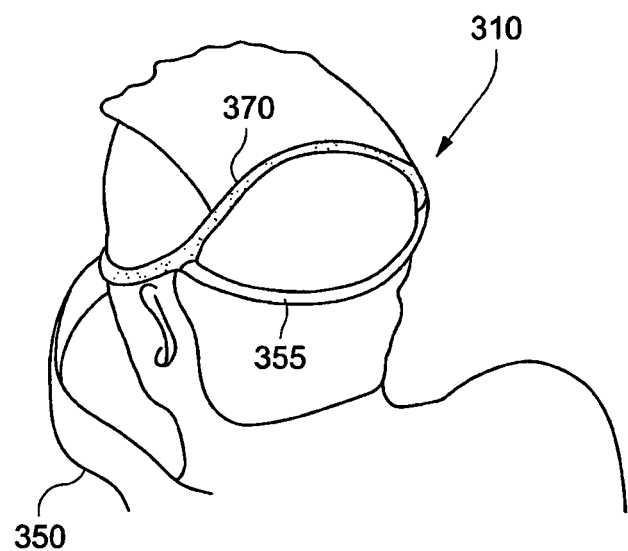
FIG. 17 is a rear perspective view of the PAP system of FIG. 13 in use.

One or more portions of the cover 350 may be constructed of a textile material, e.g., bedroom-like fabrics, which may connect the system with the environment and contribute to overall approachability and comfort. Also, as shown in FIG. 17, the headgear strap portion 355 and headgear strap 370 may include a two-tone color arrangement to provide quick-read orientation. The two-tone color arrangement may minimize the appearance and size of the device as well as indicate which side of the device faces the patient, e.g., see FIGS. 106-125.

5. Controls and Feedback Examples

The following provides alternative examples of controls and feedback for PAP systems including for use with any one of the exemplary PAP systems described herein.

5.1 Basic Controls, No Feedback

In an example, the PAP system may include basic controls to keep costs low, but such basic controls may provide little if any feedback to the patient.

FIG. 12 illustrates an example of a PAP system with basic controls, e.g., a Hi/Low pressure control/toggle 260 located on the PAP device 220 and an On/Off control 281 provided to the quick disconnect 280 of the air delivery tubing. The PAP device may also include an automatic ramp feature, an overheating motor shut-off, and/or a motor overheat LED indicator.

5.2 Basic Controls, Comprehensive Feedback Online

In an example, the PAP system may include basic controls with comprehensive feedback provided to the patient online. The basic controls on the PAP device keep daily use simple, and comprehensive information online keeps the patient engaged.

FIG. 6 illustrates an example of a PAP system with basic controls, e.g., Hi/Low pressure control/toggle 61 and On/Off control/button 60 provided to PAP device 20. The PAP device may also include electronics to monitor and collect relevant data, a USB stick 65 to transfer data, an automatic ramp feature, an overheating motor shut-off, and/or a motor overheat LED indicator. Also, online service may be provided to track and provide feedback to the patient.

5.3 Basic Controls, Essential Feedback on PAP Device

In an example, the PAP system may include basic controls with essential feedback provided on the PAP device, e.g., via graphical display provided to the PAP device. The simple controls and graphical feedback help the patient understand the therapy and stay motivated.

FIG. 16 illustrates an example of a PAP system with basic controls, e.g., controls 360 providing Hi/Low pressure control/toggle and On/Off control/button provided to PAP device 320. The PAP device may also include electronics to monitor and collect relevant data, low resolution backlit Liquid Crystal Display (LCD) to display feedback, and/or overheating motor shut-off. Additional controls or settings may include a wake-up alarm (e.g., wakes with breathing pattern).

6. Additional Examples of PAP Systems

FIGS. 19-42 illustrate additional examples of PAP systems, including additional examples for wrapping headgear straps and/or covers around the patient's head, supporting the PAP device on or adjacent the patient's head, covering the patient's faces with bandana-like covers, and/or directing air delivery tubing along the patient's head. One or more examples may be configured in view of heat comfort, ease of putting on/off, strap size and location, proportion, and/or part break. In addition, one or more examples may be configured in view of material qualities, color, details, human proportion, visual size, and/or gender neutrality.

FIGS. 19, 29 and 30 illustrate PAP systems having a bandana type arrangement such that a material cover 3001 is located over the patient interface to shield, protect or conceal a patient's nose and mouth and the patient interface. Different lengths of the material cover 3001 may be provided as indicated in FIGS. 19, 29 and 30. FIG. 19 shows the arrangement of the material cover 3001 when a patient is upright and FIGS. 29 and 30 show the arrangement of the material cover 3001 when a patient is lying down.

FIGS. 20, 21 and 37 show different examples of a textile cover 3101 that is configured to cover and wrap into the headgear. FIG. 20 shows a close fitting textile cover 3101 and FIGS. 21 and 37 show looser textile covers 3101. The air delivery tube runs within the textile cover. This arrangement assists in disguising the medical looking features of the system and makes the system appear as an all one unit rather than multiple components joined together. The button 3101-1 on the textile cover may assist with providing a non-medical or softer look and feel of the system. The button may also comprise both the vent for the patient interface and the attachment mechanism for the patient interface. FIG. 26 illustrates the arrangement of the textile cover 3101 when the patient in lying down. The air delivery tube, patient interface and PAP system are all located within the textile cover to provide the appearance of a single complete system.

FIGS. 22 and 28 illustrate an example with the PAP device 3201 located on a top portion of a patient's head. The PAP device, patient interface and air delivery tube are each located within or under a cover to give an overall look of an all-in-one or complete single system. The cover may also reduce the medical look of the system and/or hide, veil or conceal the connection points between the different components of the system, such as the patient interface, air delivery tubing and PAP device connection points. The patient interface may include nasal pillows, a nasal cradle, nasal prongs or a nasal cushion. FIG. 27 illustrates a similar example with the PAP device located on top of the patient's head and including a nasal cannula as the patient interface.

FIG. 23 illustrates another head worn arrangement wherein the PAP device and cover 3301 are wrapped around the forehead rather than on top of the head.

FIG. 24 illustrates an exemplary PAP system wherein the PAP device 3401 is configured to swing or suspend from the head and may rest against the chest when the patient is in the supine position. The air delivery tubing is located within the textile cover 3402 that wraps around the top of the head and connects to the patient interface strap 3403 wrapped across the face.

FIG. 25 illustrates a similar PAP system arrangement to that shown in FIGS. 9-10, with a slightly different headgear strap arrangement. The headgear strap portion 3501 is structured to wrap along the cheek region and up over the top of the patient's head and also include a supporting strap 3502 structured to wrap below the ears, and around the back of the patient's head or neck region.

FIG. 31 illustrates a PAP system arrangement having a wrap arrangement 3601 configured to provide predominantly under-the-ear vectors to support the patient interface and air delivery tubing that are supported in or under a textile cover. Further headgear straps 3602 that extend over the top of the head assist in supporting or holding the interface up against the patient's face or nose.

FIG. 32 illustrates a PAP system arrangement including a headgear strap 3701 that is structured to wrap across the face above the upper lip and below the nose and under the patient's ears to support the patient interface against the face. A further strap 3702 extends over the ears to assist in maintaining and sealing the patient interface in position against the nasal region.

FIG. 33 illustrates a PAP system arrangement wherein the air flow is routed through an air delivery tube or conduit 3801 located within the headgear system.

FIGS. 34 and 35 illustrate PAP system arrangements having a PAP device 3901 positioned on or in a strap across the patient's forehead or in a forehead support. As shown in FIG. 34, the PAP system may include an inlet filter 3901-1 on the front of the device to provide clean air. Such an arrangement may also be suitable for providing purified air to treat conditions such as asthma, allergies, etc. Alternatively, a brand or logo 3901-2 may be printed on the front of the device as indicated in FIG. 35. The patient interface may also include a vent on the outer surface.

FIG. 36 illustrates an example of a forehead strap 4001 positioned across the patient's forehead to provide support for a PAP device located at the back of the head. The forehead strap also supports side and top straps in position to assist in maintaining the patient interface in position against the patient's face or nose.

FIGS. 38, 39 and 40 illustrate PAP system arrangements having air delivery tubing 4101 coupled to the patient interface and arranged within the headgear straps. The length of the patient interface portion and where it connects to the air delivery tubing in the headgear differs between these different arrangements. FIG. 40 shows a small patient interface portion 4102 that is predominately located under the nose. FIG. 39 shows a slightly larger patient interface portion 4102 that extend across the cheek region prior to coupling to the air delivery tubing. FIG. 38 shows a large patient interface portion 4102 that extends up adjacent the ear region prior to coupling to the air delivery tubing. As shown in FIG. 40, a clear window 4102-1 may be provided at the front of the patient interface portion to allow visibility of the nostrils when in use.

FIG. 41 illustrates a PAP system arrangement having a head band strap 4201 that is configured to support the air delivery tubing 4202, e.g., by having strap portion to hold a portion of the air delivery tube on the head band to assist in maintain the system in position on the head and face.

FIG. 42 illustrates a PAP system arrangement having a PAP system located within a cover 4301 on the head and air delivery conduits are located within a cover together with the PAP device. A clear window 4302 may be provided under the patient interface to allow visibility of the nasal region.

It is noted that all of the examples described above may be formed of a clear silicone, elastomeric material to allow visibility and appear less visible on the face. Alternatively, each of the examples may be formed from a textile material or a combination of a textile material to provide a less medical and less obtrusive look as described in more detail herein.

In an example, the positioning of the PAP device relative to the patient's head may at least partially determine a size of the air delivery tube. For example, an increased distance of the PAP device from the patient's nose may result in an increased diameter of the air delivery tube. In an example, a PAP device positioned about 50 cm to 80 cm, such as 60 cm or 70 cm, from the patient's nose (e.g., maximum distance) will result in an air delivery tube having a diameter of about 10 mm to 20 mm, such as 15 mm.

Figure 43:
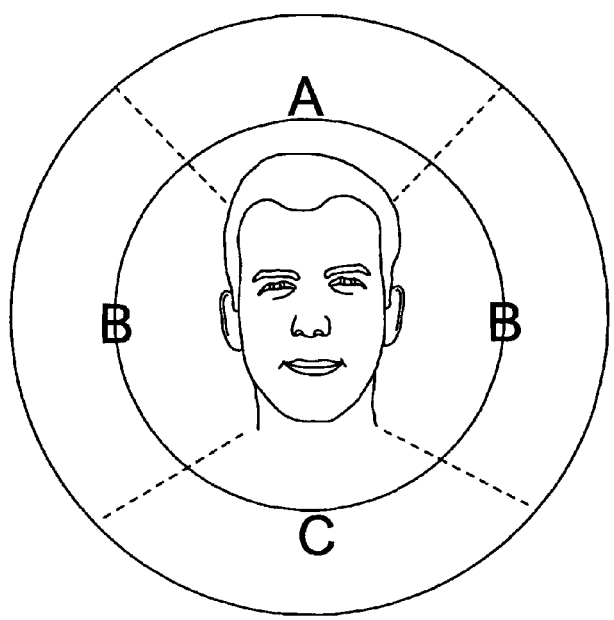
FIG. 43 is a schematic view showing exemplary zones for positioning a PAP device relative to the patient's head according to an example of the present technology.

As shown in FIG. 43, a PAP device positioned in Zone A may be preferred for comfort and functioning of the PAP device. Zone B may be more preferable than Zone C to provide a smaller system with a reduced tube diameter.

7. Alternative Examples

The following provides alternative examples of wearable PAP systems.

7.1 Flow Generator Appears Invisible

In an example, a video camera or image recording device may be attached or otherwise provided to a first side of the PAP device, and a screen or output device may be provided on another side of the PAP device. The image recording device may record the image that is directly in front of it, and display the recorded image on the output device. In an example, the output device is provided on an opposite side of the PAP device to the image recording device.

For example, the image recording device may be pointed or directed to the wall, which results in the output device displaying an image of the wall. This display may allow the PAP device to appear more invisible as the patient will only see an image of the wall.

7.2 Small PAP Device without a Motor

In an example, air may be pressurized by electrically stimulating the air.

For example, a textile conduit may be electrically stimulated to pulse, or relax and contract (similar motion to peristalsis), so it is like a textile muscle. By varying the diameter of the conduit, it will force air to travel towards a patient end of the conduit and pressurize the air. The textile conduit may also include one or more valves that may periodically open and close to aid in the buildup of pressure.

In an example, a pair of pistons may be positioned at each nostril within a cylinder, each piston driven by a drive structure (e.g., connecting rod and crank) to cause the piston to move up and down. As the pistons move up they force air into the patient's nose. The speed of the piston will dictate the pressure delivered to the patient's nose. Each piston may be connected such that as one piston moves up and forces air into the patient's airways, the other piston retracts and the cylinder refills with air. Alternatively, the pistons may not be connected and run either in sync or out of sync.

7.3 Small PAP Device with a Motor

Figure 44:
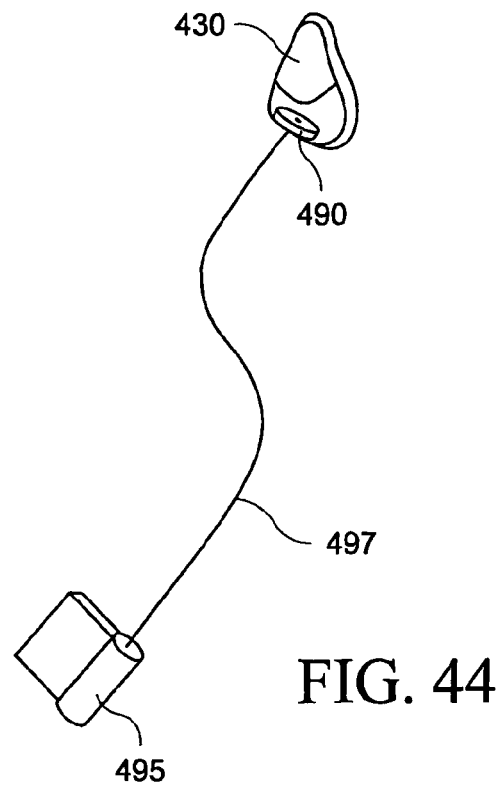
FIG. 44 is a schematic view of a PAP system according to another example of the present technology.

As shown in FIG. 44, an impeller 490 may be provided to the patient interface or mask 430 which is driven by a motor 495 (e.g., battery powered) coupled to the impeller 490 by a twist drive or snake drive 497, i.e., cable-like drive shaft.

7.4 "Smart" Tube

In an example, the air delivery tube may be configured to follow the movements of the patient in use, i.e., smart tube. For, example, the tube may include one or more sensors configured to sense movement of the patient and an adjustment device configured to automatically adjust the position of the tube to compliment the patient's position. In another example, one or more magnets or electromagnets or other means of attraction may be used to allow the tube to follow movements of the patient, e.g., magnets embedded in the patient's bed clothes.

Figure 192:
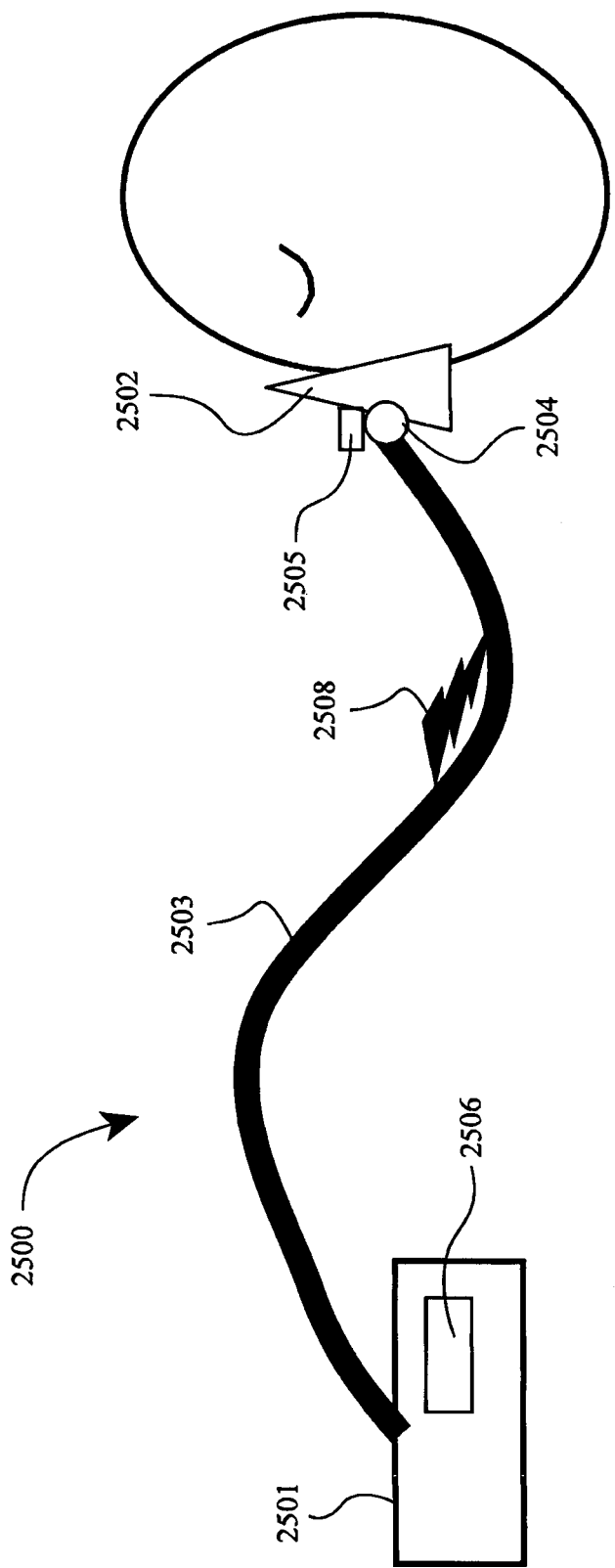
FIG. 192 is a schematic view of a system including an active tube or smart tube according to an example of the present technology.

FIG. 192 is a schematic view of a system 2500 according to an example of the technology. The system is structured to automatically position the patient interface optimally for the patient, and sense and respond to the patient in order to improve the overall sleep and therapy delivery experience for the patient. The system includes an active tube or smart tube structured to provide a force to the patient interface so as to push or seal the patient interface onto the patient's face, thereby performing the function of headgear. In examples, headgear is not provided or needed in the system although may be optionally provided to enhance stability and/or positioning of the patient interface. Removal of the headgear may reduce claustrophobia through removal of headgear surface area and forces on the patient's head.

The system looks and feels invisible to the user in that it performs the function of the headgear. In an example, the system may be structured to automatically fit the patient interface to the patient after the patient is asleep.

As illustrated, the system 2500 includes a base unit 2501 (including a blower for generating air at positive pressure), a patient interface 2502 adapted to engage the patient's face, and an active tube or smart tube 2503 to deliver the supply of pressurized air (e.g., 2-30 cm $H_2O$) to the patient interface and to create the correct interface force and angle to the patient's face. The patient interface or mask may have any suitable configuration as is known in the art, e.g., full-face mask, nasal mask, oro-nasal mask, mouth mask, nozzles, nasal prongs, nasal pillows, cannula, nasal cradle, etc. In an alternative example, the patient interface may be positioned adjacent to or near the patient's face and not specifically engaged. This arrangement may be provided, for example, to deliver treated air that has medical or health-giving benefits, e.g., purified air, air containing antioxidants or medication.

Figure 3:
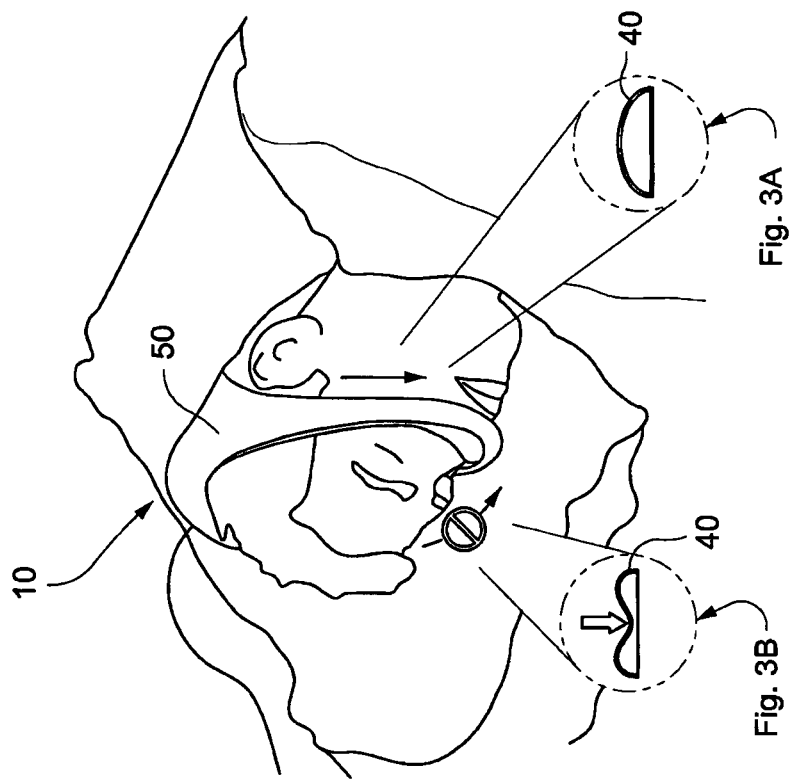
FIG. 3 is a side perspective view of the PAP system of FIG. 1 in use.
Figures 3, 141:
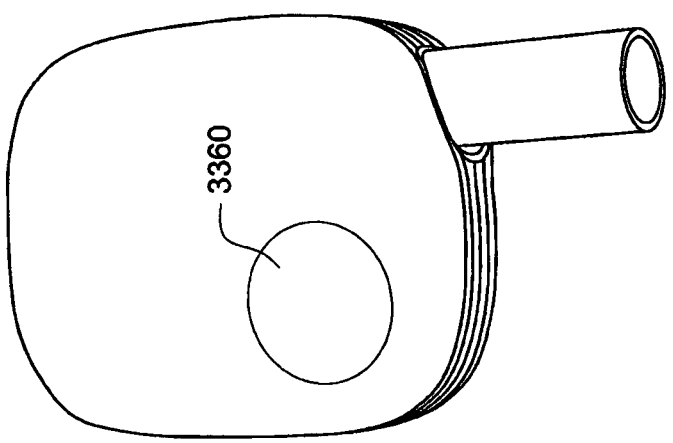
Figures 2, 141:
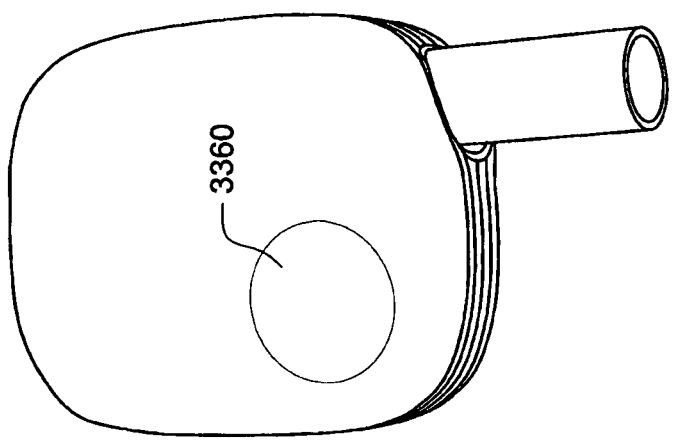
Figures 1, 141:
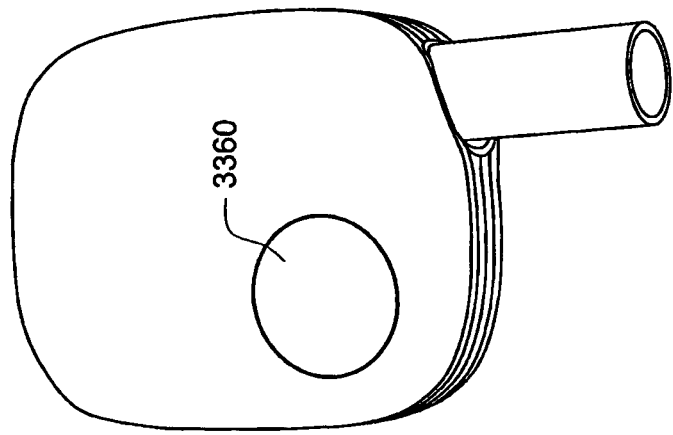

The active tube 2503 is structured such that it can modify its own shape in order to move the patient interface, modify the amount of force exerted between the patient interface and the patient and/or move/adjust its own positioning. In an example, as shown in FIG. 193-1, the active tube 2503 may include a series of active elements 2503-1 to adjust the length of the tube 2503-2. As illustrated, each active element 2503-1 includes at least one side that may be selectively contracted and/or extended in order to adjust the length of the tube. For example, as shown in FIGS. 193-1 and 193-2, one or both sides of selected active elements 2503-1 may be contracted in order to bend and hence shorten the length of the tube. Alternatively, one or both sides of selected active elements 2503-1 may be extended in order to straighten and hence extend the length of the tube as shown in FIG. 193-3. Such bending/straightening of the tube adjusts the lateral undulation and hence length of the tube, which adjusts the force provided to the patient's face by the patient interface provided to the end of the tube. For example, selective active elements may be contracted to shorten the lateral extent of the tube and hence reduce or relieve force provided to the patient's face, and likewise selective active elements may be extended to extend the lateral extent of the tube and hence increase or enhance force provided to the patient's face. The differential contraction or extension across the active elements may be achieved by piezo actuators for example, or by other suitable means. In certain arrangements, the force provided to the patient's face may be automatically adjusted based on a detected level of leak from the patient interface.

Figure 199:
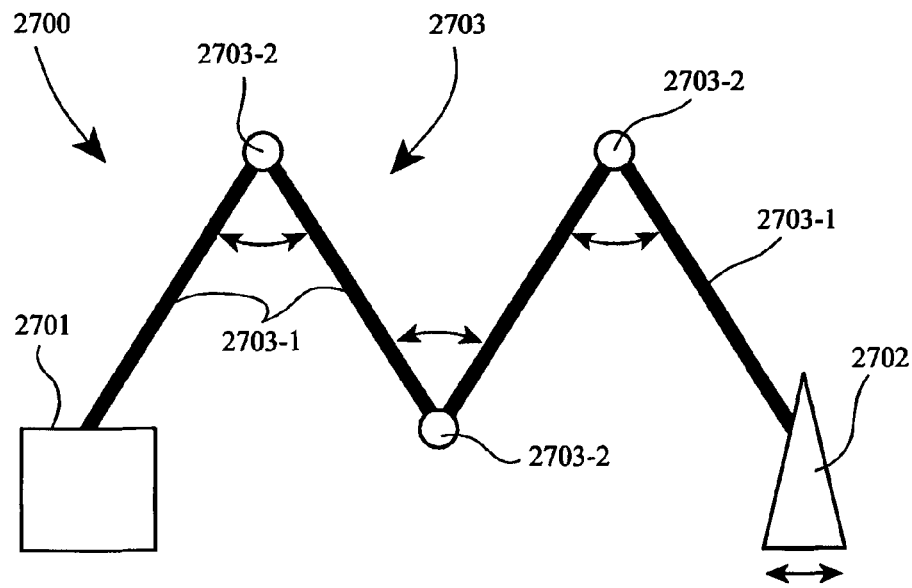
Figure 200:
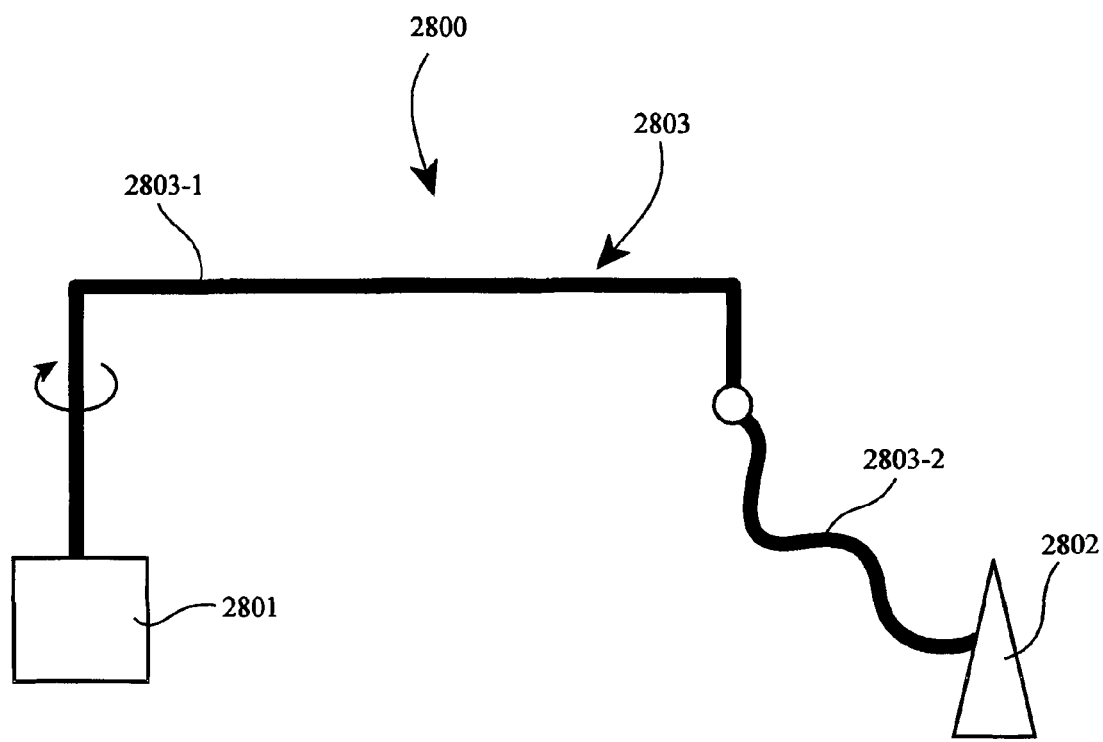

However, the length or shape of the tube may be modified in other suitable manners. For example, the length of the tube may be varied by linear motion, rather than differential bending of an S-like form as described above. FIG. 199 illustrates an example of a system 2700 including a base unit 2701, a patient interface 2702, and an active tube 2703 having a combination of straight or curved elements 2703-1 with pivots 2703-2 at their junctions. FIG. 200 illustrates an example of a system 2800 including a base unit 2801, a patient interface 2802, and an active tube 2803 having a combination of a large rigid element 2803-1 and a shorter selectively adjustable element 2803-2 similar to the active tube 2503 described above. In this arrangement, the element 2803-1 provides larger adjustments while element 2803-2 provides fine tuning, smaller adjustments.

The base unit 2501 provides a fixing point or base from which one end of the active tube is anchored for applying force to the patient via the patient interface. The base unit may be immovable via the use of mass, friction, attachment to a relatively stable object compared to the patient or to the patient's body, e.g., dead weight, clip to headboard of bed, etc. In an example, the base unit may be attached to the patient's body.

Figure 194:
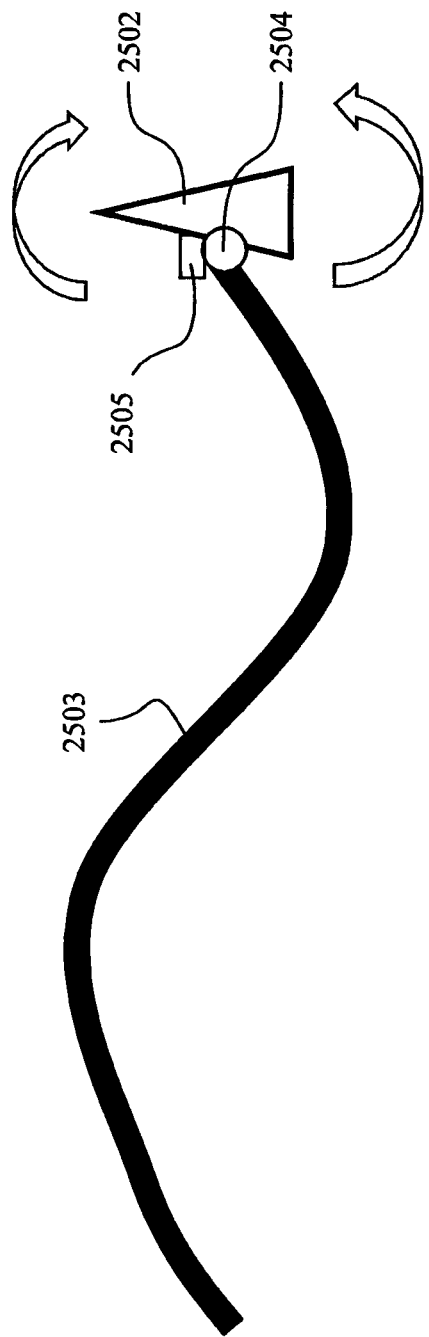
FIG. 194 is a schematic view showing an active tube, patient interface, and interface controller according to an example of the present technology.

An interface controller 2504 is provided to the patient interface 2502 to adjust the angle of the patient interface relative to the wearer, using the active tube 2503 as a steady base as shown in FIG. 194. A force sensor 2505 is provided adjacent the patient interface to measure the force and torque between the patient interface and the patient's face.

A controller or control module 2506 is provided to the base unit to monitor and control adjustment of the system so that the patient interface is optimally positioned for the patient for therapy. The control module receives and processes input signals, analyzes data, and sends commands to the active tube and interface controller. In an example, signal communication 2508 may be provided by wires integrated into the active tube or wireless elements, e.g., configured to send input signals from the force sensor to the control module, and send commands from the control module to the active tube and interface controller.

The control module receives data from the force sensor, data regarding the positioning of the tube, data regarding the patient's sleeping position, and/or data regarding the patient's breathing patterns in order to analyse the patient's activity and positioning and make adjustments to the patient interface for optimal treatment. At any given time, the control module knows: the position of the active tube relative to the base unit and the structural shape of the active tube (e.g., by assessing the position state of each of the active elements (i.e., contracted or extended) in the tube at any given time; force and torque between the patient interface and the patient at the end of the tube (e.g., measured by force sensor 2505); the sleeping position of the patient (e.g., interpreted from the shape of the tube and the angle of the patient interface relative to the tube, visual data by video or infrared sensing; and/or the breathing patterns of the patient.

In an example, the system may be configured to anticipate what patient movement is likely to come next, e.g., based on historical data analysis of sleep movement of the patient and the general population. For example, the control unit may record patient movement and store this data, and therefore build a "profile" of the patient's typical sleeping movements over a usage period. Over time, this data may be used to provide feedback to the patient, e.g., information whether any chosen period of sleep is typical or unusual, restless or peaceful. This profile data may be related to subjective data entered by the patient.

The control module is configured to recognize needs of the patient and improve performance of the system by sensing the magnitude of cushion seal force being applied and whether leak is occurring. The control module can use this information, e.g., to reduce force provided by the patient interface to the patient's face if it is unnecessarily high or to increase force provided by the patient interface to the patient's face if there is a leak. Further, the angle or force vector provided by the patient interface can be adjusted to provide an optimum seal/comfort level by responding to the location of the leak. In an example, leak location data may be provided by the patient interface and/or audio based leak sensing data. Also, the patient may intentionally set the interface angle and force to achieve desired effects such as more or less force in a specific region of the patient's face.

The example techniques discussed in preceding paragraphs above may be performed on or via a PAP or other computer device that includes processing resources including at least one processor or controller and a memory. These example techniques also may be implemented in any suitable combination of hardware, software, firmware, and/or the like. For instance, in software-based or software-inclusive implementations, a program or set of instructions, when executed using the processing resources of the PAP or other computer device, may be configured these and/or other steps to be carried out.

Figures 1, 195:
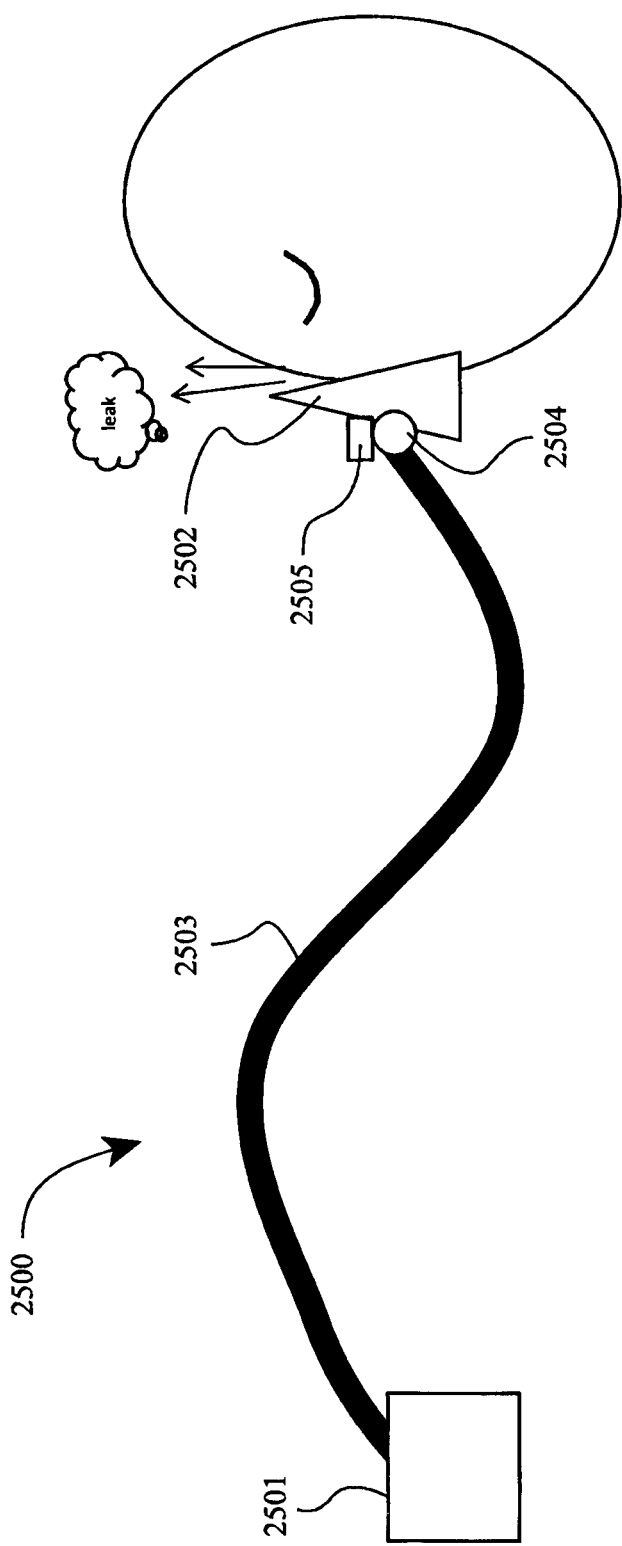
Figures 2, 195:
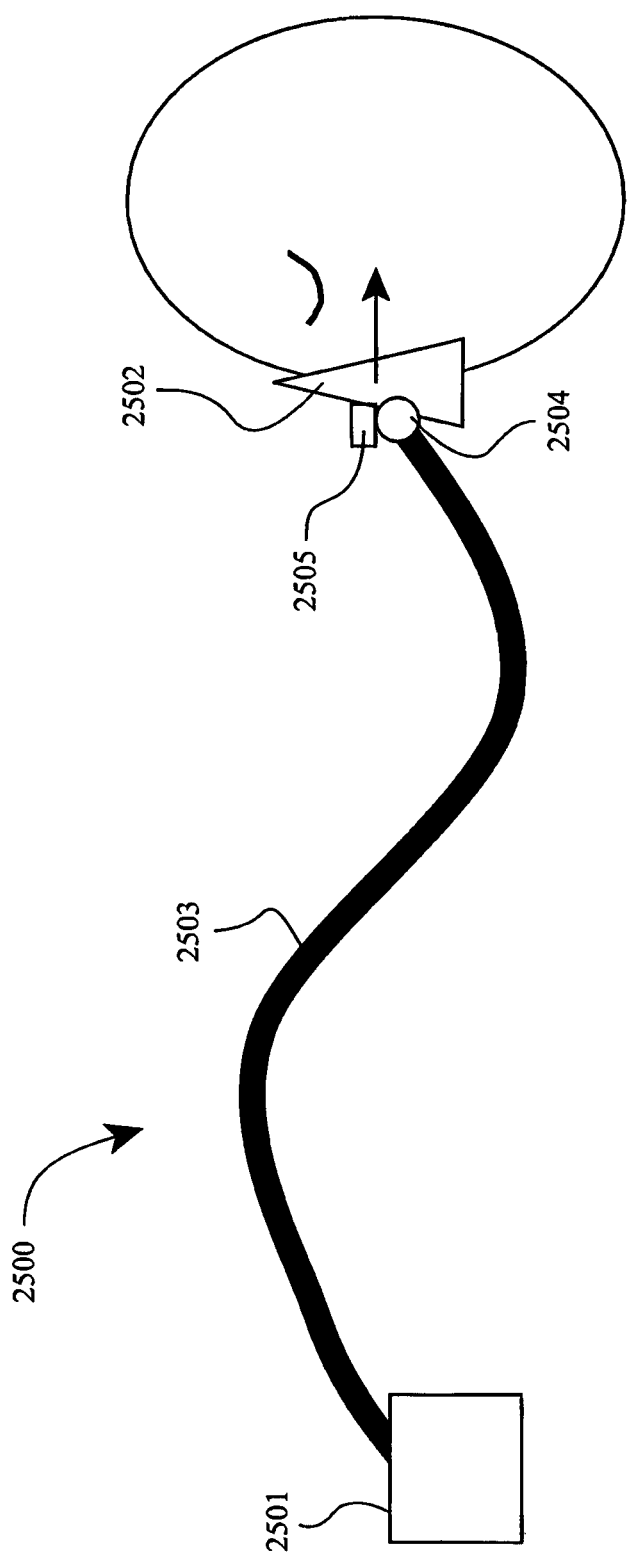
Figures 3, 195:
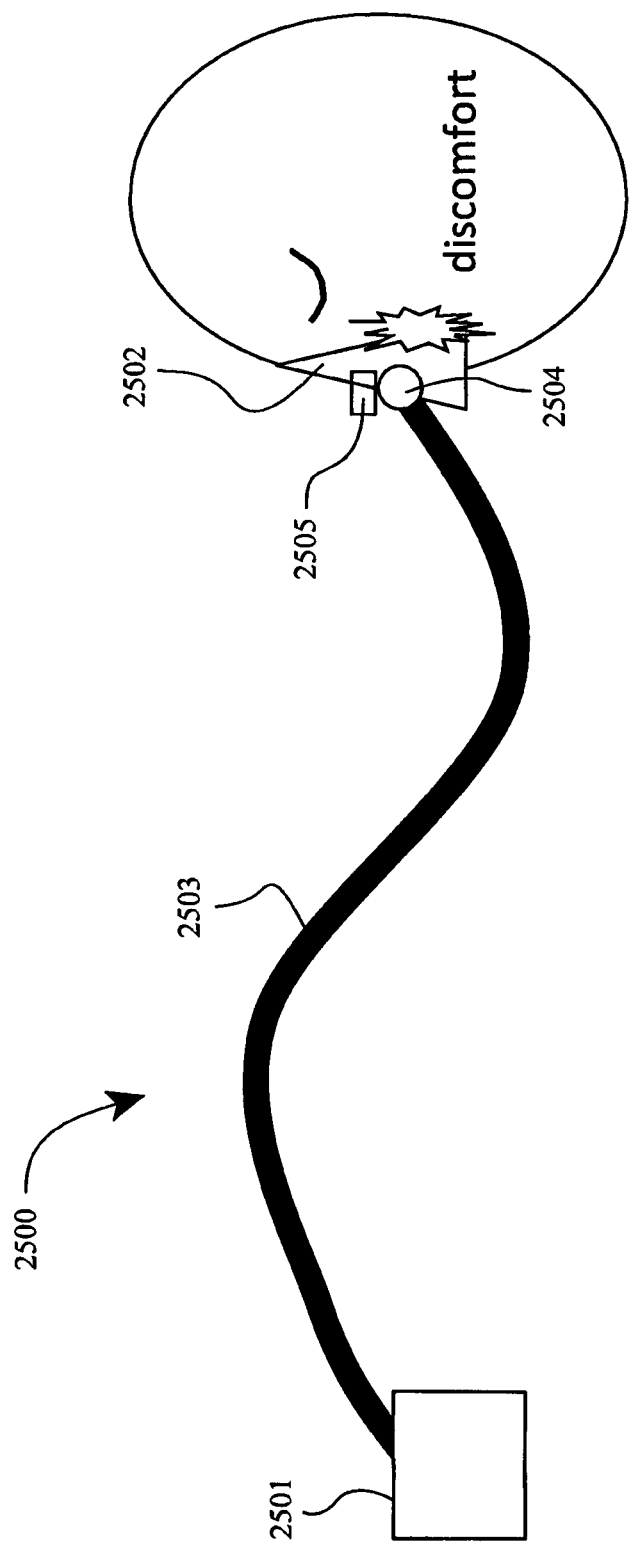
Figures 4, 195:
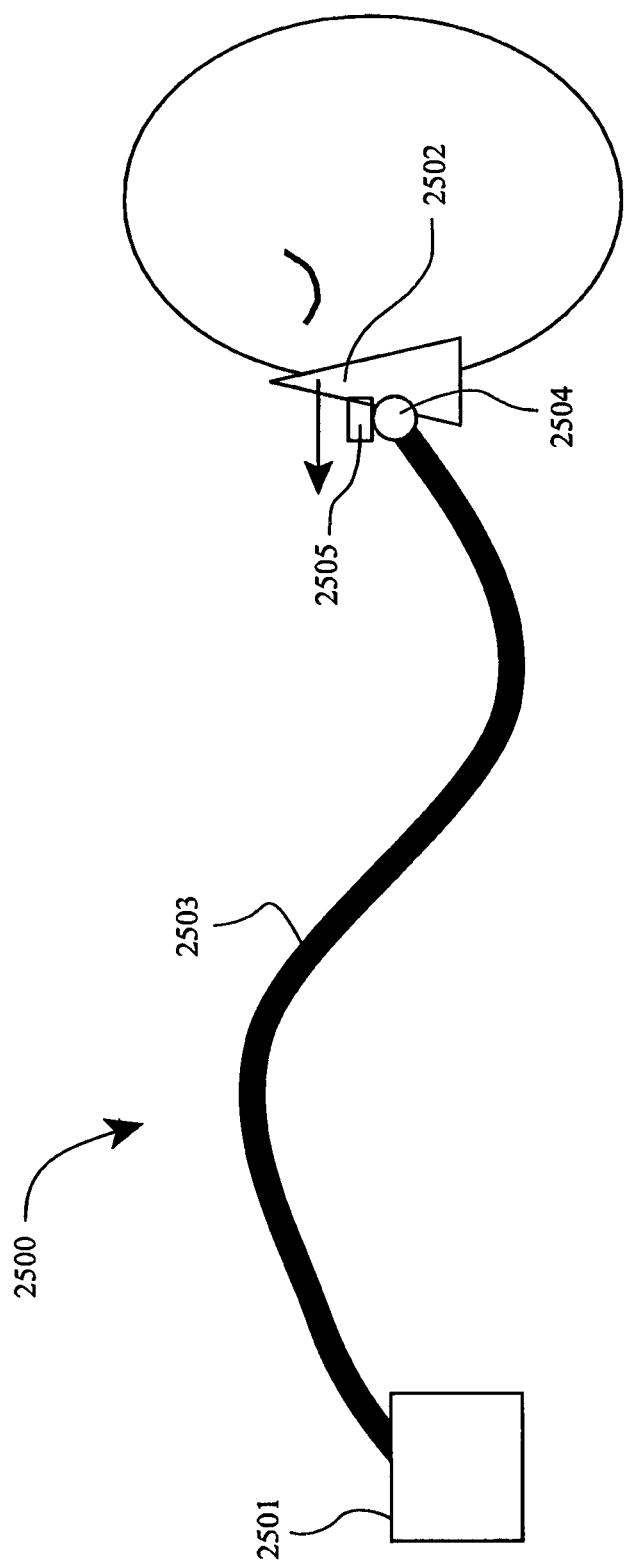

FIGS. 195-1 to 195-4 show an example of the system adjusting the total force applied to the patient's face by the patient interface in response to leak or patient discomfort. For example, FIG. 195-1 shows a leak between the patient interface and the patient's face and FIG. 195-2 shows the system increasing the force applied to the patient's face (e.g., by modifying the active tube) to stop the leak. Likewise, FIG. 195-3 shows a discomfort between the patient interface and the patient's face and FIG. 195-4 shows the system decreasing the force applied to the patient's face (e.g., by modifying the active tube) to ease the discomfort.

Figures 1, 196:
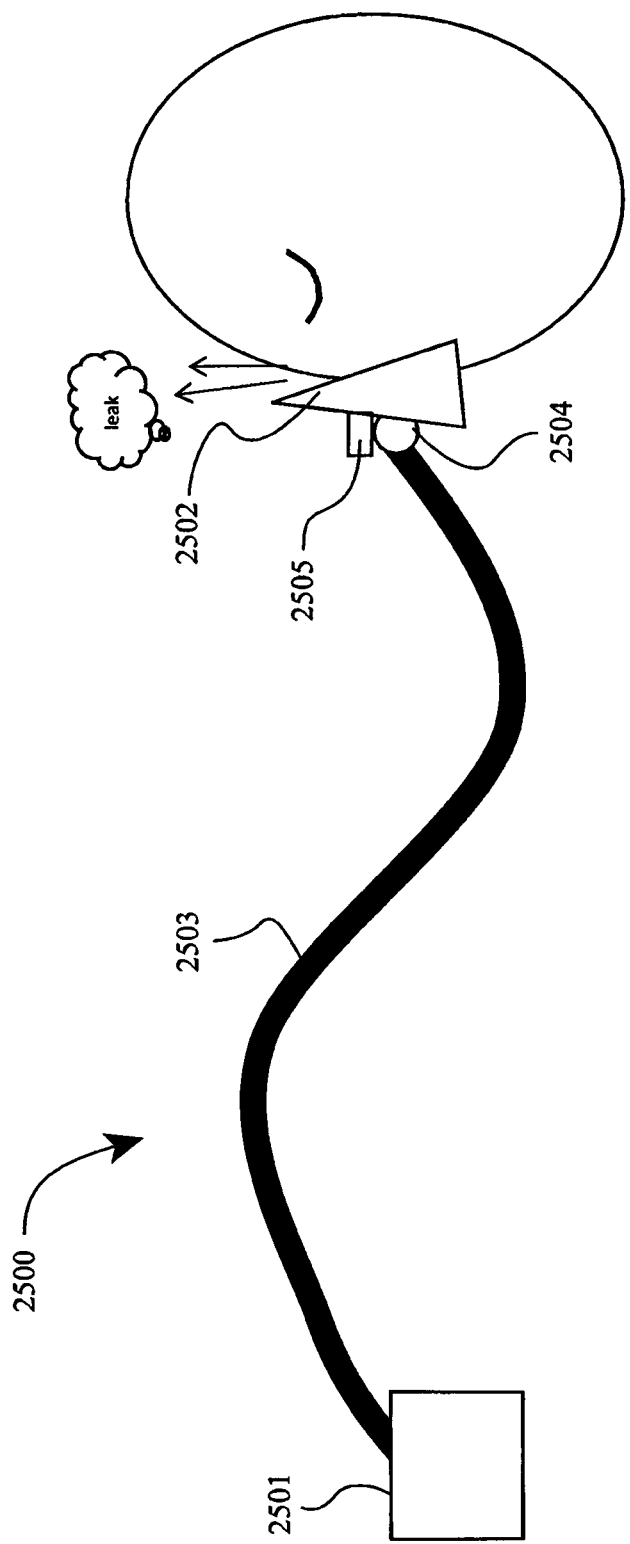
FIG. 1 is a front view of a headworn PAP system according to an example of the present technology.
Figures 2, 196:
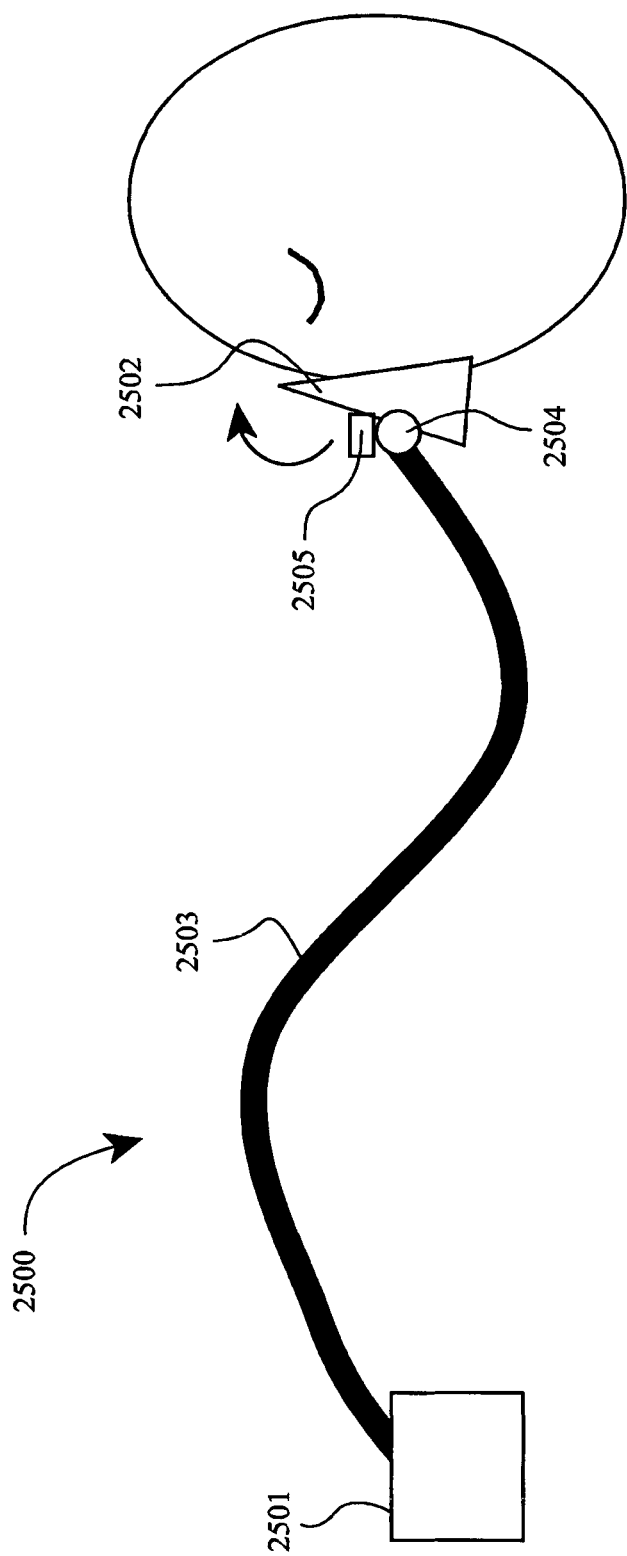
FIG. 2 is a side view of the PAP system of FIG. 1.
Figures 4, 196:
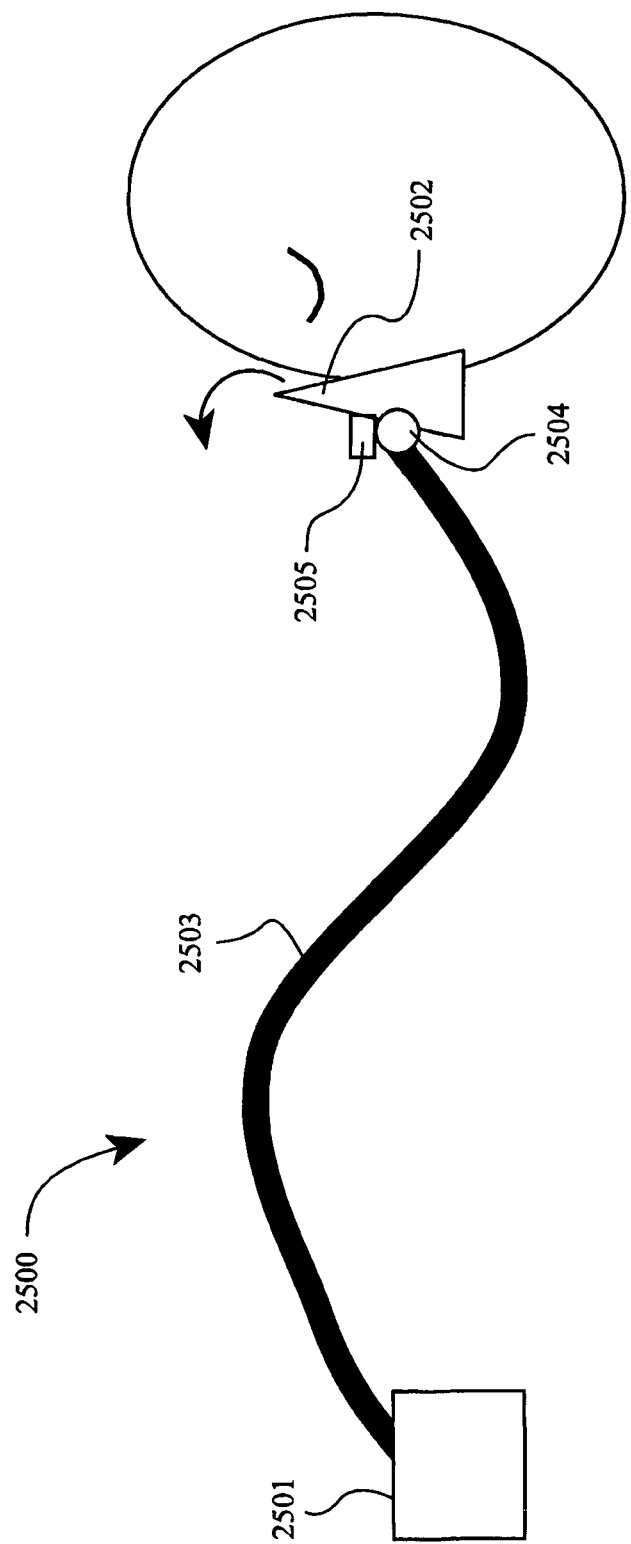

FIGS. 196-1 to 196-4 show an example of the system adjusting the force angle applied to the patient's face by the patient interface in response to leak or patient discomfort. For example, FIG. 196-1 shows a leak between the patient interface and the patient's face and FIG. 196-2 shows the system adjusting the angle of the patient interface relative to the patient's face (e.g., via the interface controller 2504) to stop the leak. Likewise, FIG. 196-3 shows a discomfort between the patient interface and the patient's face and FIG. 196-4 shows the system adjusting the angle of the patient interface relative to the patient's face (e.g., via the interface controller 2504) to ease the discomfort.

In FIGS. 195-1 to 196-4, the system provides an adaptive system that allows the patient interface to acquire an optimum fit (by adjusting force and/or torque) between the patient interface and the patient by making real-time changes based on the movement of the user and changes in leak and comfort. Such arrangement improves comfort for the patient by reducing mask force to the minimum required at any point in time (e.g., satisfactory seal and comfort) and responding automatically to leak events.

In an example, the system may allow the patient interface to move in response to or anticipation of the patient sleep movements, thereby exerting no tube drag by "following" the patient. For example, the system adapts or responds to patient movement by adjusting the force and/or torque (e.g., by modifying the active tube and/or interface controller) provided by the patient interface to the patient to follow the patient movement for optimal fit and comfort. Such arrangement improves stability of the patient interface because of reduced tube drag and enables less obtrusive patient interfaces that usually fail due to poor stability.

Figures 3, 197:
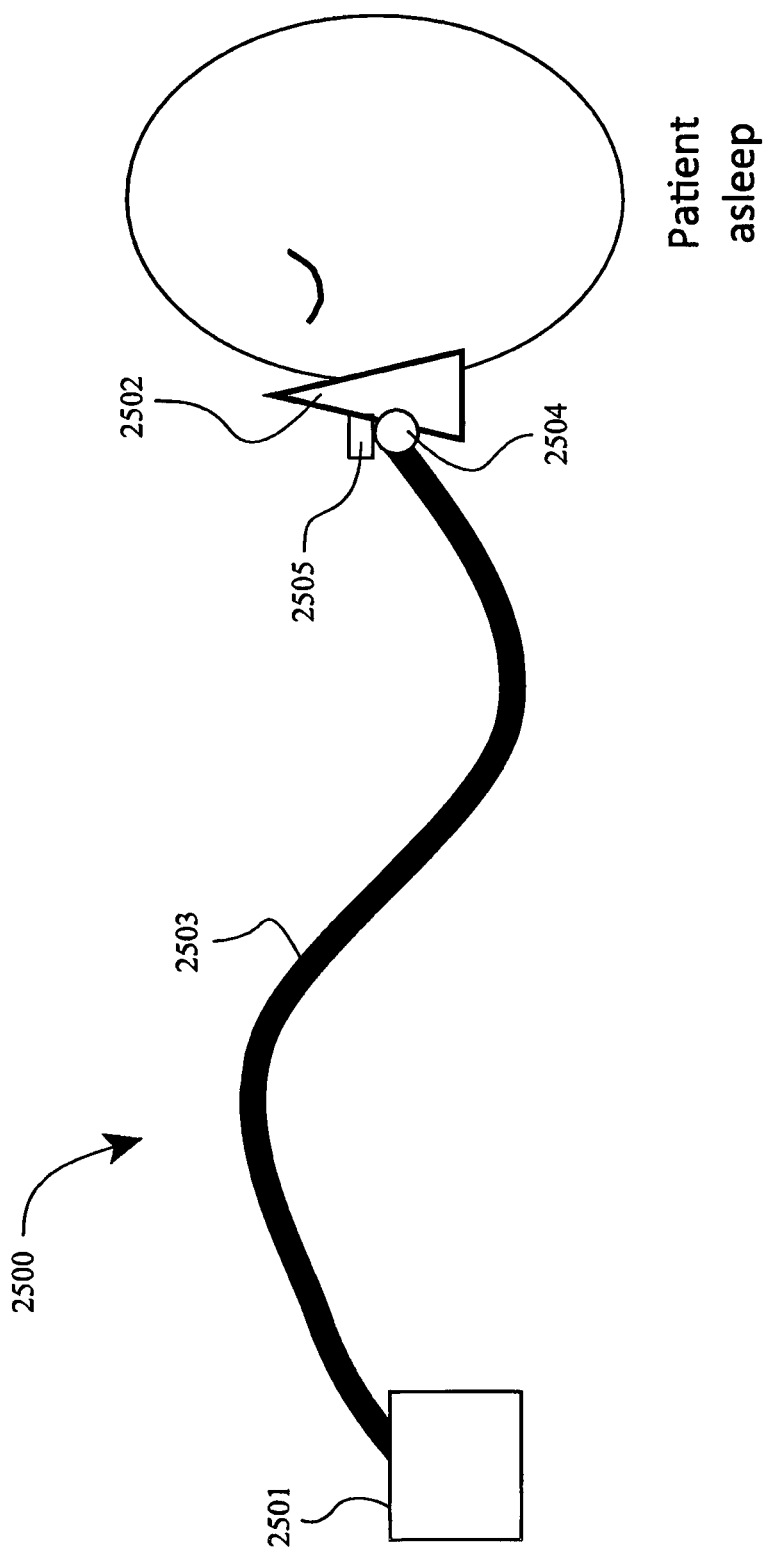

FIGS. 197-1 to 197-3 show an example in which the system allows the patient to fall asleep without having to fit the patient interface, and the patient interface automatically locates the patient's face and fits itself after a time delay, i.e., system adapted to fit itself to the patient while the patient is unaware or asleep. For example, FIG. 197-1 shows the patient awake with the patient interface disengaged from the patient, FIG. 197-2 shows the patient asleep with the patient interface still disengaged from the patient, and FIG. 197-3 shows the patient interface automatically located and engaged with patient following a time delay, e.g., predetermined period of time following acknowledgement that the patient is asleep. Such arrangement allows the patient to fall asleep more naturally, thereby making therapy essentially invisible to the patient and their bedpartner. Also, such arrangement allows greater compliance through improved bedtime experience and attractiveness of the system to the patient and bedpartner, e.g., allows patient to fall asleep reading a book. In an example, the patient could override the automated fit system.

In an example, the patient may wear a sticker or marker in a specified location on the face to allow the patient interface to automatically locate the patient's face in use. The marker may alternatively be located in a simple strap, band, or headgear that is worn by the patient. The sticker or marker may include a small device configured to emit a signal, emit a magnetic field, and/or display a distinctive shape that may be identified by a corresponding receiver on the patient interface. This information may be combined with the shape of the tube to allow the control module to determine the location of the patient.

Alternatively, the patient could position the interface in the correct position on the face and record this position by a push button or similar method on the base unit. The base unit could monitor subsequent changes in patient face location via infra-red or similar positional sensing methods. Once the interface is ready to be moved to the face, the system would compute where to locate the mask, based on the combination of the initial recorded location, plus any subsequent movement detected.

Figure 198:
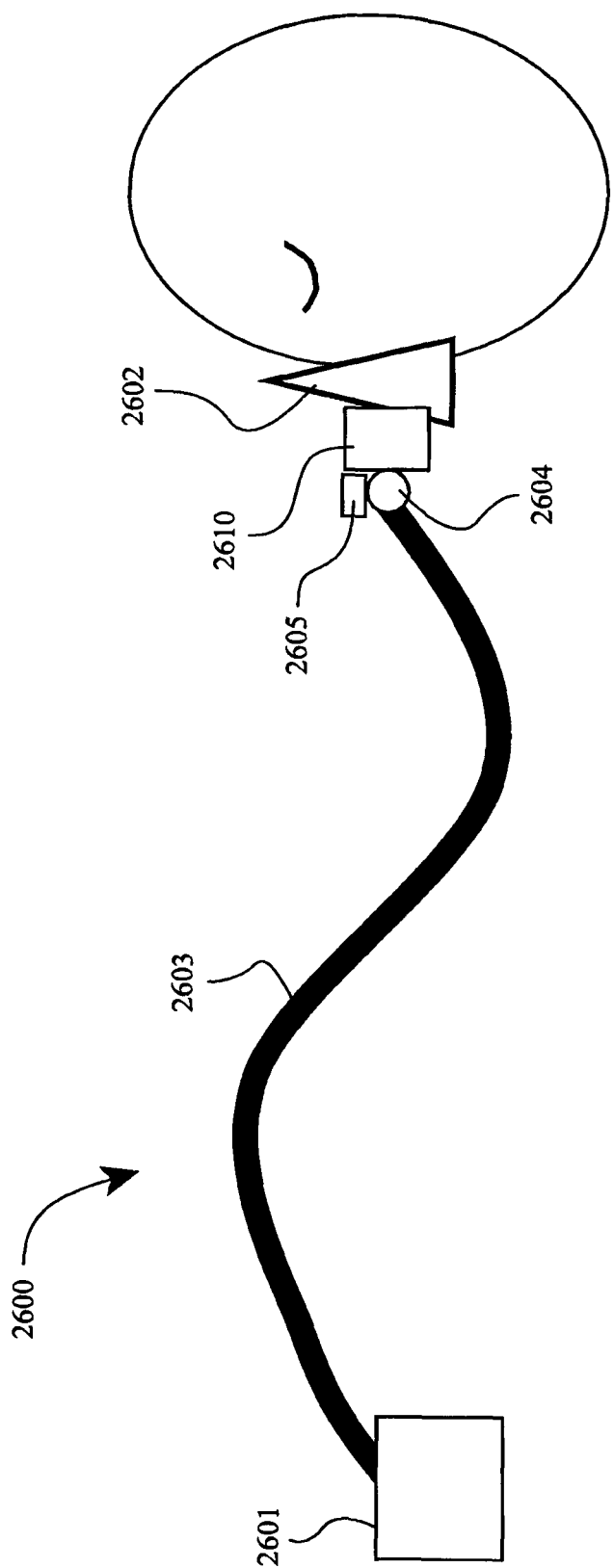

In an alternative example, the base unit may not include a blower for generating air at positive pressure. For example, as shown in FIG. 198, the system 2600 includes a stable base unit 2601, a patient interface 2602, a blower 2610 provided to the patient interface, and an active tube 2603 to move the patient interface/blower to adjust force, angle, and/or positioning of the patient interface/blower. In this example, the active tube is not a conveyer of pressurized air, but rather a positioning mechanism for the patient interface/blower. An interface controller 2604 and force sensor 2605 as described above may be provided to the patient interface/blower to adjust the angle and measure force/torque.

7.5 Neck Brace

In an example, a neck brace may be provided to fit around the patient's neck and to support the patient's chin so as to increase and maintain the distance between the patient's chin and chest. This arrangement increases the size of the patient's airway. The neck brace may apply force to the bony part of the chin or to the softer skin under the chin and closer to the neck (e.g., this may also push the tongue closer to the front of the mouth).

7.6 Bed Clothes

In an example, one or more portions of the patient's bed clothes may be constructed of inflatable bladders, such that if an airway obstruction is detected, one or more bladders of the bed clothes may inflate to thereby roll the patient on their side or front to aid in opening the patient's airway.

7.7 Power for the PAP System

In an example, power for the PAP system may be generated by kinetic energy from the patient's movements during sleep. Alternatively, the PAP system may be powered by heat or other chemical reaction from the patient.

7.8 Magnets

In an example, an impeller driven by magnets may be supported in the frame of the patient interface or mask. The mask frame may have magnets around the impeller cage, and the impeller may have opposing magnets on one or more of its impeller blades. The opposing magnetic force between the frame and the impeller may drive the impeller.

7.9 Mini Blowers

In an example, a series of relatively small blowers may be connected together to generate the supply of pressurized breathable gas.

7.10 Compressed Air

In an example, a cooled can of compressed air may deliver sufficient pressurized air to a patient, e.g., for one night. The can may be connected to a patient interface or mask for therapy delivery.

7.11 Ear Plugs

In an example, ear plugs may be configured to create a pressure differential in the patient's ear canal. The ear plugs may trigger the pressure differential if an airway obstruction is detected. This creates a sensation whereby the patient will want their ears to "pop". This may trigger the patient to swallow in order to equalize the pressure, thereby opening the airway.

7.12 Distal Inlet for PAP Device

In an example, wearable PAP systems worn on the body (e.g., strapped around the patient's chest) may be covered by blankets and/or other bed clothes when in use. Accordingly, the PAP device should include an inlet that is distal or remote from the PAP device to ensure such inlet is not obstructed or impeded by the blankets/bed clothes in use.

For example, as shown in FIG. 45, the PAP device may include an elongated inlet tube 525 having a first end 525(1) attached to the inlet of the PAP device 520 and a second end 525(2) adapted to be positioned outside the blankets/bed clothes (e.g., outside of the bed or over the headboard) to receive air. As illustrated, the second end of the inlet tube may have an inlet filter 527 to remove particulates (e.g., corn-cobb-like filter including multiple relatively little filters in a cage-like arrangement, which provides adequate flow if partially blocked).

In the illustrated example, the PAP device and inlet tube may be enclosed by a cover or wrap 550, e.g., soft textile. At least a portion of the cover may be diffuse, e.g., portion surrounding the second end 525(2) and inlet filter 527 of the inlet tube.

In the illustrated example, the PAP device 520 may include a LCD display 560 and one or more control buttons 561, e.g., power button.

In an alternative example, the PAP device may be supported within a pocket provided to the patient's bed clothes. For example, one or both shoulders of the patient's bed clothes may include a pocket.

In an example, the minimum distance between the PAP device (e.g., inlet tube) and the patient's head is no longer than a typical necklace length.

7.13 Blower Behind the Pillow

In an example, as shown in FIGS. 46, 47, and 48, the blower (enclosed by cover portion 650(1)) is positioned above and/or behind the patient's pillow, e.g., behind and at least partially below a central portion of the patient's pillow. Such position of the blower may least encumber natural sleep. For example, this positioning or orientation of the blower keeps the air delivery tubing (enclosed by cover portion 650(2)) away from the patient's neck, allows for easy side-to-side turning, and works best for stomach and back sleepers. The behind-the-pillow orientation also works best for hiding the device, e.g., patients may prefer to keep or hide the blower under or behind the pillow when not in use.

In an example, the blower and/or the cover portion enclosing the blower may include a retaining structure (e.g., clip structure) to maintain the blower in position with respect to the patient's pillow. For example, FIGS. 49-1 to 49-6 illustrate alternative examples for retaining structures. In FIG. 49-1, the blower 620 includes a resilient clip structure 690-1 structured to grasp an edge of the pillow to maintain the blower in position. In FIG. 49-2, the blower 620 includes a resiliently pivotal clip structure 690-2 structured to grasp the edge of the pillow. In FIG. 49-3, the blower 620 includes a clip structure 690-3 with magnet portions structured to magnetically retain the pillow via a magnet provided to the edge of the pillow. In FIG. 49-4, the blower 620 includes a resilient and arcuate-shaped clip structure 690-4 structured to grasp the edge of the pillow. In FIG. 49-5, the blower 620 includes a over-center clip structure 690-5 to grasp the edge of the pillow. In FIG. 49-6, the blower 620 includes a roller arrangement 690-6 including upper and lower rollers that cooperate to grasp or bite the edge of the pillow.

Figure 156:
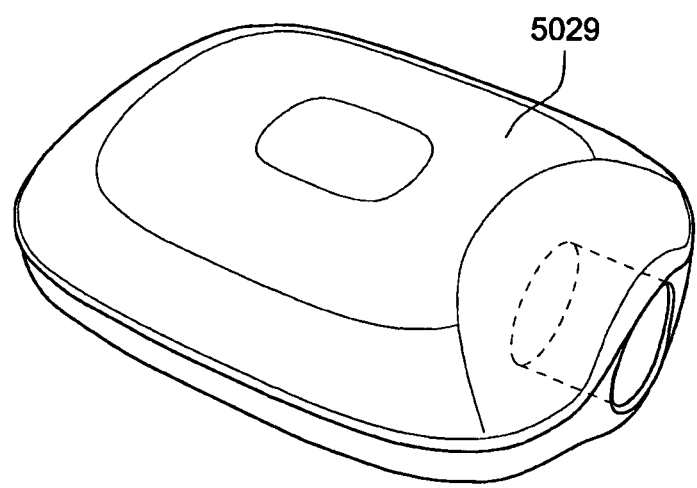
FIG. 156 shows an outer casing for a PAP device according to an example of the present technology.
Figure 157:
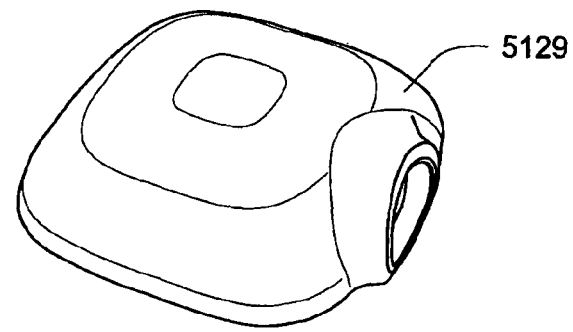
FIG. 157 shows an outer casing for a PAP device according to another example of the present technology.
Figure 158:
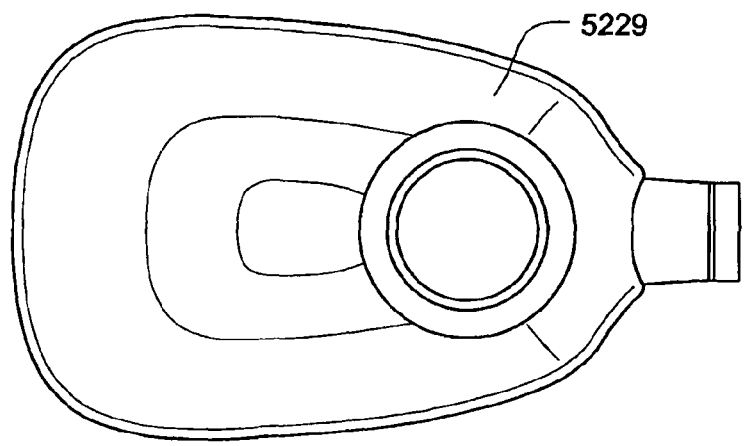
FIG. 158 shows an outer casing for a PAP device according to another example of the present technology.
Figure 159:
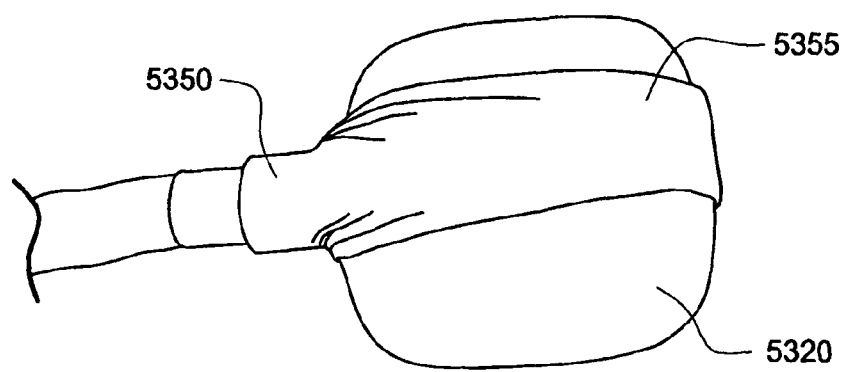
FIG. 159 shows a PAP system with a cover according to another example of the present technology.
Figure 160:
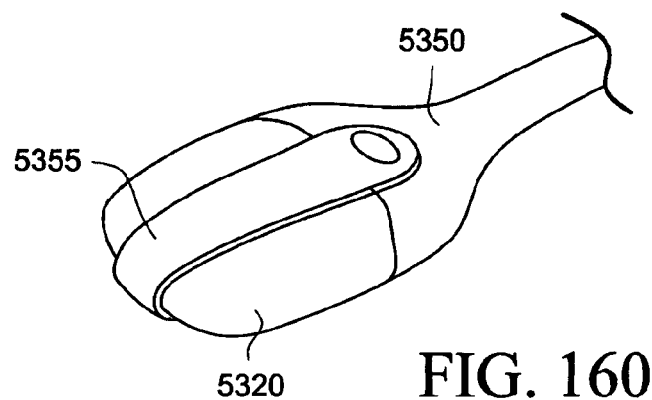
FIG. 160 shows a PAP system with a cover according to another example of the present technology.
Figure 161:
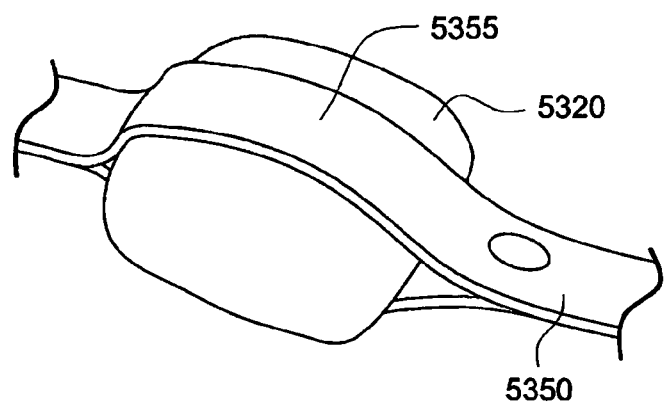
FIG. 161 shows a PAP system with a cover according to another example of the present technology.
Figure 162:
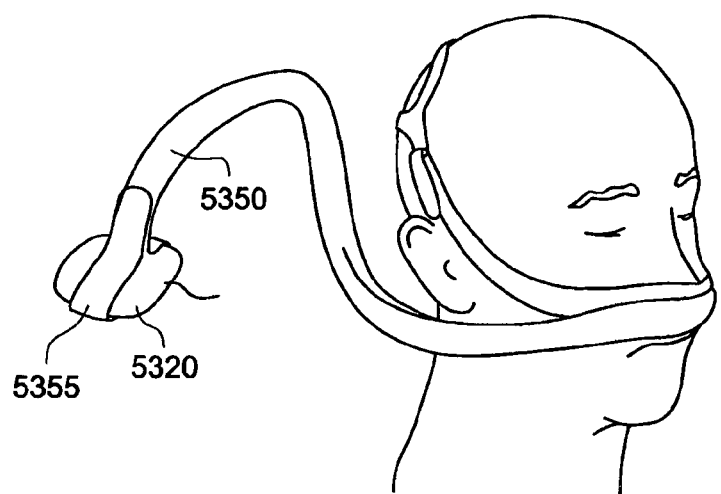
FIG. 162 shows a PAP system with a cover according to another example of the present technology.

In an example, the thickness of the outer casing of the blower or PAP device may be relatively thin to enhance comfort when the blower is positioned under the pillow in use. Also, in an example, the height of the outer casing of the blower or PAP device may be selected so that when the blower is positioned against the headboard in use, the display and on/off button are easily accessible. FIGS. 156 to 158 illustrate outer casings 5029, 5129, 5229 for a PAP device according to alternative examples of the present technology. FIG. 156 illustrates a PAP device having a generally rectangular shaped outer casing 5029 having curved surfaces and rounded edges. FIG. 157 illustrates a PAP device having a generally square outer casing 5129 having curved surfaces and rounded edges. FIG. 158 illustrates a PAP device having a generally tapered outer casing such that a first end is wider than the opposite second end, the second end including the connection to the air delivery tubing. Such a tapered outer casing may assist in inserting the PAP device within a cover.

7.14 Air Delivery Tubing Length and Diameter

Figure 50:
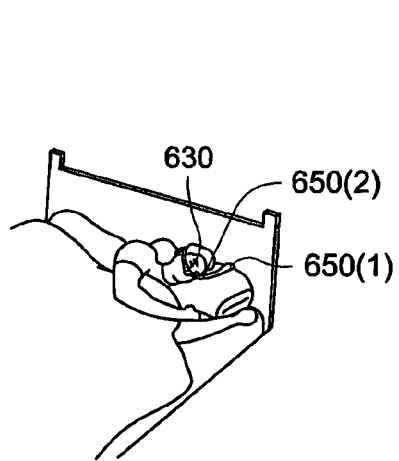
FIGS. 50, 51, 52, and 53 are various perspective views of a PAP system in use according to an example of the present technology.
Figure 51:
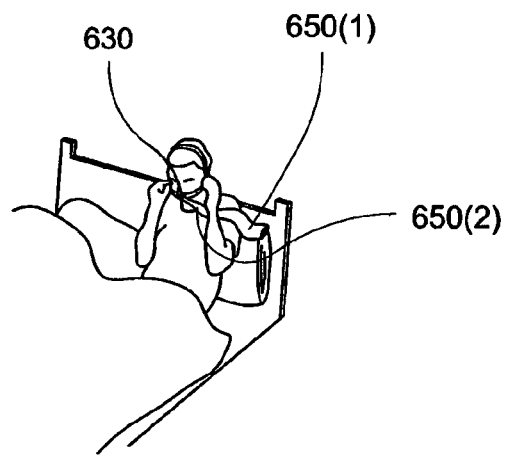
Figure 52:
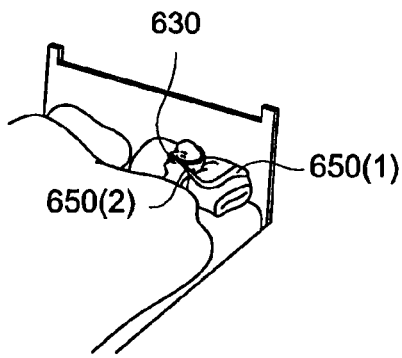
Figure 53:
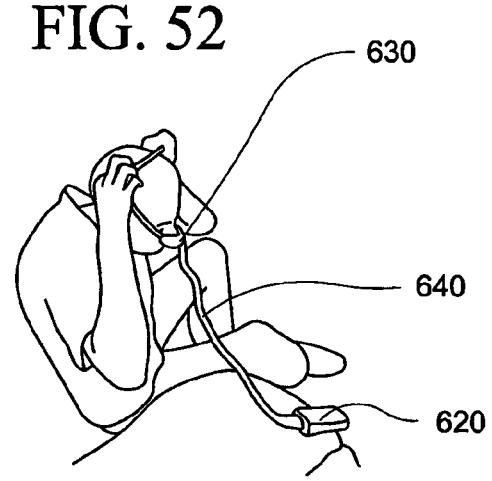

In an example, as shown in FIGS. 50-53, the air delivery tubing 640 that interconnects the patient interface 630 and the PAP device including blower 620 (PAP device and tubing enclosed by cover portions 650(1), 650(2) in FIGS. 50-52) includes a length of about 30-80 cm, e.g., 70 cm. In an example, a length of 70 cm may be preferred as it allows free movement while sitting bedside and lying down in any position. Lengths longer than 70 cm may create more opportunities for tangling and may be cumbersome, while lengths shorter than 60 cm may be restrictive while sitting on the bedside putting the PAP system on. Also, lengths shorter than 60 cm may feel tethered when sitting up. Thus, the PAP system is structured to avoid a "ball and chain" effect.

In an example, the air delivery tube may include two portions, each having different diameters. For example, the portion of the tube near the patient's face may have an external diameter of about 12 mm and the portion of the tube away from the patient's face may have an external diameter of about 19 mm or 22 mm, for example.

Figure 164:
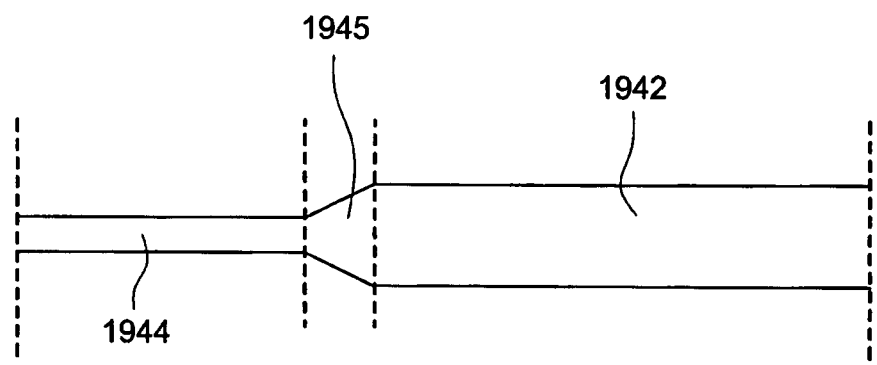
FIG. 164 is a schematic view of air delivery tubing including a tube coupler according to an example of the present technology.
Figure 165:
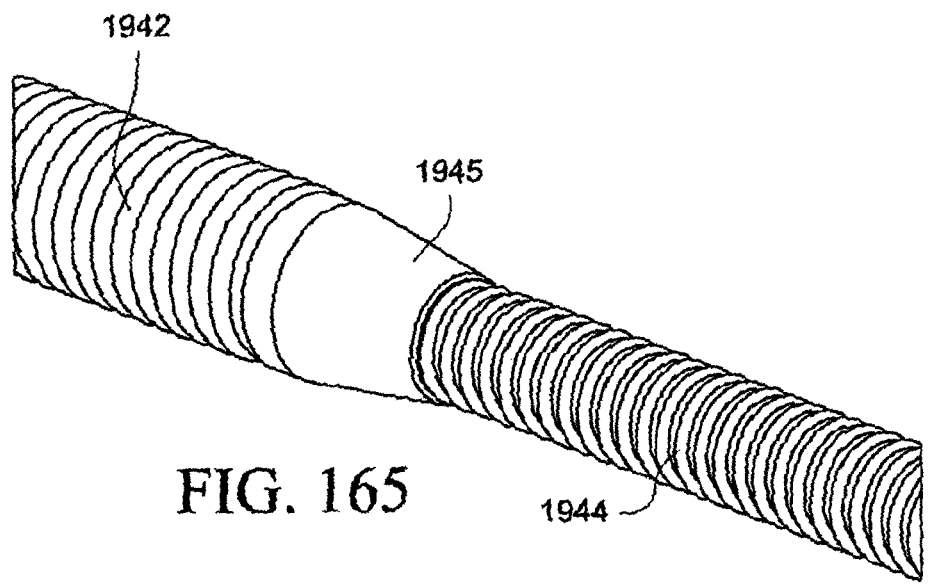
FIG. 165 is a perspective view of air delivery tubing including a tube coupler according to an example of the present technology.
Figure 166:
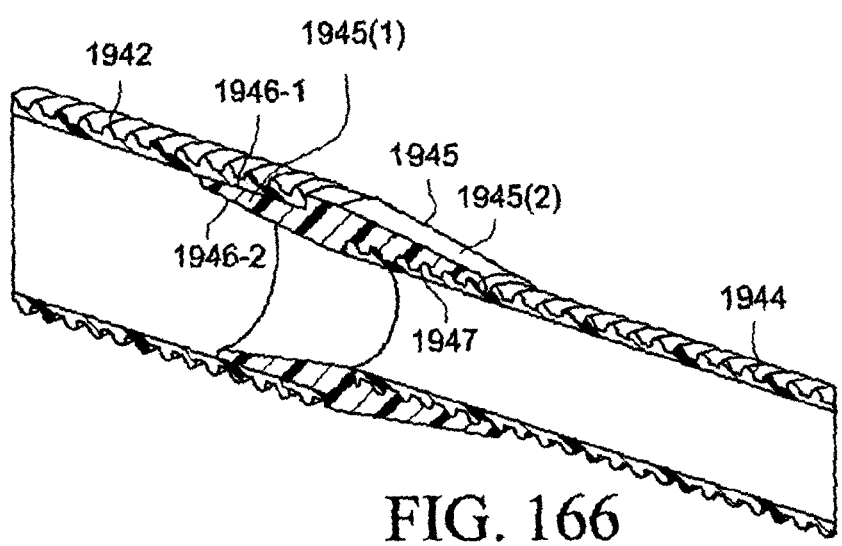
FIG. 166 is a cross-sectional view of the air delivery tubing of FIG. 165.
Figure 167:
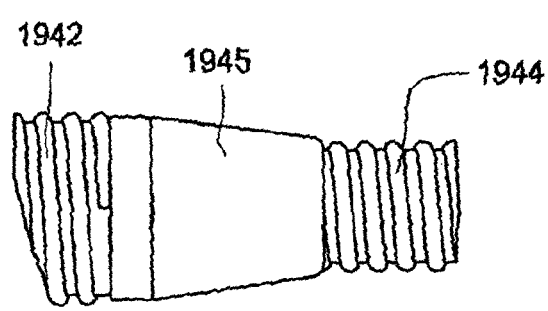
FIG. 167 is a side view of the air delivery tubing of FIG. 165.
Figure 168:
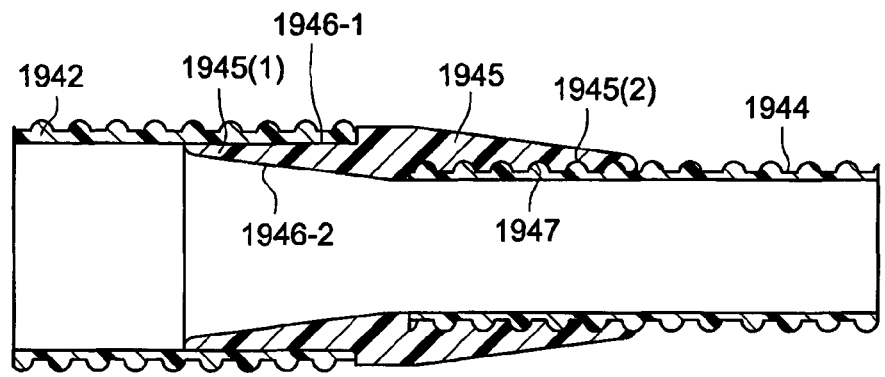
FIG. 168 is a cross-sectional view of the air delivery tubing of FIG. 167.
Figure 169:
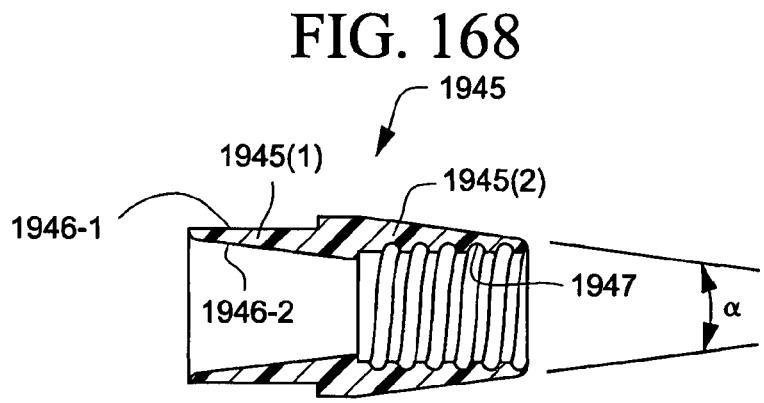
FIG. 169 is a cross-sectional view of a tube coupler according to an example of the present technology.
Figure 170:
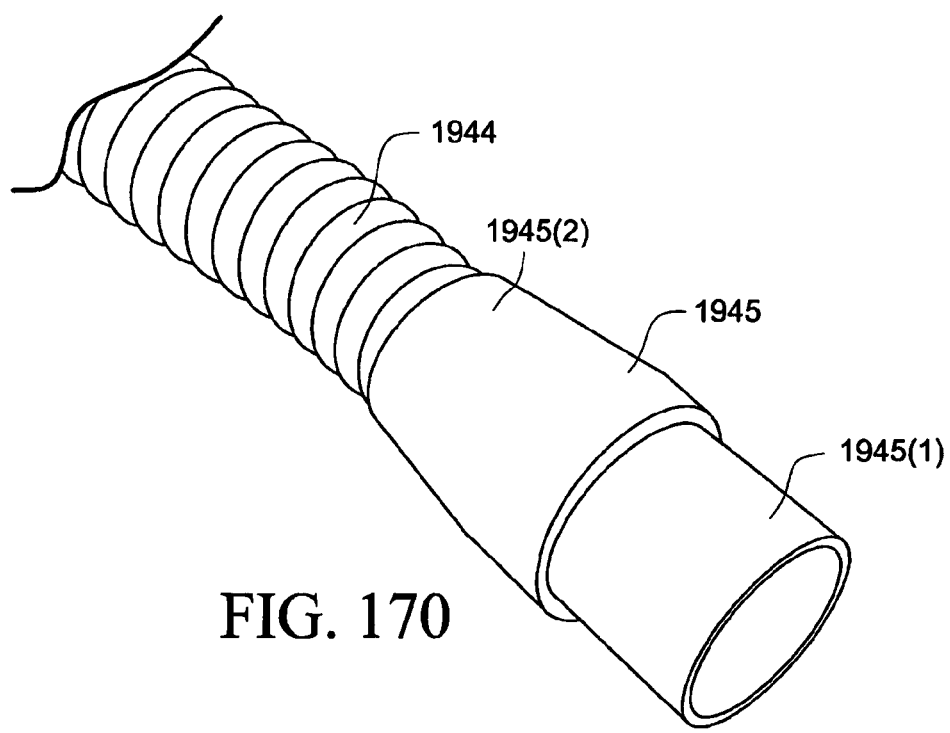
FIG. 170 is a perspective view of air delivery tubing including a tube coupler according to an example of the present technology.
Figure 171:
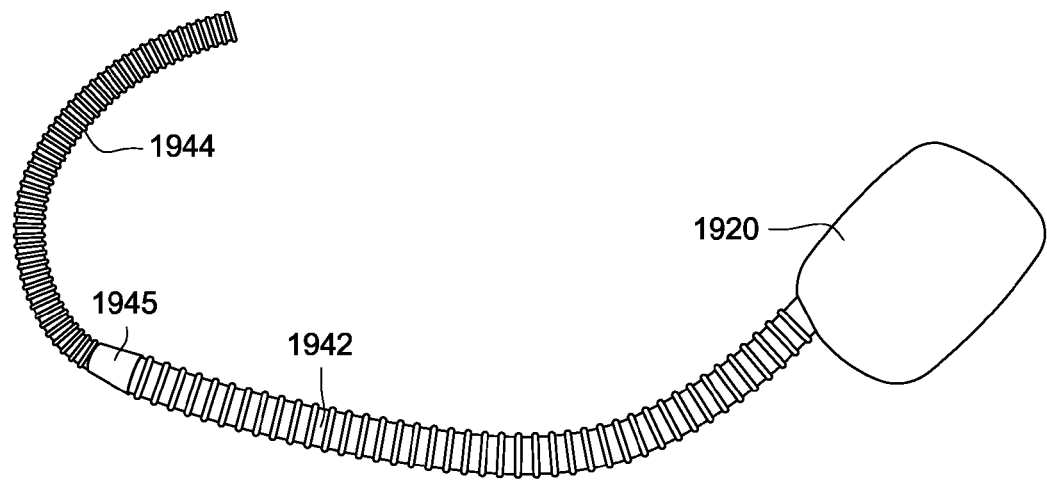
FIG. 171 is a perspective view of a PAP device and air delivery tubing including a tube coupler according to an example of the present technology.

As schematically shown in FIG. 164, a tube coupler 1945 may be provided between the two tube portions to transition the larger diameter tube portion 1942 (e.g., 19 mm tube) to the smaller diameter tube portion 1944 (e.g., 12 mm tube). For example, as shown in FIGS. 165-170, the tube coupler 1945 includes an end portion 1945(1) adapted to engage the larger diameter tube portion 1942 and an end portion 1945(2) adapted to engage the smaller diameter tube portion 1944. As illustrated, the end portion 1945(1) includes a smooth exterior surface 1946-1 adapted to engage the smooth interior surface of the larger diameter tube portion 1942 and a smooth, tapered interior surface 1946-2 adapted to transition airflow from the larger diameter tube portion 1942 to the smaller diameter tube portion 1944. The end portion 1945(2) includes a grooved, interior surface 1947 adapted to engage the ribbed, exterior surface of the smaller diameter tube portion 1944. In an example, as shown in FIG. 169, the transition angle $\alpha$ may be about 10-30°, e.g., 15°. FIG. 171 shows the tube coupler 1945 and tube portions 1942, 1944 with the larger diameter tube portion 1942 attached to a PAP device 1920.

In an alternative example, the air delivery tube may be in the form of a one piece structure which tapers along its length or includes an integral tapered section, i.e., single tube without a separate tube coupler to transition tubing.

7.15 Nasal Interface and Pivot Point

The wrap-type PAP system (e.g., see FIGS. 13-18) may include a wrap-type patient interface (e.g., nasal interface or nozzle/nasal prong arrangement), which exposes the patient's mouth and may work well for back, side, and stomach sleepers. Also, the wrap-type PAP system avoids a blower on the patient's forehead. The wrap-type PAP system provides an unobtrusive arrangement, e.g., humanizing arrangement like a scarf.

Figure 54:
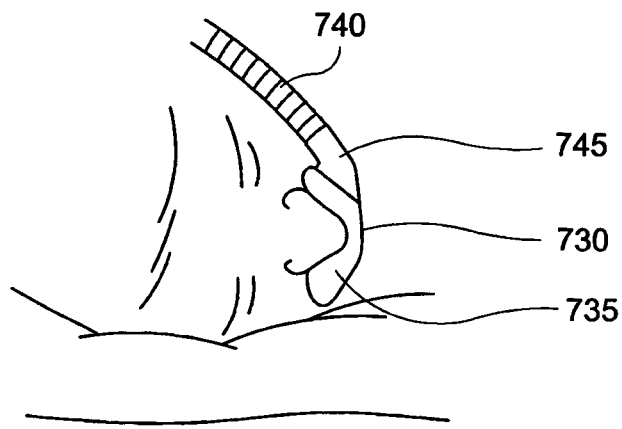
FIGS. 54, 55, and 56 are perspective views of a patient interface with an angled elbow joint according to an example of the present technology.
Figure 55:
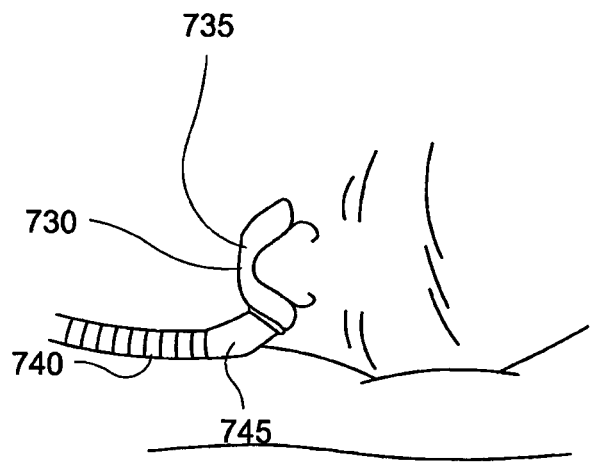
Figures 56, 57:
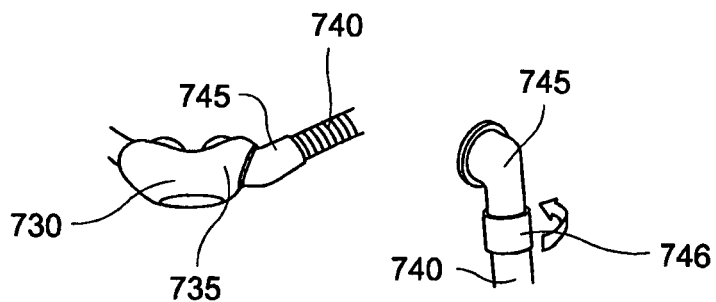
FIG. 57 is a perspective view of an angled elbow joint according to an example of the present technology.
Figures 64, 65:
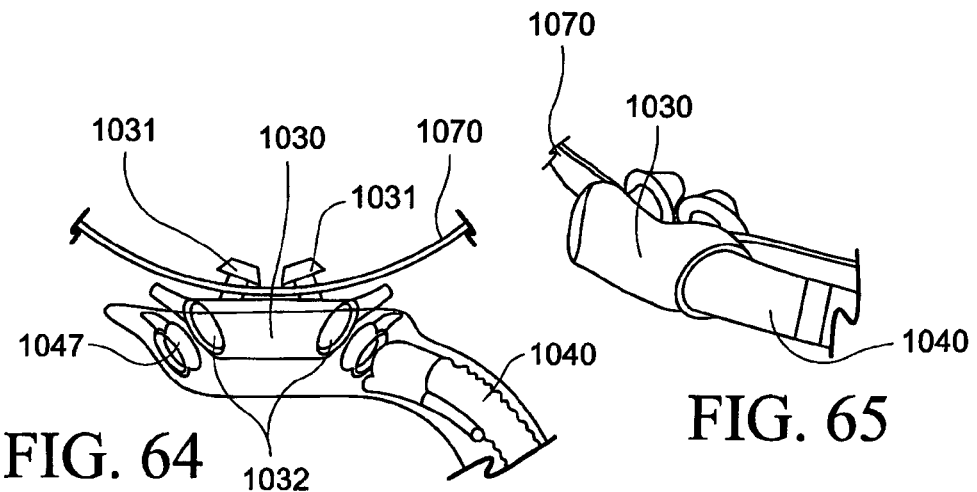
FIG. 64 is a perspective view of a PAP system according to an example of the present technology.
FIG. 65 is a perspective view of the PAP system of FIG. 64.
Figures 66, 67:
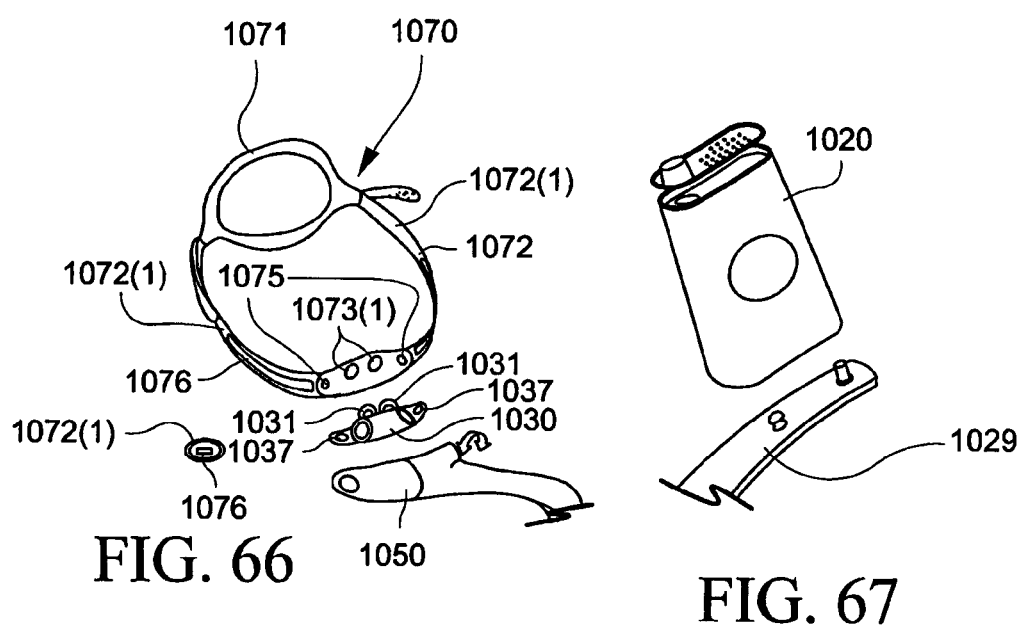
FIG. 66 is an exploded view of the PAP system of FIG. 64.
FIG. 67 is a perspective view of a PAP device of the PAP system of FIG. 64.
Figure 68:
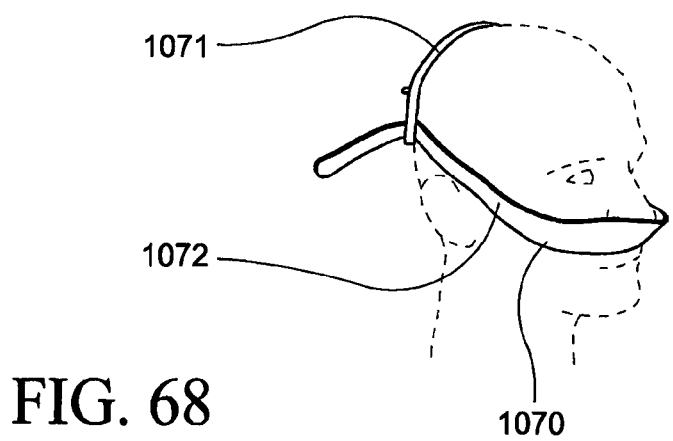
FIG. 68 is a perspective view of the PAP system of FIG. 64 in use.
Figure 69:
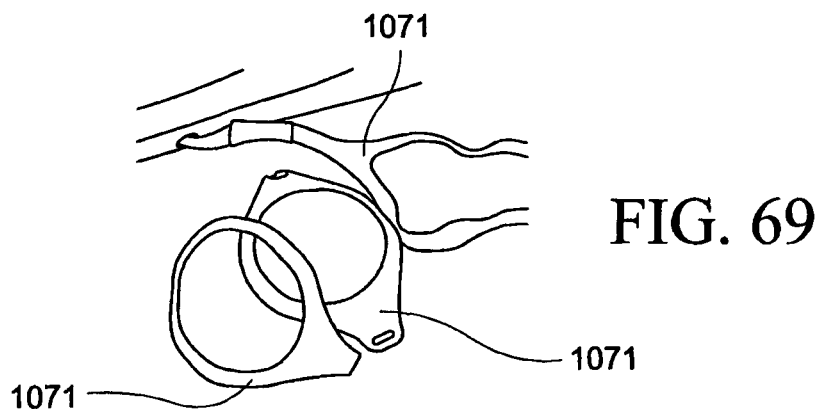
FIG. 69 is a perspective view of headgear of the PAP system of FIG. 64.
Figures 70, 71:
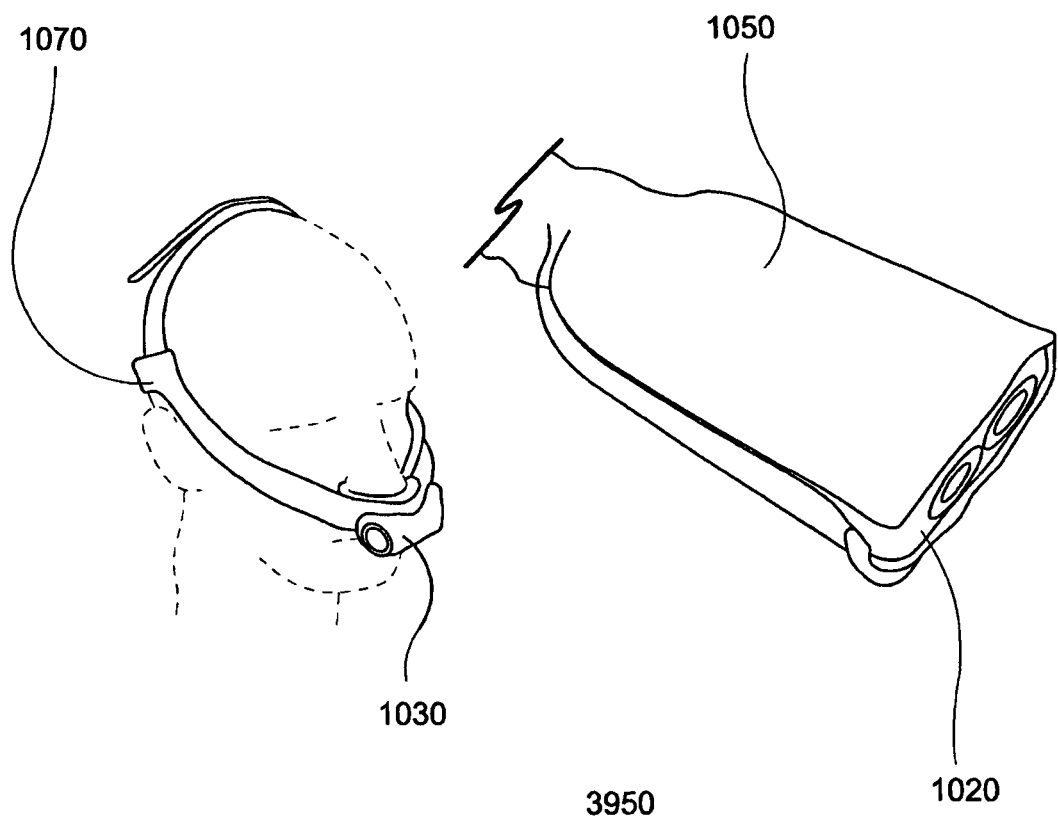
FIG. 70 is a perspective view of the PAP system of FIG. 64 in use.
FIG. 71 is a perspective view of the enclosed PAP device of the PAP system of FIG. 64.

As shown in FIGS. 58 and 59, the nozzle/nasal prong arrangement 730 includes a one-piece structure including a base portion 735 defining a nasal breathing cavity and a pair of nozzles 731 provided to the base portion. Extended connectors 737 (e.g., headgear connectors) are provided to sides of the base portion. A vent 733 is provided in the base portion, preferably to a center of the base portion, i.e., center is preferred as side-venting may be restricted in certain sleeping positions. In an alternative arrangement, the nozzles may be formed separately from the base portion and attached thereto, e.g., FIG. 60 shows exemplary base portion 835 with extended connectors 837, Each lateral side of the base portion includes an inlet or inlet opening 732 structured to communicate with the air delivery tubing 740, e.g., via an angled elbow joint 745 as best shown in FIGS. 54 to 57. As shown in FIGS. 54 and 55, the elbow joint 745 may be coupled to either side of the base portion, which allows selective positioning of the air delivery tubing 740, e.g., depending on sleeping position. The elbow joint 745 may be coupled to the base portion by a swivel ring to permit rotation or swiveling of the elbow joint with respect to the base portion as shown in FIG. 56. Also, a swivel 746 may be provided to the opposite end of the elbow joint 745 and adapted to be connected to the air delivery tubing 740 as shown in FIG. 57.

In an example, structure may be provided to bias the air delivery tubing upward (i.e., toward the top of the pillow) and allow for better tube management in various sleeping positions.

In an example, structure may be provided to allow the angle of presentation of the patient interface to be adjusted, e.g., provide pivot or allow rotation of the patient interface, 7.16 Reversibility As noted above, the PAP system may be reversible, i.e., air delivery tubing may extend from either side of the patient interface. Reversibility addresses the usability case of sitting in bed, before lying down. Same-side orientation keeps the tube in the right position as the patient adjusts for sleep. If the system is not reversible, it may feel more tethered or constrained.

Reversibility also allows the system to be separated from the bed partner. Because the system is a personal device, the air delivery tubing should be positioned on the opposite side of the face from the bed partner.

FIGS. 61, 62, and 63 show an exemplary reversible PAP system. In this example, the PAP system includes a patient interface 930 (e.g., nozzle/nasal prong arrangement) supported within a cover 950(1) including side strap portions 951 to support the system on the patient's head. The patient interface 930 includes a pair of inlet openings 932 that align with respective openings provided in the cover 950(1). An air delivery tube 940 is supported within a cover 950(2) and structured to interconnect the patient interface and the flow generator. The air delivery tube 940 includes an end portion 940(1) adapted to engage one of the inlet openings 932, e.g., flexible connection, snap-in connection via a sleeve provided to the patient interface. A plug or button 947 engages the other of the inlet openings. In addition, the plug or button extends through an opening in the cover 950(2) to secure the end of the cover in position. FIGS. 62 and 63 show a primary position of the air delivery tubing and reversed position of the air delivery tubing.

FIGS. 64 to 71 illustrate a PAP system according to another example of the present technology. In this example, the PAP system includes a PAP device 1020, an air delivery tube 1040, a patient interface 1030 (e.g., nozzle/nasal prong arrangement), and headgear 1070 to support the patient interface in a desired position on the patient's face.

The patient interface includes a pair of inlet openings 1032, one of which engages the air delivery tube 1040 (e.g., via a seal ring between the inlet opening and air delivery tube) and the other of which engages a plug 1047. The headgear 1070 includes a generally circular rear strap 1071 adapted to engage or cup the patient's occiput and a front strap 1072 that extends from the rear strap to support the patient interface. Side strap portions 1072(1) of the front strap may adjustably and releasably engage respective sides of the rear strap 1071, e.g., via a hook and loop fastening arrangement. However, the front strap and rear strap may be integrally formed as a one piece structure.

The front strap 1072 includes openings 1073(1) to receive respective nozzles 1031 of the patient interface 1030 therethrough, and connection tabs 1075 to interlock with respective openings provided to extended connectors 1037 of the patient interface. Each side strap portion 1072(1) may include rigidizer or stiffening element 1076 to add rigidity to the side strap portions for stably supporting the patient interface in position.

A cover 1050 substantially encloses one or more portions of the PAP device 1020 and the air delivery tube 1040. In an example, the power cord 1029 (e.g., see FIG. 67) for the PAP device 1020 may be in the form of a generally flat strap, e.g., versus a typical round cord.

In an example, a humidifier may be incorporated into the system to provide humidification.

In an example, the rigidizer or stiffening element may be structured to provide rigidity in some planes yet allow flexibility or adjustment in other planes. For example, the rigidizer may include a line of weakness, hinge, scoring, and/or joint (e.g., Thermoplastic Elastomer (TPE) joint) to allow flexibility or adjustment.

7.17 Connection and Alignment

In an example, the headgear supporting the patient interface may include connection and alignment tabs to connect and properly align the patient interface.

For example, as shown in FIG. 72, each rigidizer 1076 provided to the side strap portion 1072(1) of the headgear may include a connection tab or element 1075. The connection tab may, be integrally molded into the rigidizer, e.g., formed via heat swage. In use, as shown in FIG. 73, the connection tabs interlock within respective openings 1037 (1) provided to the extended connectors 1037 of the patient interface 1030 (e.g., including nasal cushion or nasal interface). In an example, the patient interface may have common characteristics with the mask described in PCT Application No. PCT/AU2010/000684, filed Jun. 2, 2010, which is incorporated herein by reference in its entirety. Alternatively, as shown in FIG. 73, the tabs 1075 may be in the form of rivets structured to extend through or be riveted to the side strap portions 1072(1). In an example, each tab may be riveted in from one side of the fabric strap portion and the other side of the fabric strap portion may hide the rivet.

In an example, the straps of the headgear include a foam/fabric laminate with possible thermoplastic polyurethane (TPU) bonding. Edges of the straps may be sonobonded for cleanliness. Sewing may be used, e.g., where material creates a complex connection.

In another example, as shown in FIGS. 74 and 75, a snap-on post 1175 may be provided to the rigidizer 1076 of the side strap portion 1072(1), and a ring 1137(1) may be provided to respective extended connectors 1037 of the patient interface to engage the post. The patient interface may be formed via two-part mold with the ring being a different durometer of silicone than the remainder of the patient interface.

Figure 76:
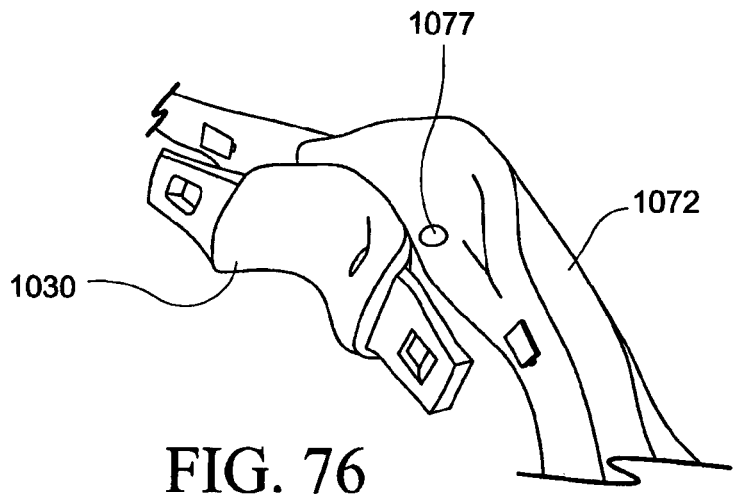
FIG. 76 is a perspective view of a PAP system including an alignment nub according to an example of the present technology.
Figures 77, 78:
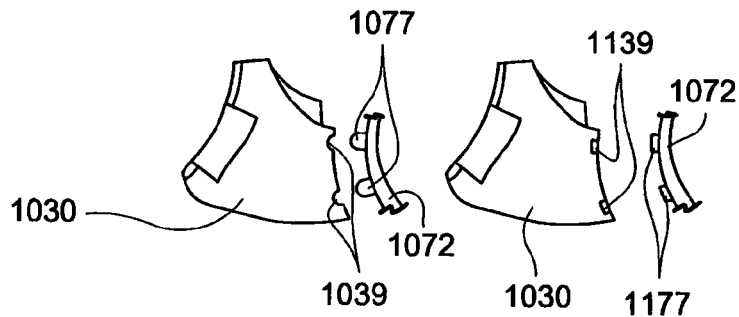
FIG. 77 is a schematic view of a PAP system including alignment nubs according to an example of the present technology.
FIG. 78 is a schematic view of a PAP system including magnetic alignment nubs according to an example of the present technology.

The front strap may also include one or more alignment nubs or protrusions to align the patient interface and maintain its position. For example, FIG. 76 shows a single central alignment nub 1077 provided to the front strap 1072 and adapted to align the patient interface 1030 (e.g., including nasal cushion or nasal interface). In FIG. 77, the front strap includes a pair of alignment nubs 1077 adapted to engage respective recesses 1039 provided to the patient interface 1030. In FIG. 78, the alignment nubs may be in the form of magnets 1177 (e.g., neodymium magnets adhered to fabric strap) structured to magnetically interface with metal inserts 1139 provided (e.g., co-molded) to the patient interface.

Figure 79:
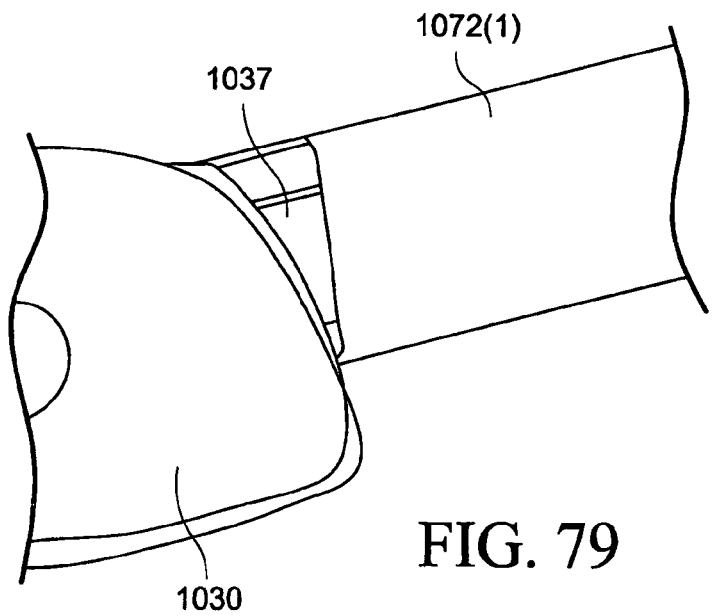
FIGS. 79, 80, and 81 show various views of a patient interface including extended connectors tucked into headgear straps according to an example of the present technology.
Figure 80:
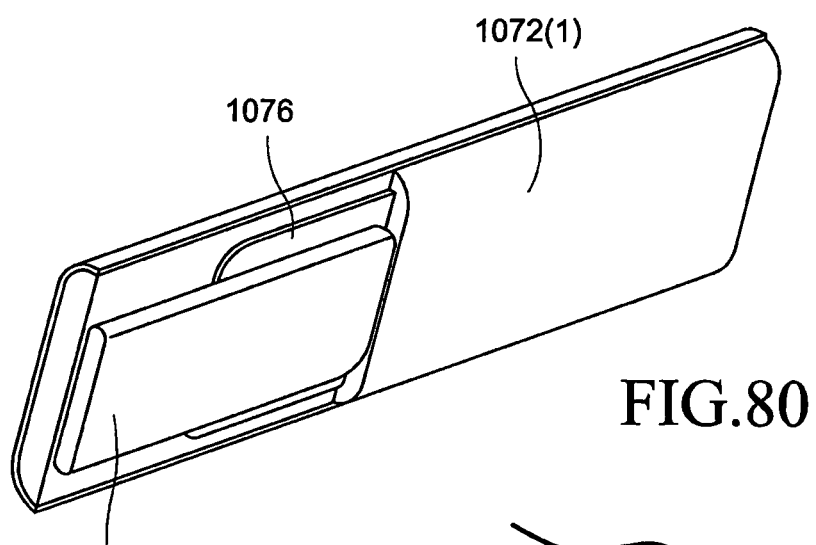
Figure 81:
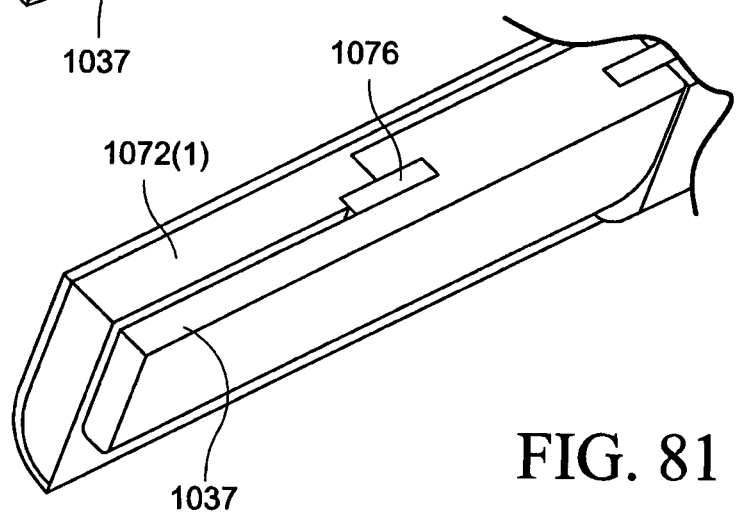

In another example, as shown in FIGS. 79, 80, and 81, the extended connectors or wings 1037 of the patient interface 1030 may be tucked into the side strap portions 1072(1) of the headgear. As illustrated, the extended connectors 1037 are tucked under the fabric and at least a portion of the connector 1037 extends alongside the rigidizer 1076 provided within the side strap portion. This arrangement minimizes the overall impact and appearance of the connection between the patient interface and headgear.

Figure 172:
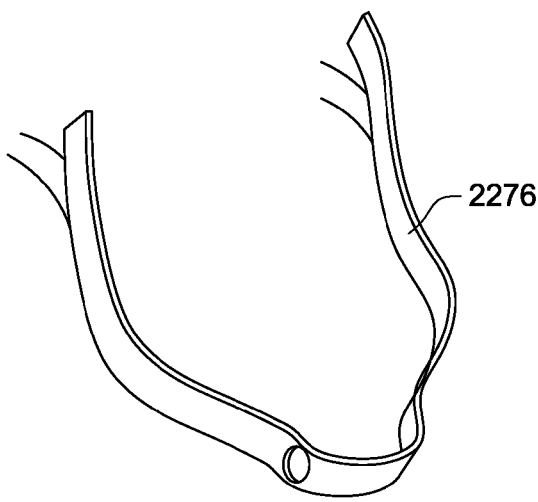
FIG. 172 shows a rigidizer for a patient interface according to an example of the present technology.

FIG. 172 shows another example of a rigidizer 2276 structured to extend from ear to ear across the front of the patient interface to provide sufficient sealing force for the cushion or nozzle arrangement. In an example, the rigidizer may be structured such that it is laterally flexible but vertically stiff in use.

Figure 173:
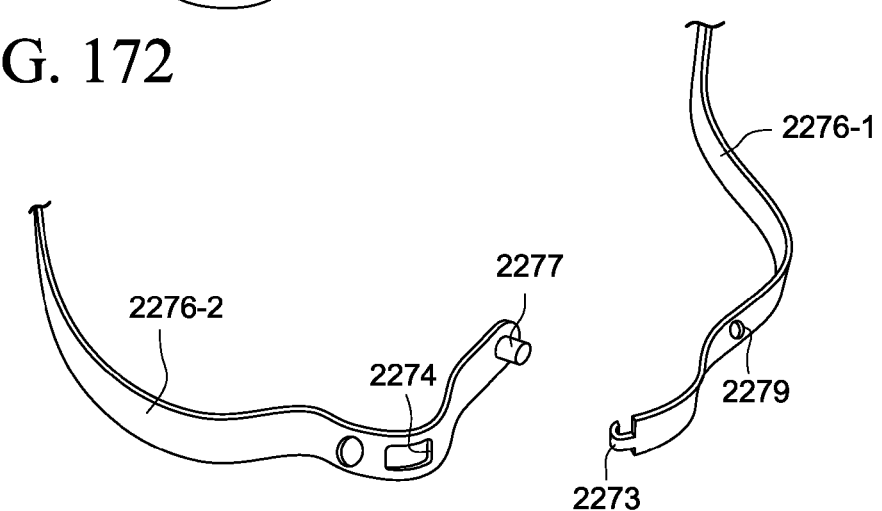
FIGS. 173 and 174 show a rigidizer for a patient interface according to another example of the present technology.
Figure 174:
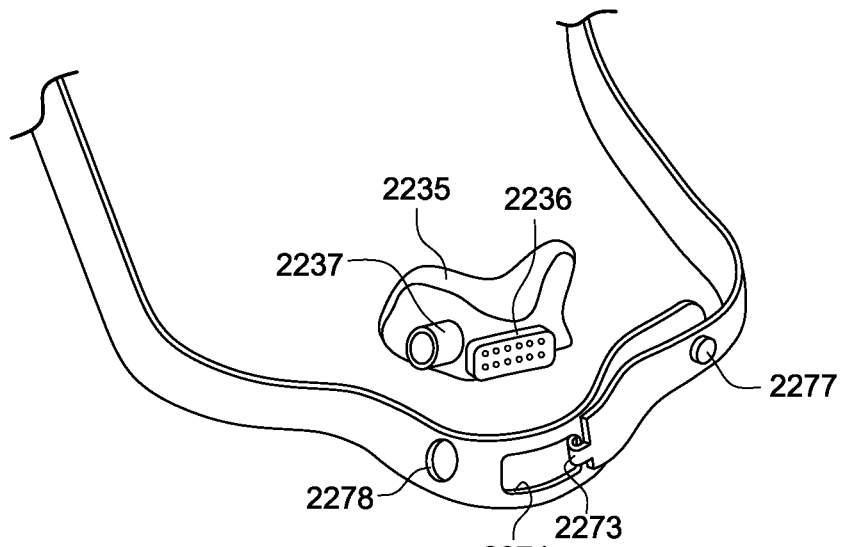

In an alternative example, as shown in FIGS. 173 and 174, the rigidizer may be provided in two parts structured to interlock with one another, i.e., first rigidizer portion 2276-1 attachable to second rigidizer portion 2276-2. In the illustrated example, the first and second rigidizer portions 2276-1, 2276-2 are attached by a hook and snap arrangement, e.g., first rigidizer portion 2276-1 includes hook 2273 adapted to engage within opening 2274 provided to second rigidizer portion 2276-2 and second rigidizer portion 2276-2 includes a protrusion 2277 adapted to engage within opening 2279 provided to first rigidizer portion 2276-1, e.g., with a snap-fit. However, it should be appreciated that the first and second rigidizer portions 2276-1, 2276-2 may be attached to one another in other suitable manners.

The cushion 2235 includes a protrusion 2236 (e.g., including one or vents) adapted to engage within the opening 2274 and an inlet tube 2237 adapted to extend through opening 2278 in the second rigidizer portion 2276-2. Such arrangement locates and retains the cushion to the rigidizer.

Figure 175:
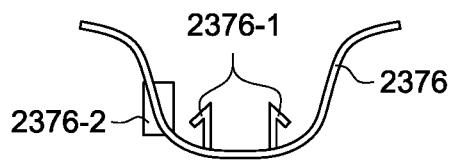
FIG. 175 shows a rigidizer for a patient interface according to another example of the present technology.
Figure 176:
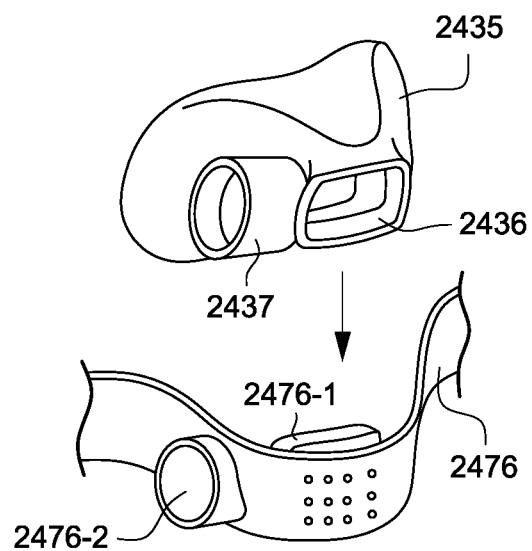
FIG. 176 shows a rigidizer and cushion for a patient interface according to another example of the present technology.
Figure 177:
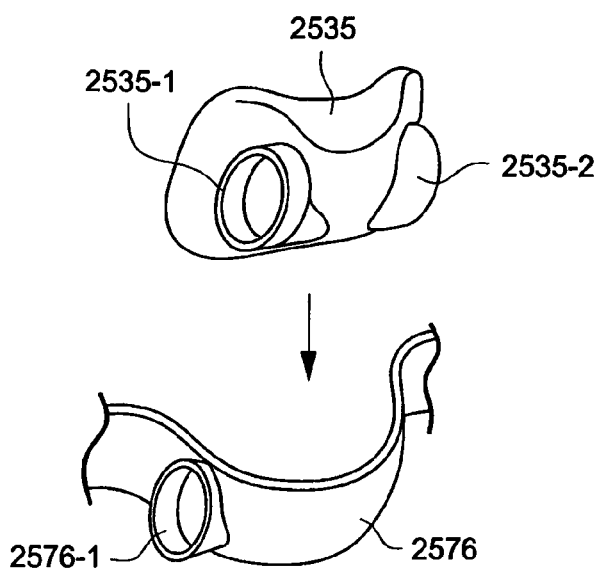
FIGS. 177 and 178 show a rigidizer and cushion for a patient interface according to another example of the present technology.
Figure 178:
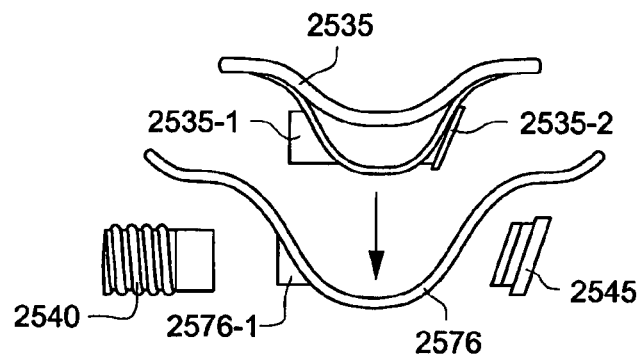
Figure 179:
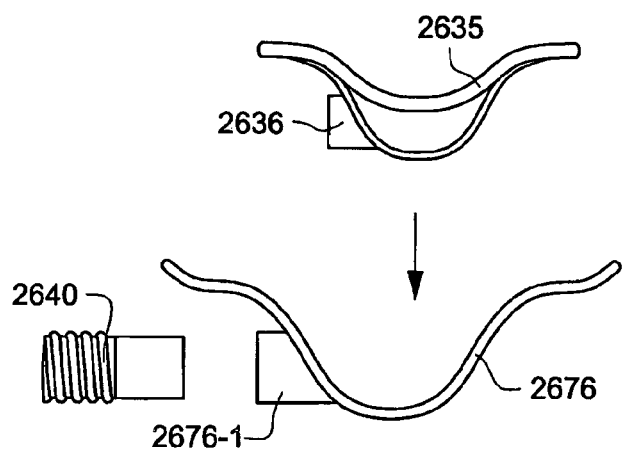
FIG. 179 shows a rigidizer and cushion for a patient interface according to another example of the present technology.

FIGS. 175 to 179 show alternative examples for attaching the cushion to the frame or rigidizer of the patient interface. For example, FIG. 175 shows a rigidizer 2376 including barbed or hook-like retaining members 2376-1 adapted to locate and retain the cushion. Also, the rigidizer 2376 includes a tube portion 2376-2 adapted to locate and engage the inlet of the cushion. In FIG. 176, the rigidizer 2476 includes a protrusion 2476-1 adapted to engage within the opening 2436 provided to the cushion 2435 and a tube portion 2476-2 adapted to engage inlet 2437 of the cushion. In this example, the rigidizer provides vents and is configured and arranged to allow the cushion to seal on the rigidizer. In FIGS. 177 and 178, the rigidizer 2576 provides a tube portion 2576-1 and an opposed opening (not visible) adapted to locate and align with a tube 2535-1 and opposed opening 2535-2 provided to the cushion 2535. In this example, an inlet tube 2540 is provided to the tube portion 2576-1 and a plug-type vent 2545 is provided to the opposed opening, which help to locate and retain the cushion to the rigidizer. In FIG. 179, the rigidizer 2676 provides a tube portion 2676-1 adapted to locate and retain a tube portion 2636 provided to the cushion 2635. In this example, a vent may be integrated with the tube 2640 and/or tube portion 2676-1.

In another example, the cushion may be supported by a cradle which can be rotated relative to rigidizers provided to the side strap portions of the headgear. This arrangement allows the cradle and hence the cushion to be rotated to allow adjustment to suit the naso-labial angle for a large range of patients. An indexing and/or friction joint may be provided between the cradle and the rigidizers to provide sufficient rotation torque, e.g., to provide tactile/audible feedback, to reduce tube drag.

In another example, the cradle supporting the cushion may be fixed with respect to the rigidizers, and the cushion may be rotatable relative to the cradle to allow adjustment.

7.18 Rotating Rigid Elbow

Figure 82:
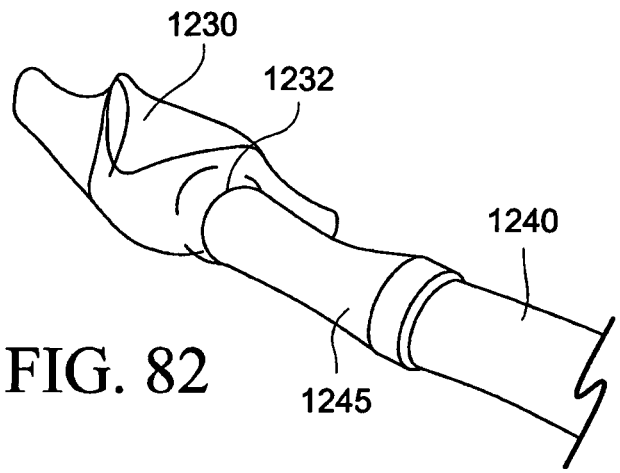
FIGS. 82 and 83 are various views of a patient interface with a rotating rigid elbow according to an example of the present technology.
Figure 83:
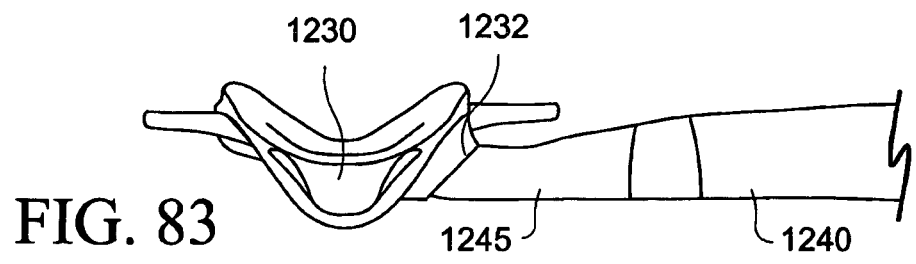
Figure 85:
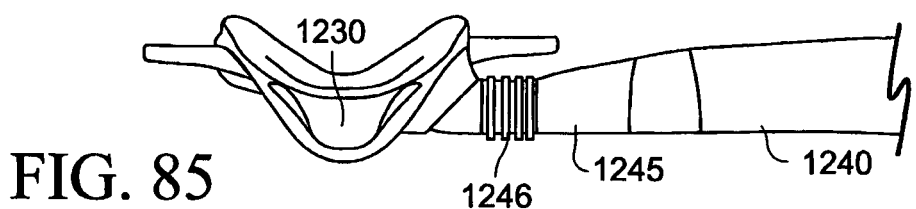
FIG. 85 is a front view of a patient interface with a rotating rigid elbow according to an example of the present technology.
Figure 84:
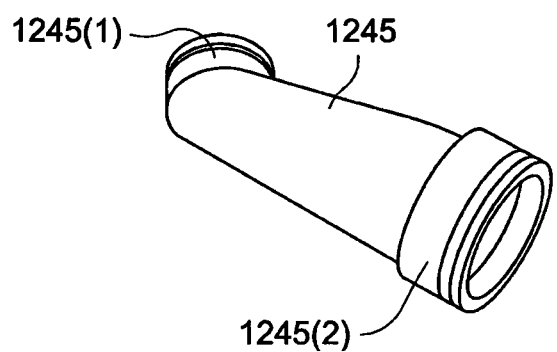
FIG. 84 is a perspective view of the elbow of FIGS. 82 and 83.

In an example, as shown in FIGS. 82 to 84, a rotating rigid elbow 1245 may be provided between the patient interface 1230 (e.g., including nasal cushion or nasal interface) and the air delivery tube 1240. As illustrated, each inlet opening 1232 of the patient interface includes a circular cut, e.g., at 45°, to create an ellipse. In an example, the elbow may be made from an elastomeric or flexible component to allow the air delivery tube to rotate even though connected to patient interface. Such arrangement may facilitate connection, allow flexibility to movement, and/or provide improved sealing between the elbow and the air delivery tube. Also, such arrangement will prevent some tube drag from disengaging the patient interface from the patient's face. The elbow 1245 includes a first end with an angled connector 1245(1) adapted to engage the inlet opening and a second end 1245(2) adapted to engage the air delivery tube. The elbow connects and rotates at an angle with respect to the patient interface. In an example, as shown in FIG. 85, a gusset, bellows or flexible portion 1246 may be provided to the elbow, e.g., for strain relief.

Advantages of such arrangement include: minimized bend radius; flexible orientation while sleeping, can move the air delivery tube out of the way; allow for complex shapes and transitions; optimizes aesthetic at nose area; and/or non-collapsible.

7.19 All-in-One Patient Interface and Air Delivery Tube

In an example, as shown in FIGS. 86 and 87, the air delivery tube 1340 may be integrally molded in one piece (e.g., molded of silicone) with the patient interface 1330 (e.g., including nasal cushion or nasal interface) to provided a one-piece structure.

Advantages of such arrangement include: single part; complex geometries possible; can use multiple durometers for different densities; can include gusseting/strain relief; and/or can vary cross-section of air delivery tube.

As illustrated, the patient interface may include a nasal cradle arrangement as described in U.S. patent application Ser. No. 13/321,981, filed Nov. 22, 2011, which is incorporated herein by reference in its entirety.

7.20 Direct Connection with Flexible Tube

In an example, as shown in FIGS. 88 and 89, the patient interface 1430 (e.g., including nasal cushion or nasal interface) may have a direct connection with the flexible air delivery tube 1440. The radius of the inlet opening 1432 in the patient interface may be determined by the size of the tube and/or the size of ribbing provided to the tube.

Advantages of such arrangement include: can use complex composite tubing; can achieve very flexible tubes; minimizes cost on the tubing; and/or can achieve tight bend radii with right construction and radius of tube.

In an alternative example, the patient interface may have a ball and socket type connection with the air delivery tube, e.g., the end of the air delivery tube includes a ball adapted to snap-fit into a socket provided to the inlet opening of the patient interface so as to retain the tube to the patient interface. Such ball and socket type connection may function as an exclusive connection so the interface may not be used with components from a conventional CPAP device as described below.

7.21 Exclusive Connection

In an example, the PAP system may be structured such that it won't allow the use of other masks, blowers, and/or tubing, e.g., CPAP masks, CPAP blower, CPAP tubing. Thus, the patient cannot replace the patient interface with a CPAP mask and/or replace the blower with a CPAP blower, for example. Conversely, the subject PAP system may be structured such that its components, e.g., patient interface, cannot be used in a conventional CPAP device. For example, the subject patient interface may include structure to prevent connection to a conventional CPAP air delivery tube.

The subject PAP system is structured for different applications (e.g., snore detection, diagnostics), different pressures (e.g., 0-8 cmH$_2$O, e.g., 2-6 cmH$_2$O), and/or different sealing requirements than a conventional CPAP device (e.g., pressure in the range of 4-30 cmH$_2$O, e.g., 10-12 cmH$_2$O), and therefore it may not be desired to allow use of such system with any components from a conventional CPAP device.

7.22 Induction Power Example

Figure 90:
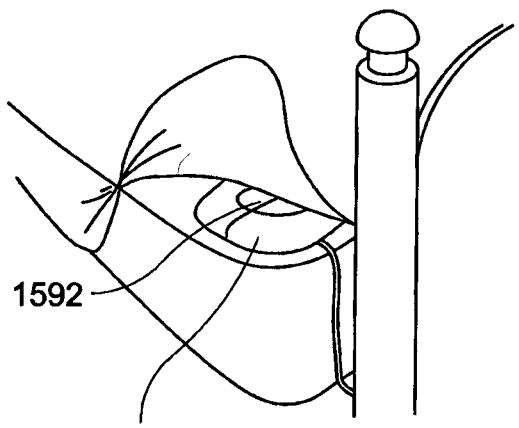
FIGS. 90, 91, and 92 are various views of a PAP system powered by induction according to an example of the present technology.
Figure 91:
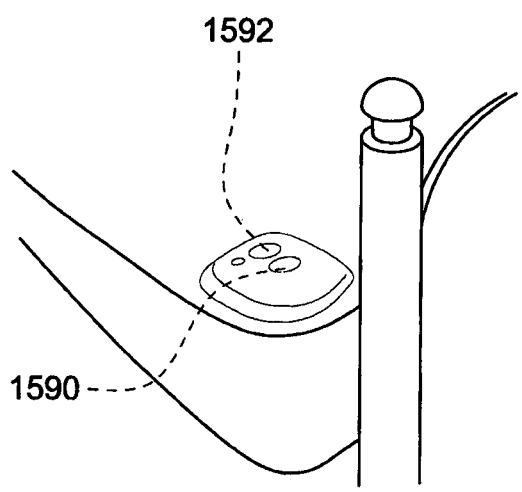
Figure 92:
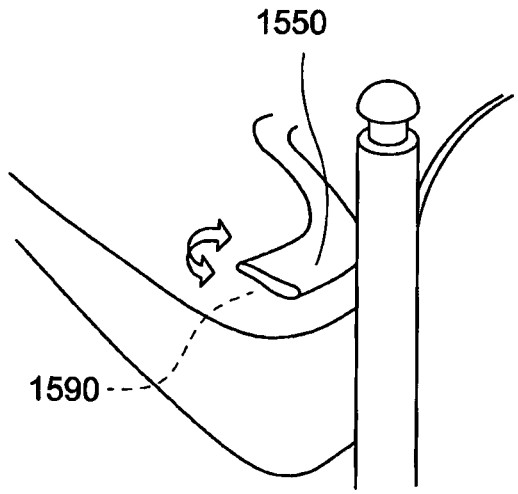

In an example, the blower of the PAP system may be powered by induction. For example, as shown in FIGS. 90 to 92, a charging mat 1590 may be placed under the bed sheet (e.g., fitted sheet to secure it in position) adjacent the top end of the bed. The charging mat 1590 may be plugged into an outlet. As shown in FIG. 91, the charging mat 1590 includes a user interface 1592 (e.g., having glowing lights or an illuminated display) that shows user inputs and feedback though the bed sheet. The blower (e.g., enclosed within a cover 1550) may be attached or otherwise coupled to the charging mat 1590, e.g., magnetically attached. Power to operate the blower may then be delivered by the charging mat through the sheets/cover to the blower.

8. Examples of PAP Device and Cover

Figure 93:
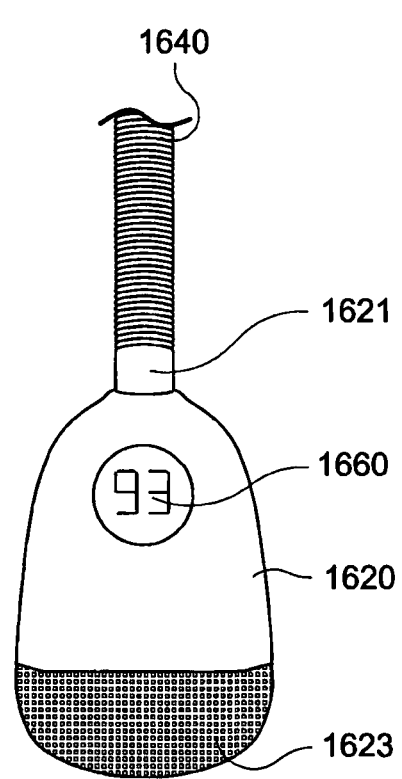
FIGS. 93 and 94 show a PAP device according to an example of the present technology.
Figure 95:
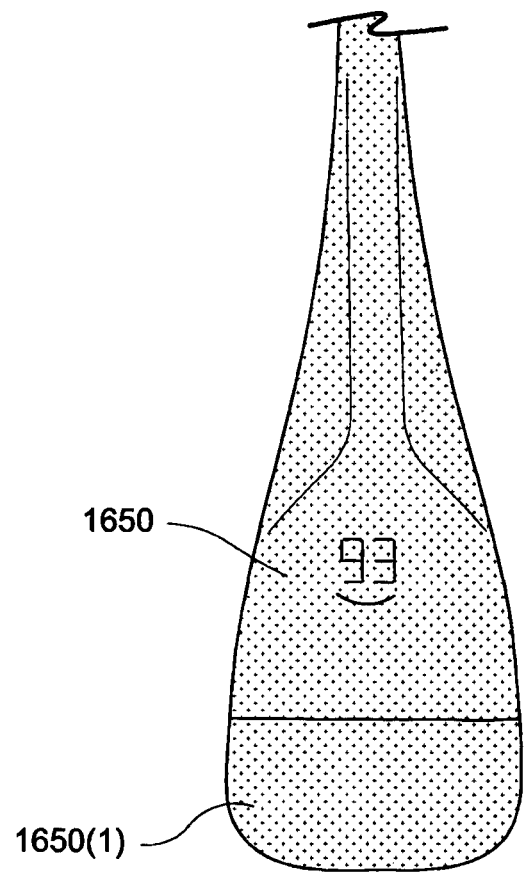
FIG. 95 shows the PAP device of FIGS. 93 and 94 enclosed by a cover according to an example of the present technology.
Figure 94:
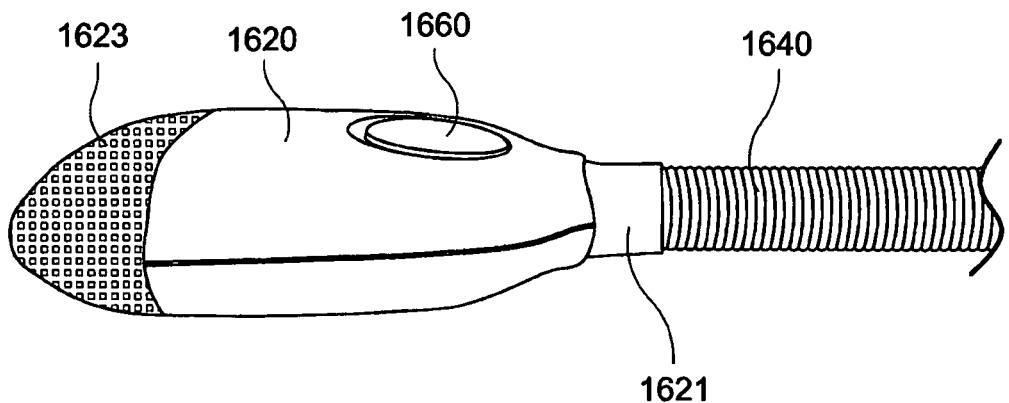

FIGS. 93 and 94 show a PAP device 1620 and FIG. 95 shows such PAP device enclosed by a cover 1650 according to an example of the present technology. As illustrated, the PAP device 1620 includes a central or symmetrical outlet 1621 structured to communicate with the air delivery tube 1640. The air intake 1623 includes a continuous pattern, and may include a removable filter. A large push button 1660 is provided to the top of the PAP device and reveals a numeric or digital display below. The digital display provides clear and understandable feedback to enhance compliance. As best shown in FIG. 94, the housing (e.g., constructed of plastic) of the PAP device provides an exterior surface with a smooth, continuous taper.

The cover 1650 (e.g., constructed of a fabric material or textile materials) allows the numeric display from the button 1660 to glow therethrough, e.g., see FIG. 95. A filter-type fabric portion 1650(1) of the cover 1650 covers the air intake, e.g., enhancing the feeling of clean air. A fitted fabric may be bonded on both sides of the air delivery tube. In an example, the fabric cover may be structured to muffle or suppress noise. Also, the cover may be seamless, e.g., to avoid sharp or rough edges.

Figure 96:
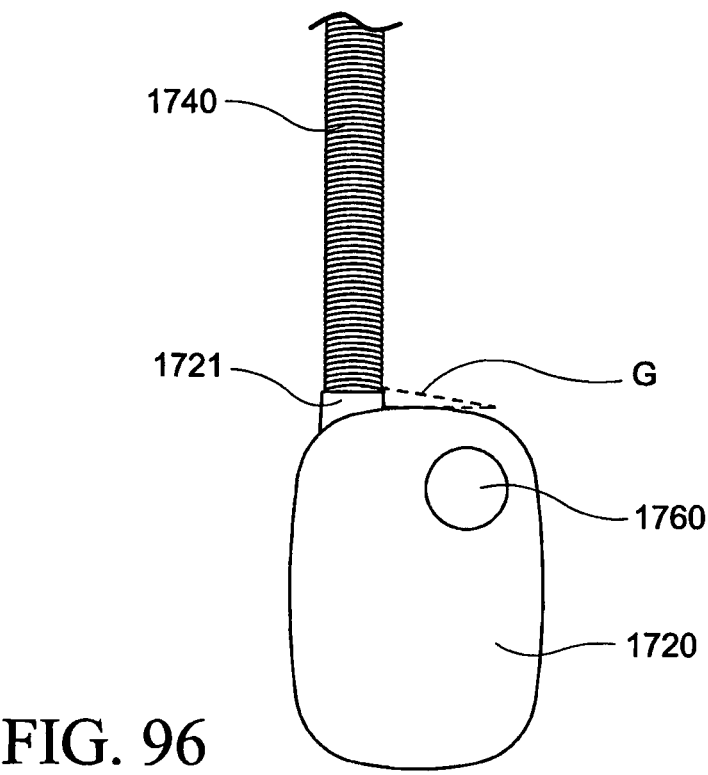
FIGS. 96, 97, and 98 show a PAP device according to an example of the present technology.
Figure 97:
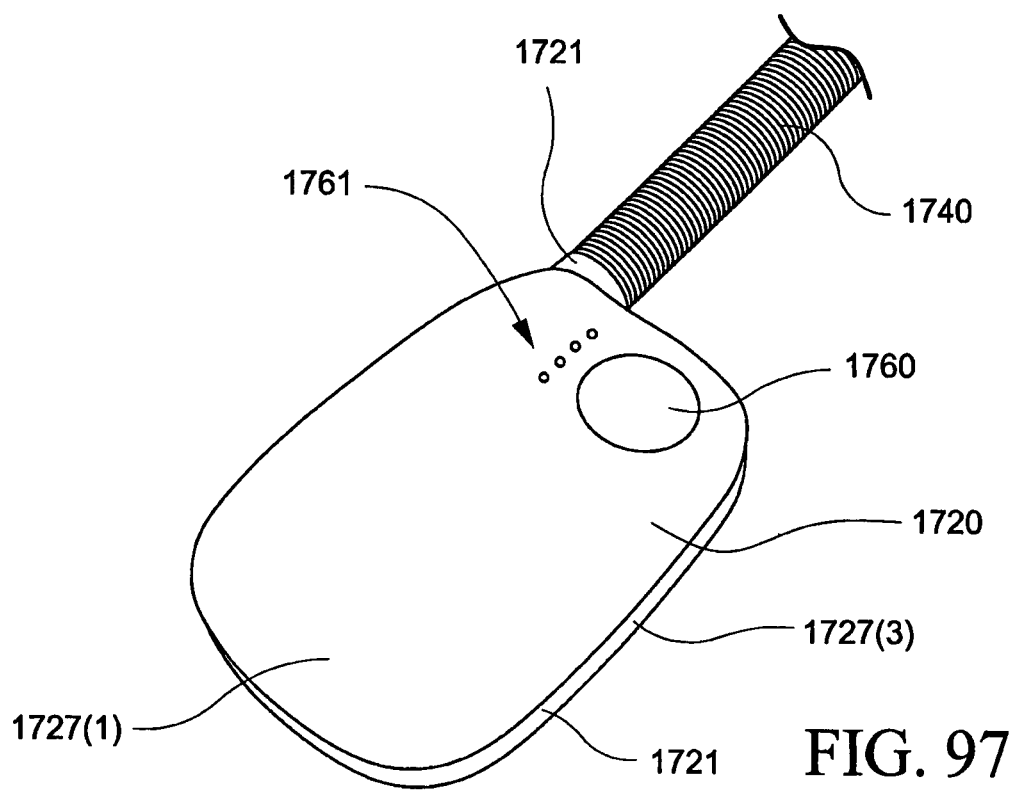
Figure 98:
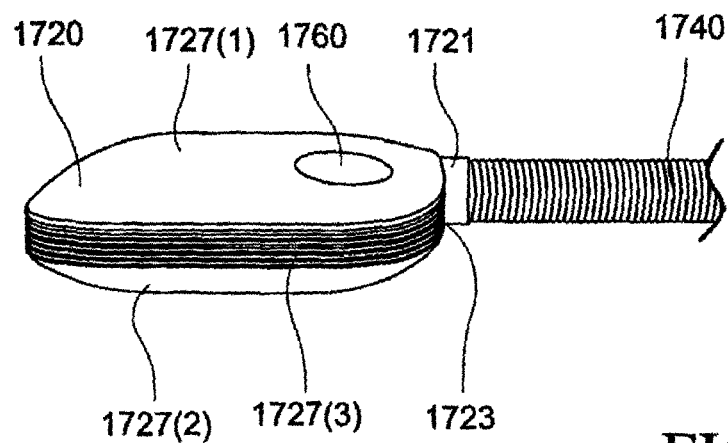
Figure 99:
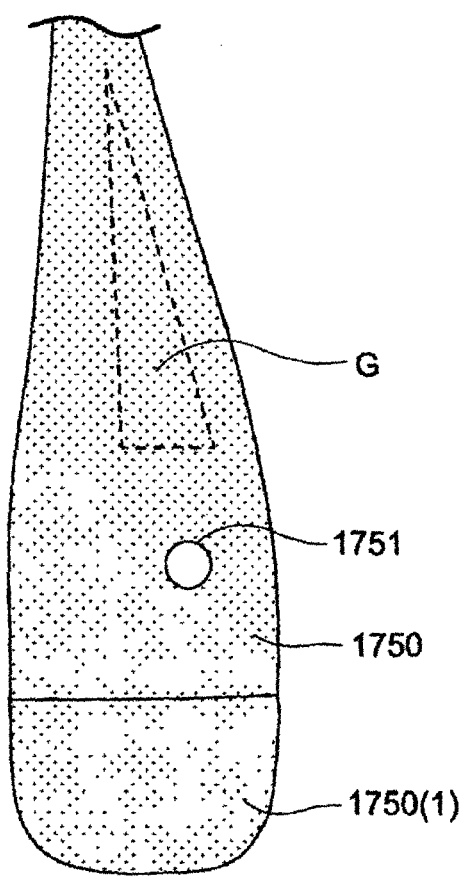
FIG. 99 shows the PAP device of FIGS. 96 to 98 enclosed by a cover according to an example of the present technology.
Figure 126:
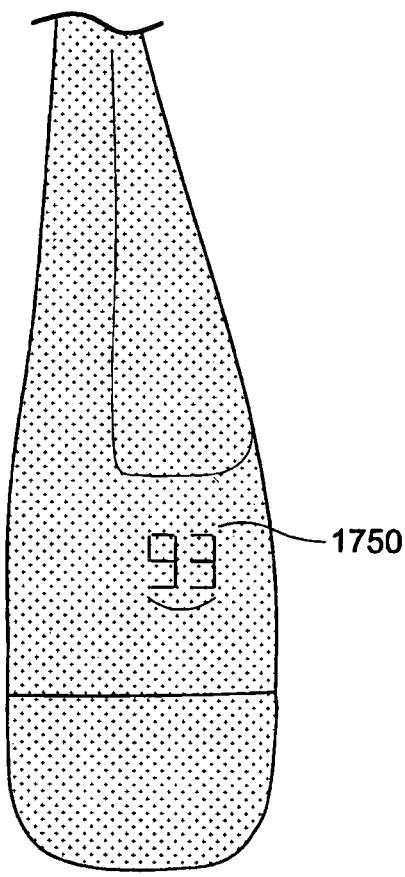
FIG. 126 shows a PAP device enclosed by a cover according to an example of the present technology.
Figure 127:
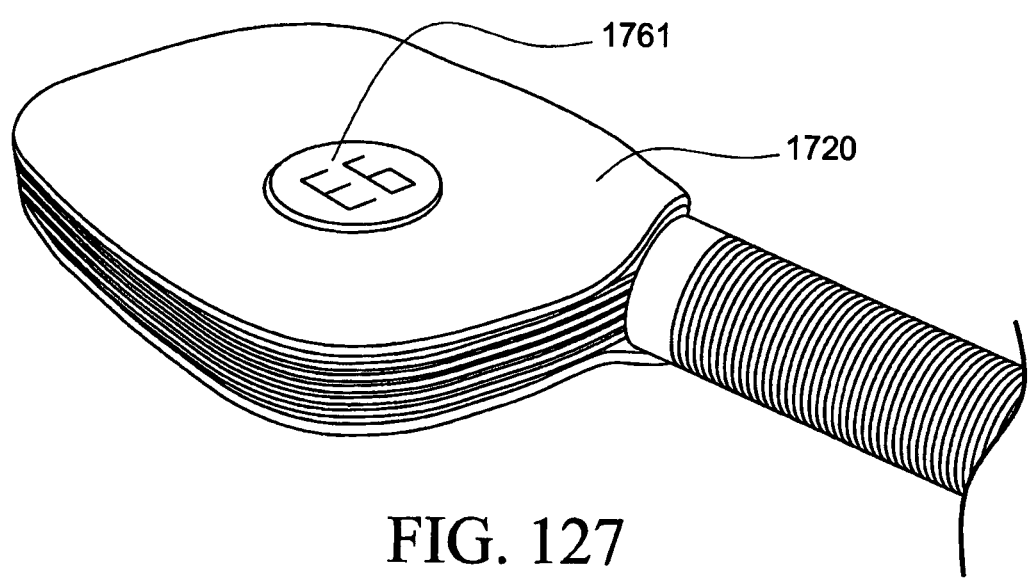
FIGS. 127 and 128 show the PAP device of FIG. 126 removed from the cover according to an example of the present technology.
Figure 128:
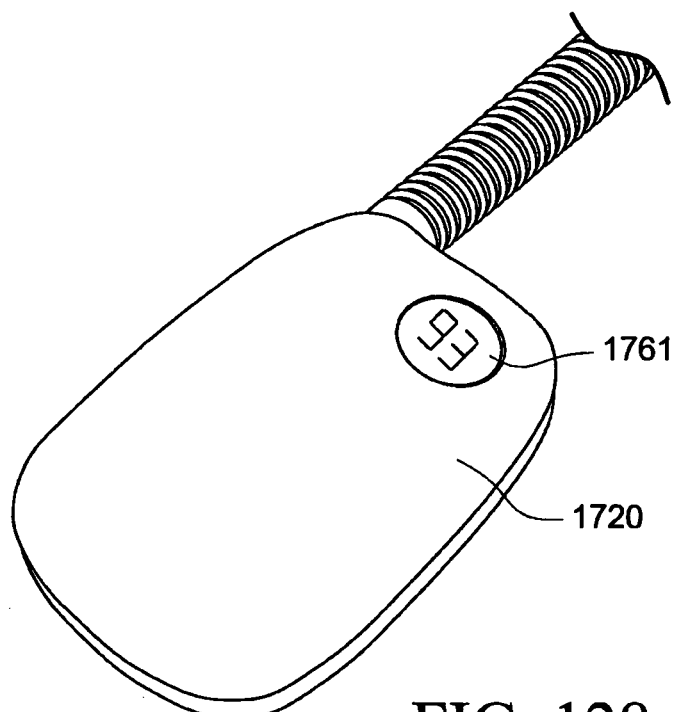

FIGS. 96, 97, and 98 show a PAP device 1720 and FIG. 99 shows such PAP device enclosed by a cover 1750 according to another example of the present technology. As illustrated, the PAP device 1720 includes an offset or asymmetrical outlet 1721 structured to communicate with the air delivery tube 1740. An overmolded, relatively soft interface button 1760 is provided to the top of the PAP device, e.g., soft to push. An LED display 1761, e.g., shows status using lights and/or icons, may be provided adjacent the button, e.g., see FIG. 97. In an alternative example, as shown in FIGS. 126 to 128, the display 1761 may include a numeric or digital display as described above and adapted to glow through the cover 1750 in use. The housing of the PAP device includes overmolded top and bottom housing parts 1727(1), 1727(2) (e.g., constructed of plastic) and a layered, intermediate portion 1727(3) between the housing parts. The air intake 1723 is folded in or otherwise provided within the layers of the intermediate portion, and is continuous around the perimeter.

The cover 1750 (e.g., constructed of a fabric material) includes an exterior button 1751 sewn to textile, which registers with the soft interface button below. A fitted fabric may be bonded on one side of the air delivery tube. A portion of the cover, e.g., end portion 1750(1), may include a silicone material, e.g., to keep the PAP device from moving in bed.

Figure 100:
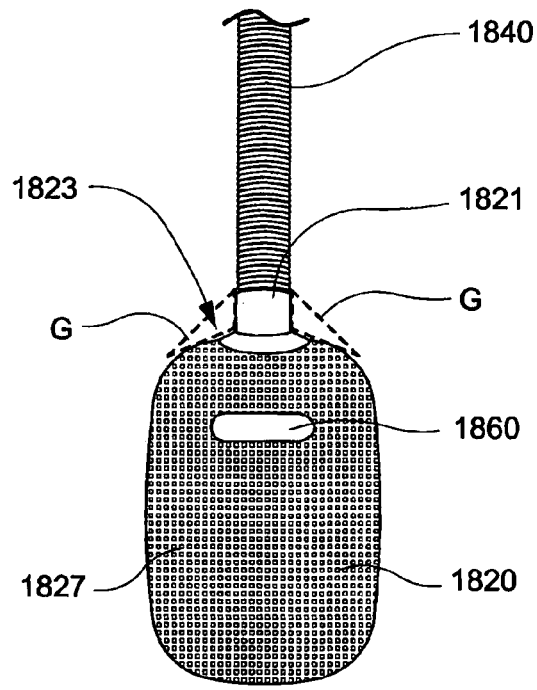
FIG. 100 shows a PAP device according to an example of the present technology.
Figure 102:
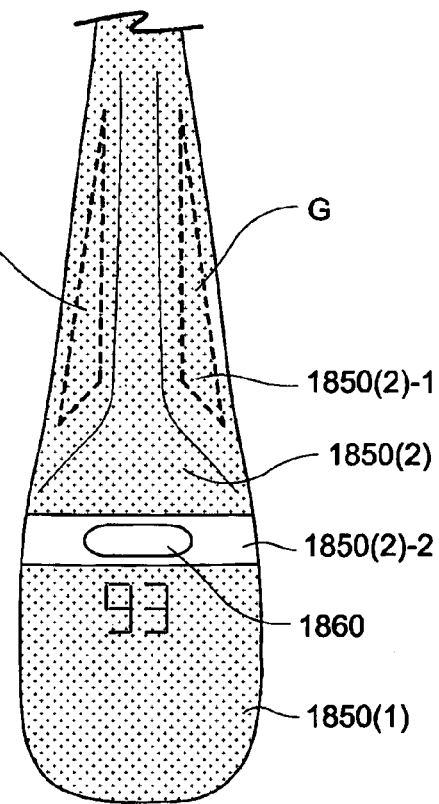
FIGS. 101 and 102 show the PAP device of FIG. 100 enclosed by cover portions according to an example of the present technology.
Figure 101:
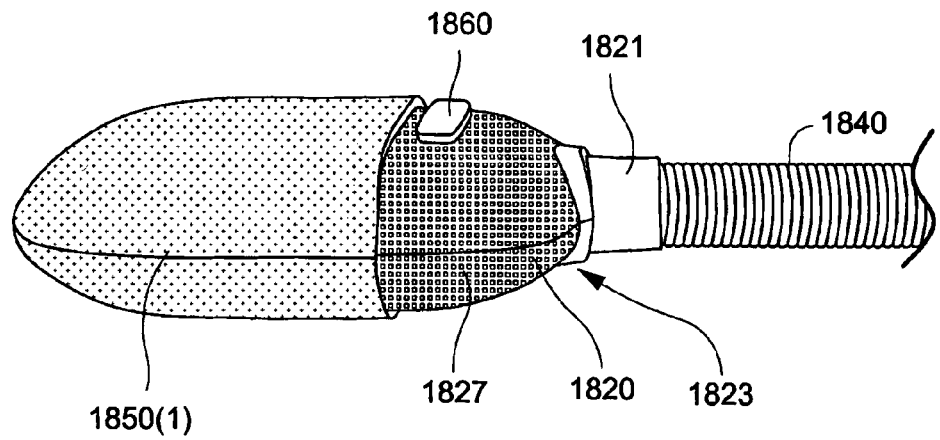

FIG. 100 shows a PAP device 1820 and FIGS. 101 and 102 show such PAP device enclosed by cover portions 1850(1) and 1850(2) according to another example of the present technology. As illustrated, the PAP device 1820 includes a central or symmetrical outlet 1821 structured to communicate with the air delivery tube 1840. A raised interface button 1860 is provided to the top of the PAP device and a numeric display may be provided below the button. The housing 1827 of the PAP device includes a continuous hole pattern which covers the blower, e.g., blind holes. The air intake 1823 is exposed near the outlet 1821 (i.e., some of the holes in the hole pattern of the housing are open while all other holes in the hole pattern are blind or closed).

A cover portion 1850(1) is in the form of a translucent silicone sleeve which fits over the lower portion of the PAP device. The silicone sleeve provides grip, e.g., to keep the PAP device from moving in bed, and also reveals the hole pattern of the housing. The numeric display glows through the hole pattern and the silicone sleeve, e.g., see FIG. 102. The cover portion 1850(2) includes a fabric cover 1850(2)-1 that covers the upper portion of the PAP device and a silicone band 1850(2)-2 that stretches over the button 1860 and housing to secure the cover in position. The fabric cover of the cover portion 1850(2) may be bonded on both sides of the air delivery tube.

Figures 1, 148:
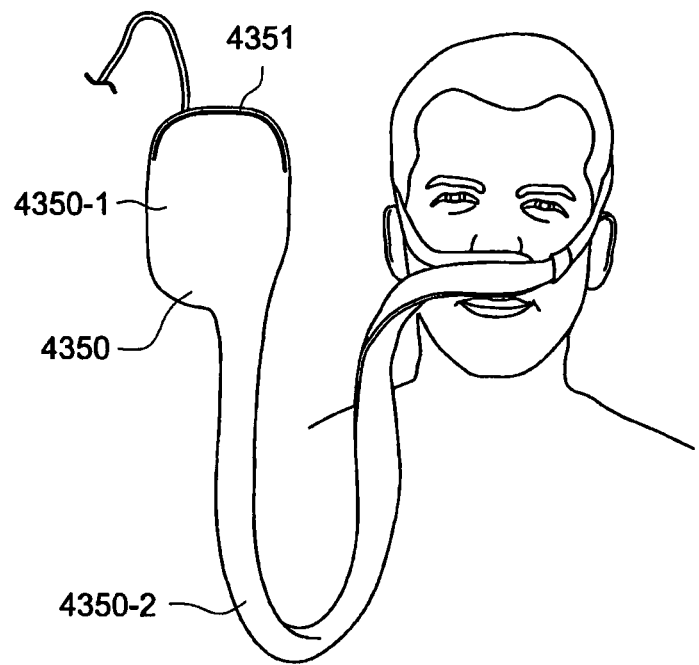
Figures 2, 148:
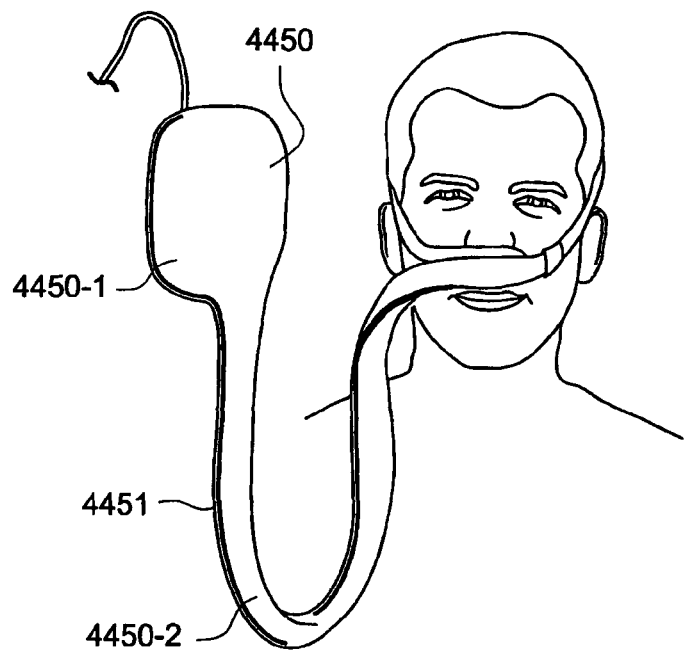
Figures 3, 148:
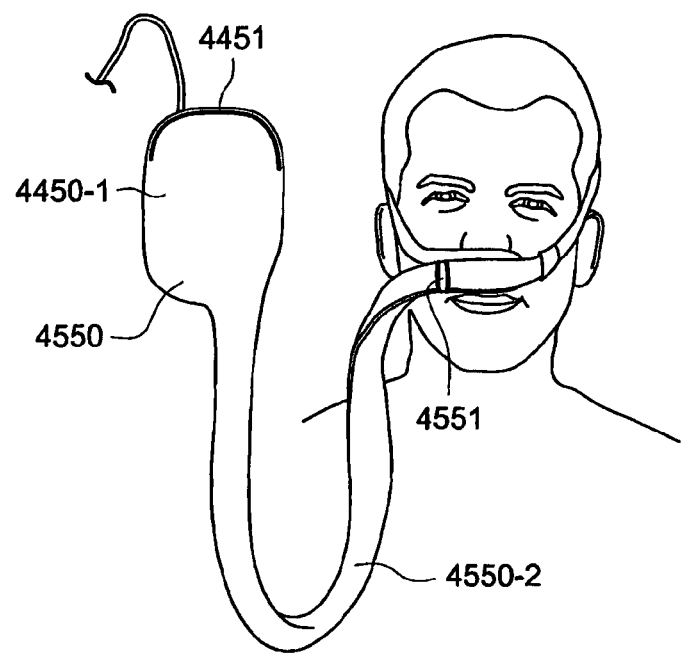

FIGS. 106 to 125 show a PAP system according to another example of the present technology. As illustrated, the PAP system includes a PAP device 2120, a patient interface 2130 (e.g., including nasal cushion or nasal interface (see FIG. 117)), and air delivery tubing that interconnects the patient interface and the PAP device. A cover 2150 substantially encloses the PAP device and the air delivery tubing. Also, headgear 2170 supports the patient interface in position. In an example, at least a portion of the exterior surface of the tubing (and/or the interior of the pouch portion) may be relatively slippery (e.g., lower friction surface) to facilitate assembly of the tubing through the opening 4351 of the pouch portion 4350-1 and into the tube portion 4350-2 of the cover 4350 (e.g., FIG. 148-1). In another example, a zipper 4451 or other releasable attachment mechanism may be provided along a length of the cover 4450 (e.g., along a side of the pouch portion 4450-1 and tube portion 4450-2 of the cover) to allow easy access to connect and assemble the tube within the cover (e.g., FIG. 148-2). In another example, the cover 4550 may include one or more splits 4551 along its length to facilitate assembly of the tubing into the cover, e.g., split 4551 along end of pouch portion 4550-1 and split 4551 along end of tube portion 4550-2 (e.g., FIG. 148-3).

Figure 108:
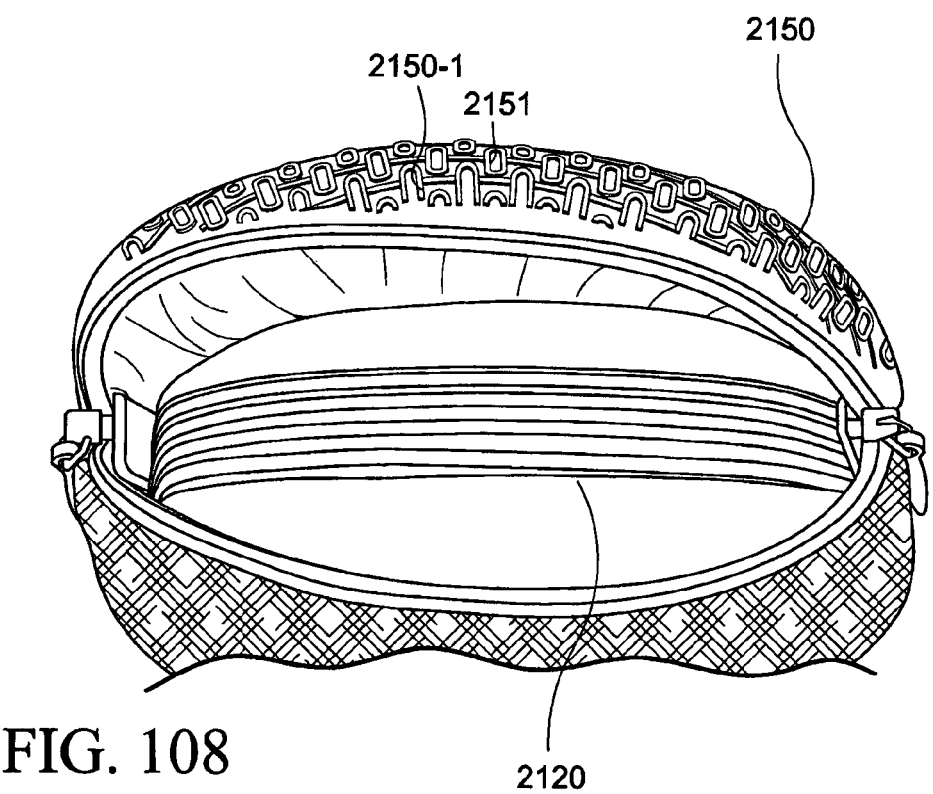
Figure 109:
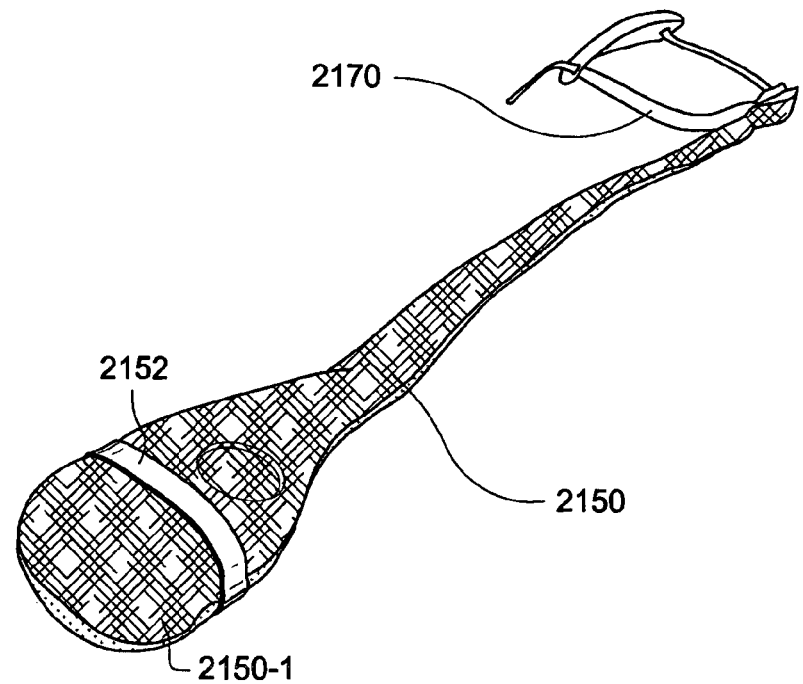
Figure 110:
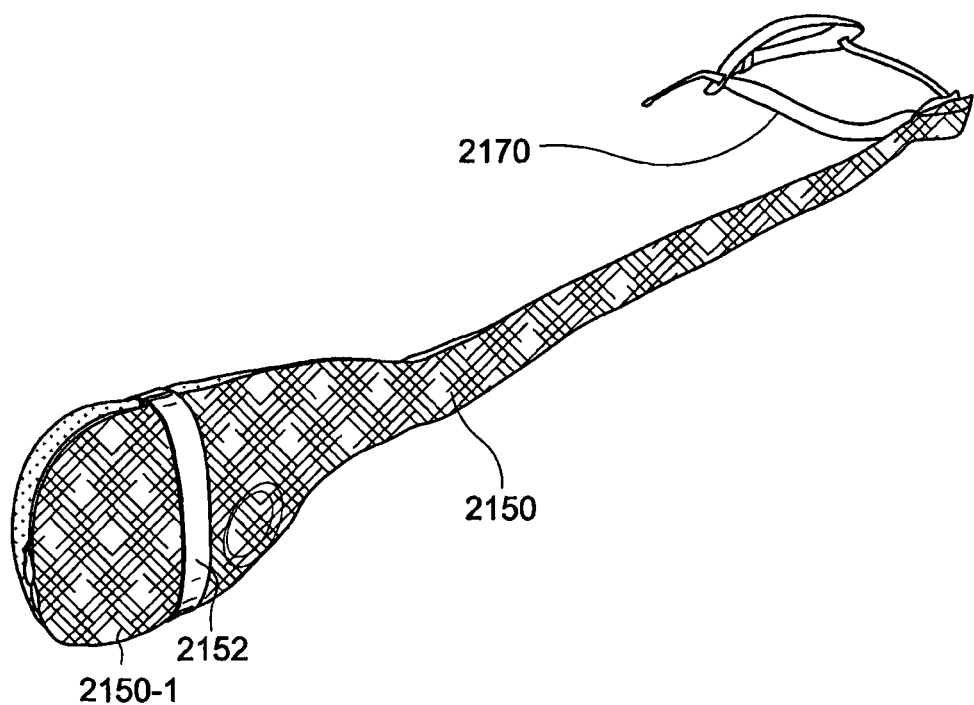
Figure 111:
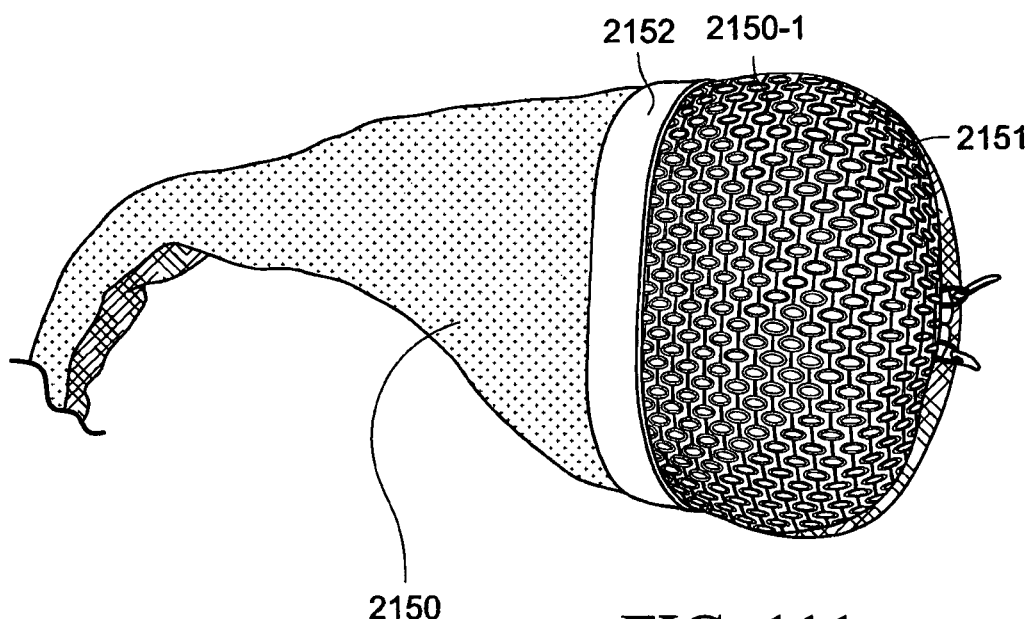
Figure 112:
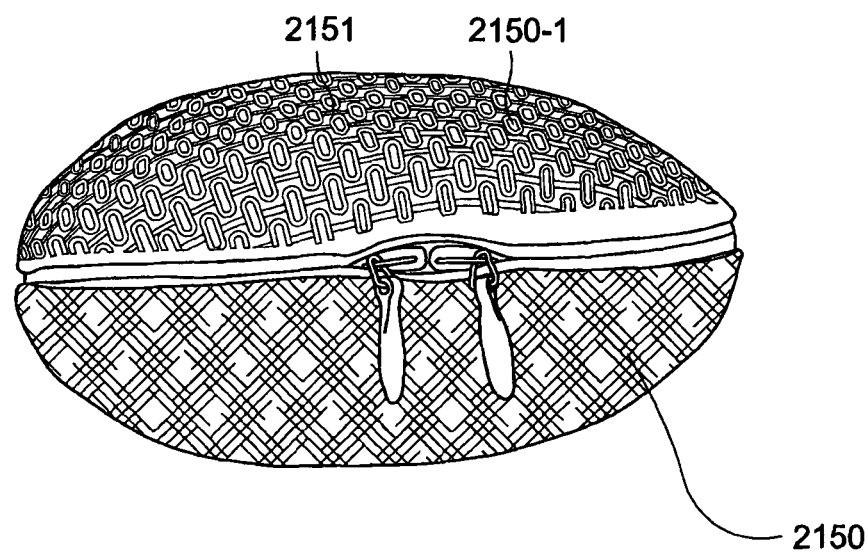
Figure 113:
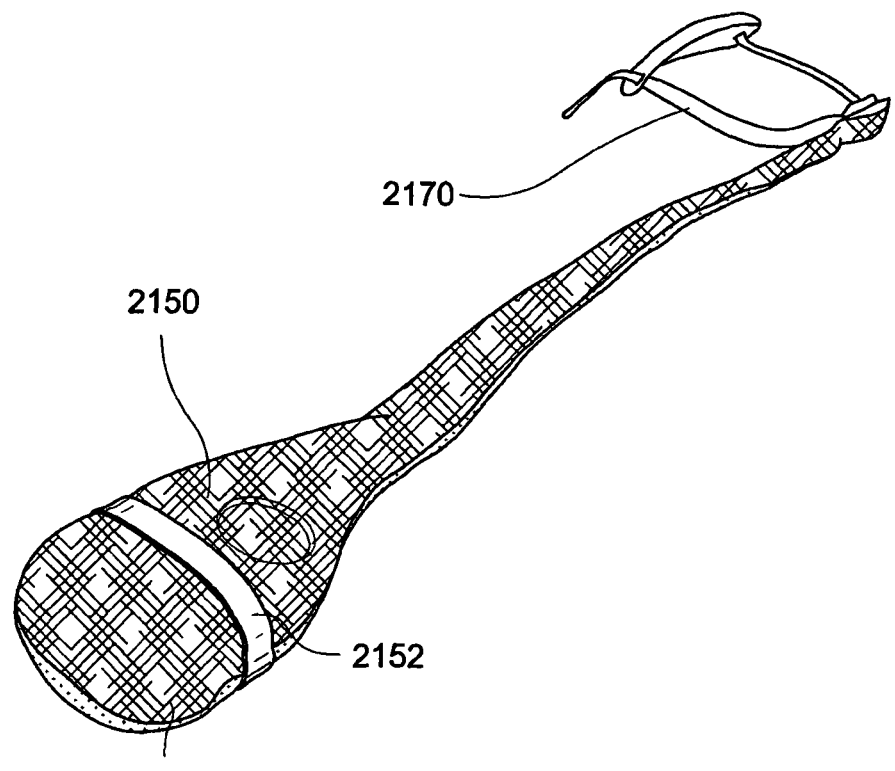
Figure 114:
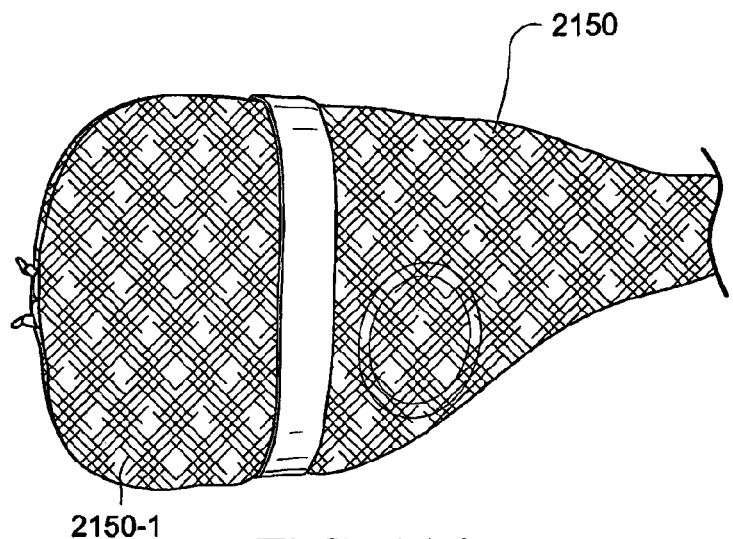
Figure 115:
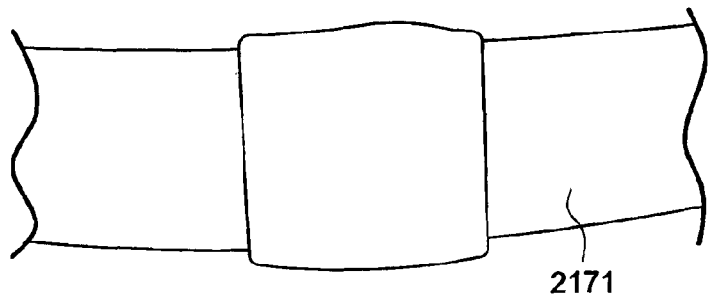
Figure 116:
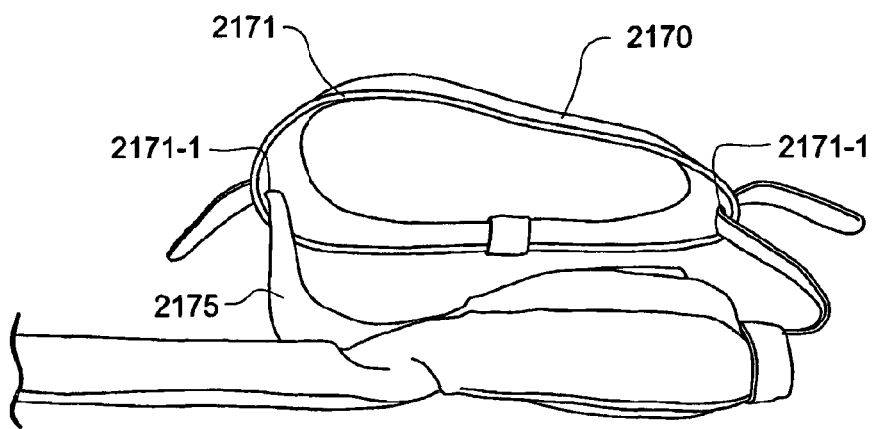

As best shown in FIGS. 108 and 112, the pouch portion 2150-1 of the cover enclosing the PAP device includes a zipper or other suitable closure device to allow easy access to the PAP device. Also, at least one side of the pouch portion may include a non-slip pattern 2151 (e.g., see FIGS. 108, 111, 112, 124, 125) to help maintain the pouch portion in position on a surface (e.g., bed sheets) in use. Also, an elastic band or strip 2152 (e.g., cobalt nylon lycra strip) may be provided along the pouch portion, e.g., to help locate and secure the PAP device within the pouch portion (e.g., see FIGS. 113, 124, 125). The headgear 2170 includes a generally circular rear strap 2171 (e.g., see FIGS. 115, 116, 121 and 122) that provides a "halo" type arrangement adapted to engage the patient's head, i.e., capture the crown of the patient's head in use. A front strap 2175 extends from the rear strap to support the patient interface. The rear strap includes slots 2171-1 on opposing sides thereof (e.g., see FIGS. 116, 118, 119, and 121) adapted to adjustably and releasably engage ends or side strap portions of the front strap, e.g., via a hook and loop fastening arrangement. The positioning of the slots 2171-1 (e.g., along the sides of the "halo" or loop type arrangement, e.g., see FIG. 121) is selected to properly orient and position the front strap 2175 to ensure correct functioning and tensioning vectors for sealing. The side strap portions of the front strap may include a rigidizer or stiffening element to add rigidity to the side strap portions for stably supporting the patient interface in position, e.g., similar to the circular rear strap 1071 and rigidized side strap portions 1072(1) shown in FIG. 66.

Figure 117:
Figure 118:
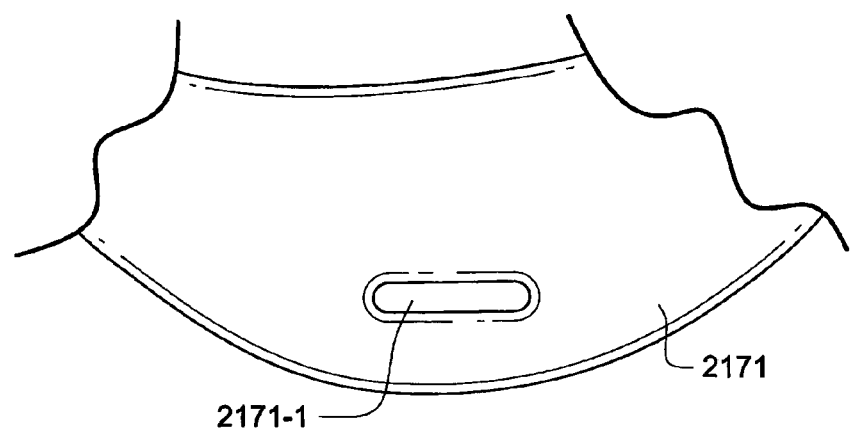
Figure 119:
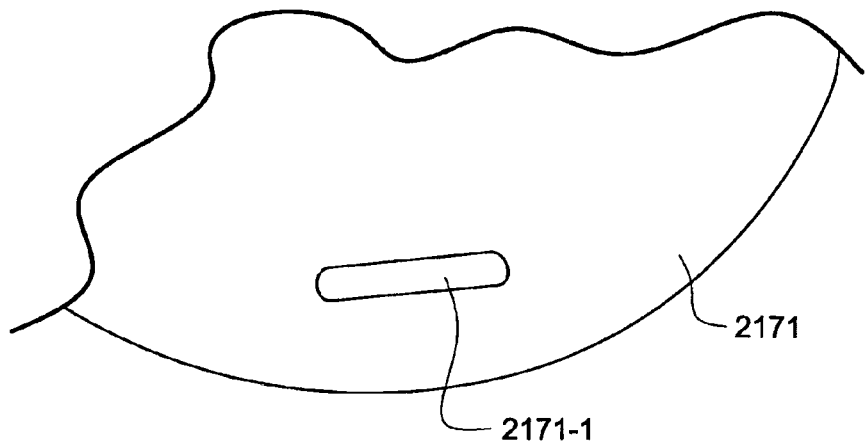
Figure 120:
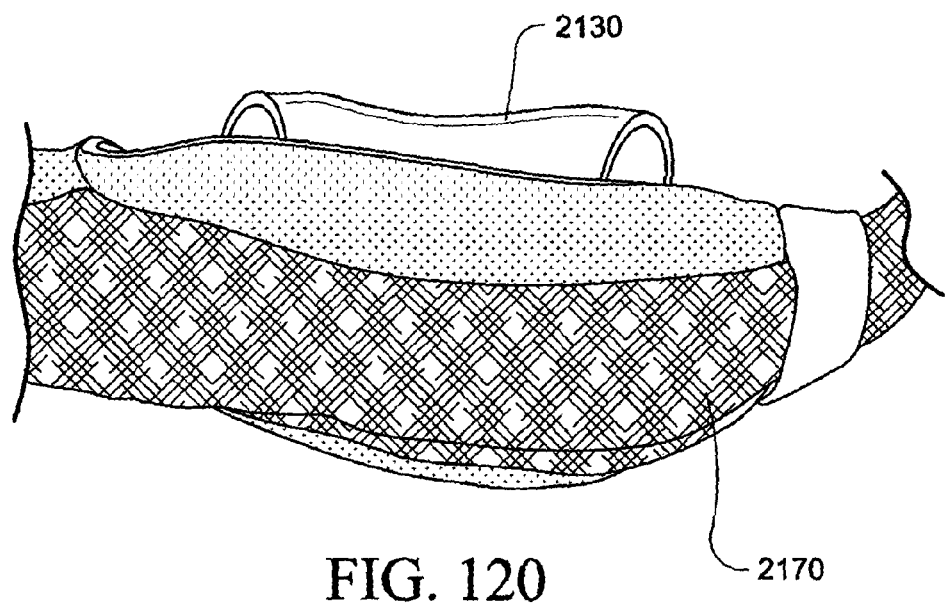
Figure 121:
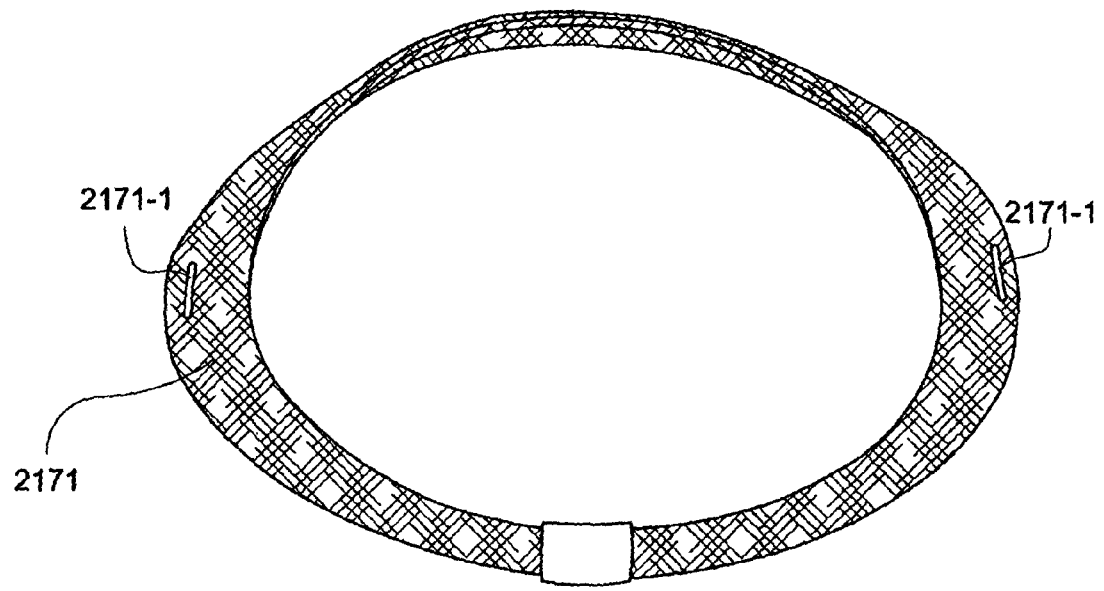
Figure 122:
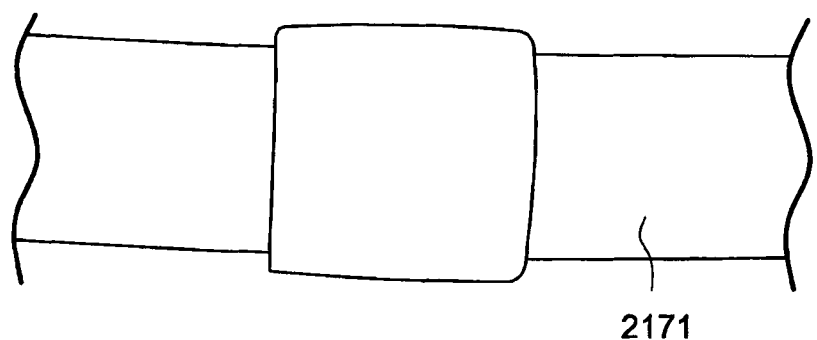
Figure 123:
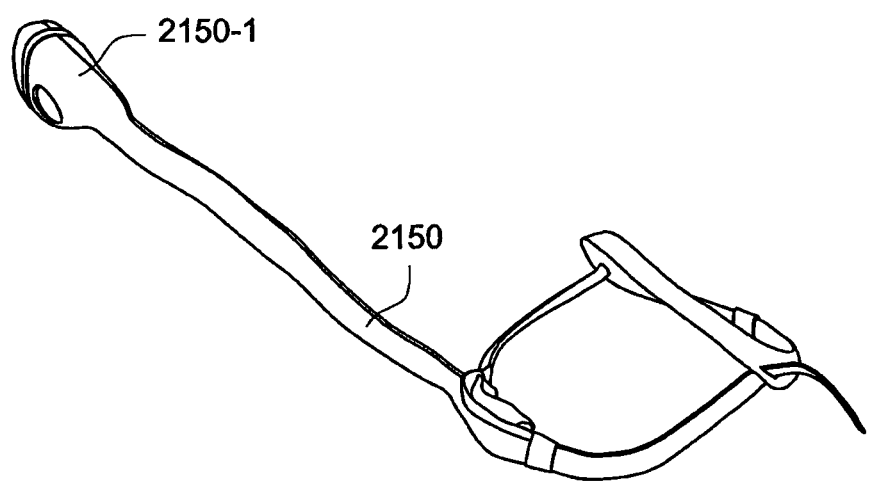
Figure 124:
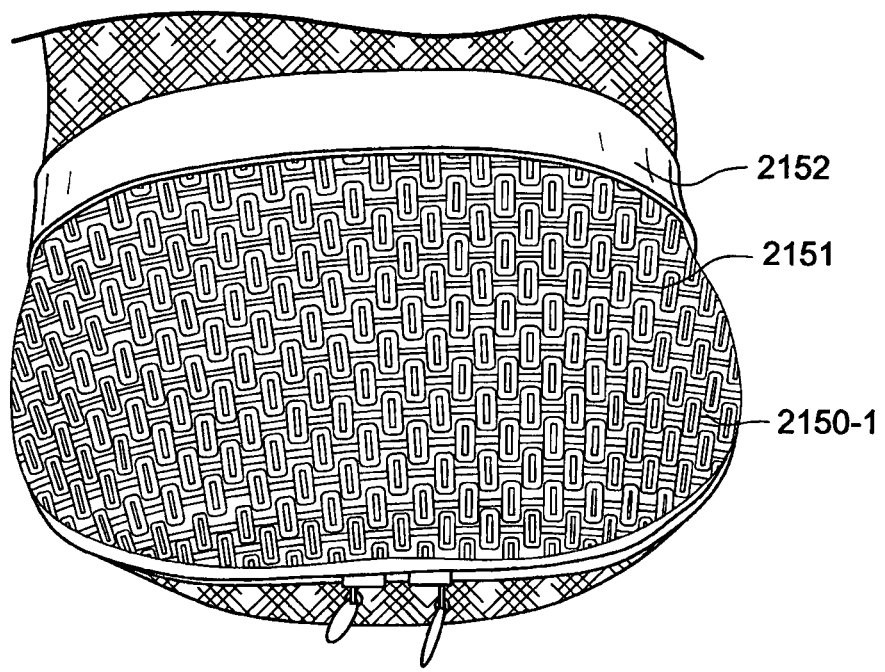
Figure 125:
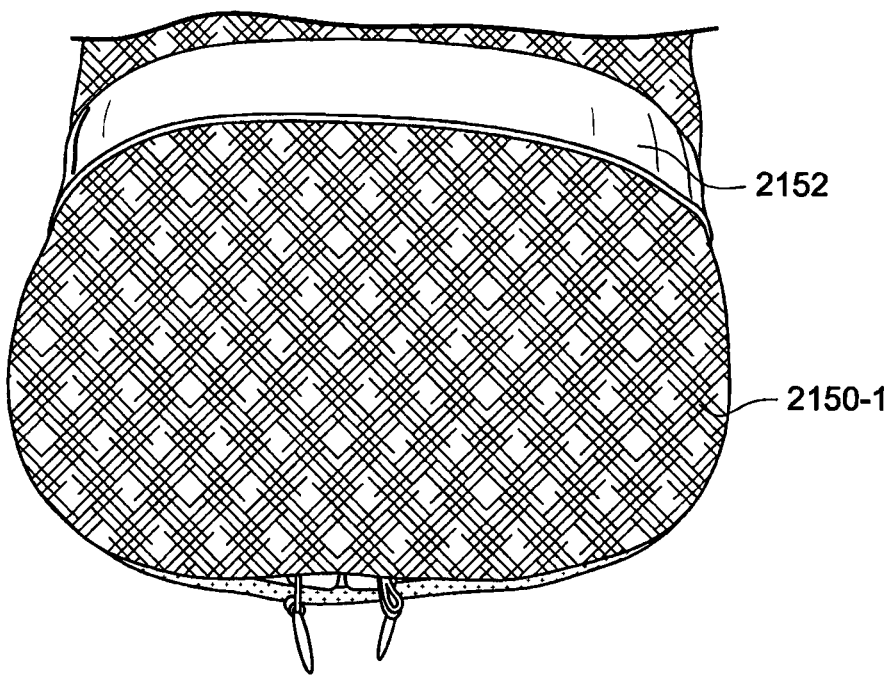

FIGS. 117 and 120 show the patient facing and outer facing portions respectively of the PAP system that is adapted to engage a patient's face. The patient interface 2130 may include a nasal cushion or nasal interface that seals against the patient's face in use. The headgear 2170 wraps across the outer surface over the patient interface 2130.

Figure 180:
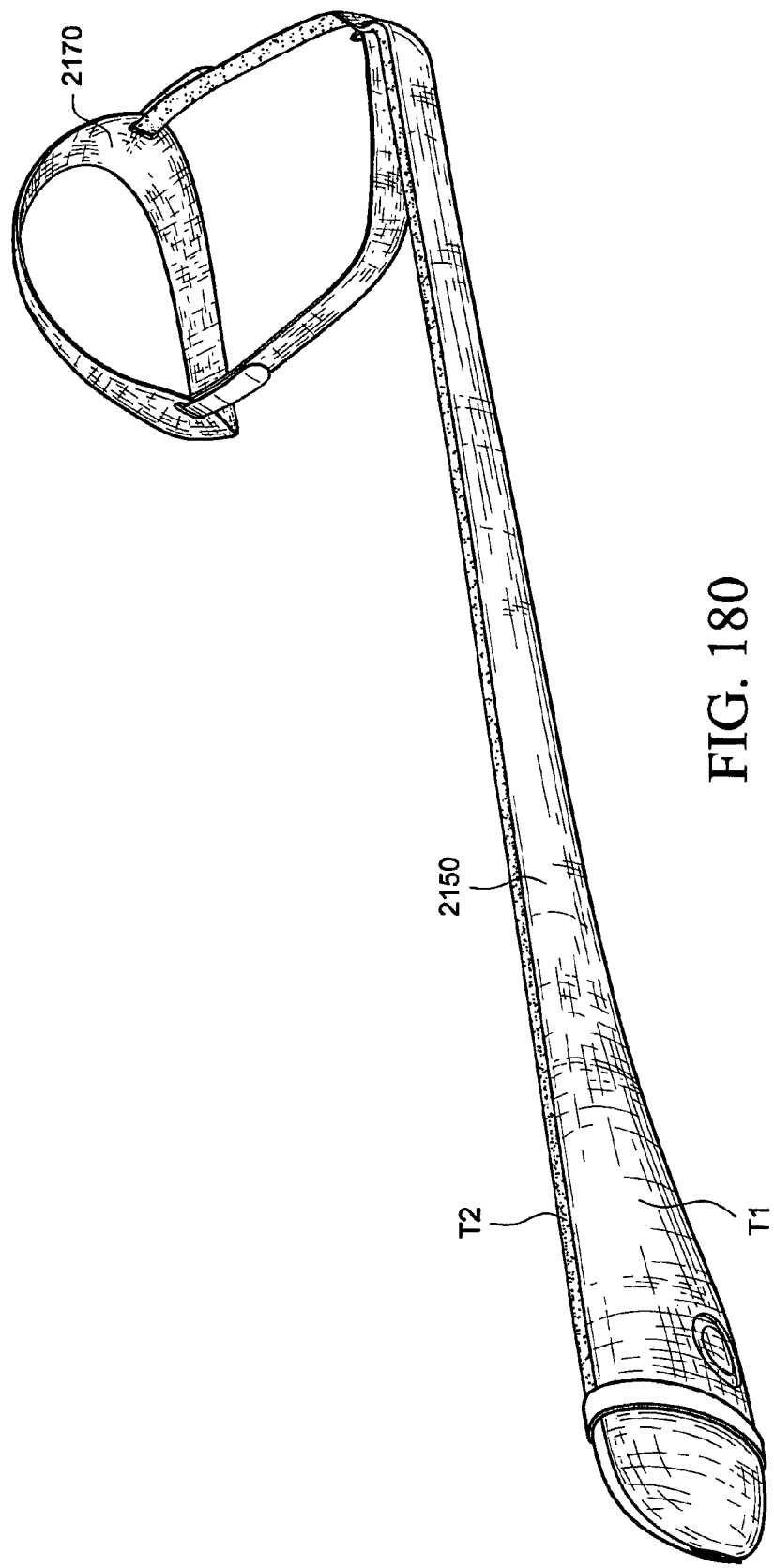
FIGS. 180-182 show various views of a PAP system according to an example of the present technology.
Figure 181:
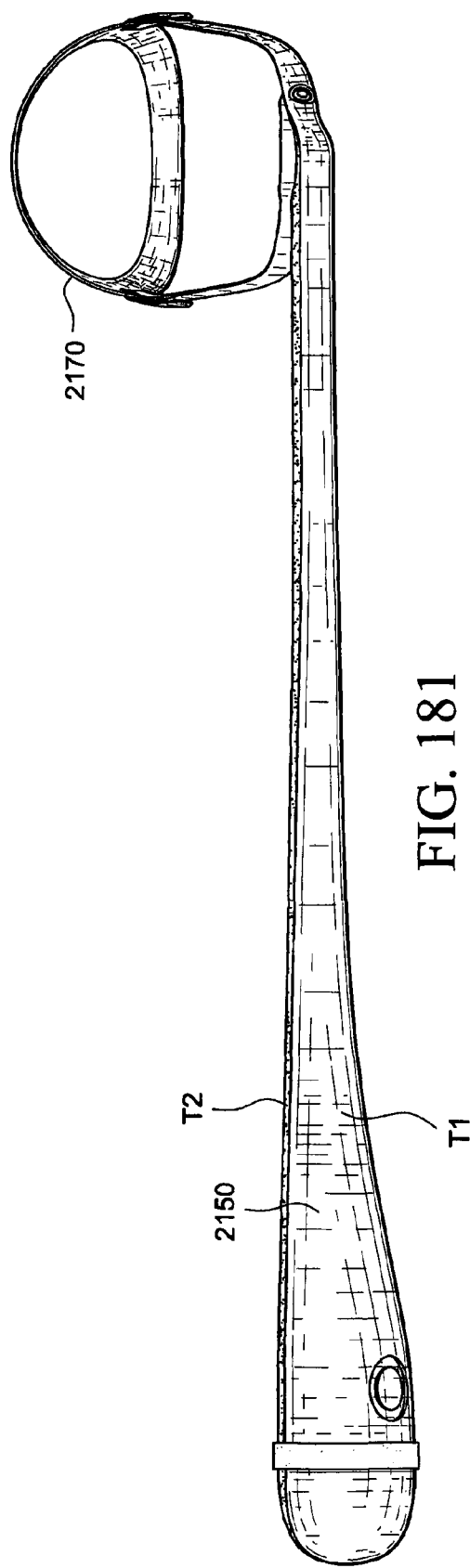
Figure 182:
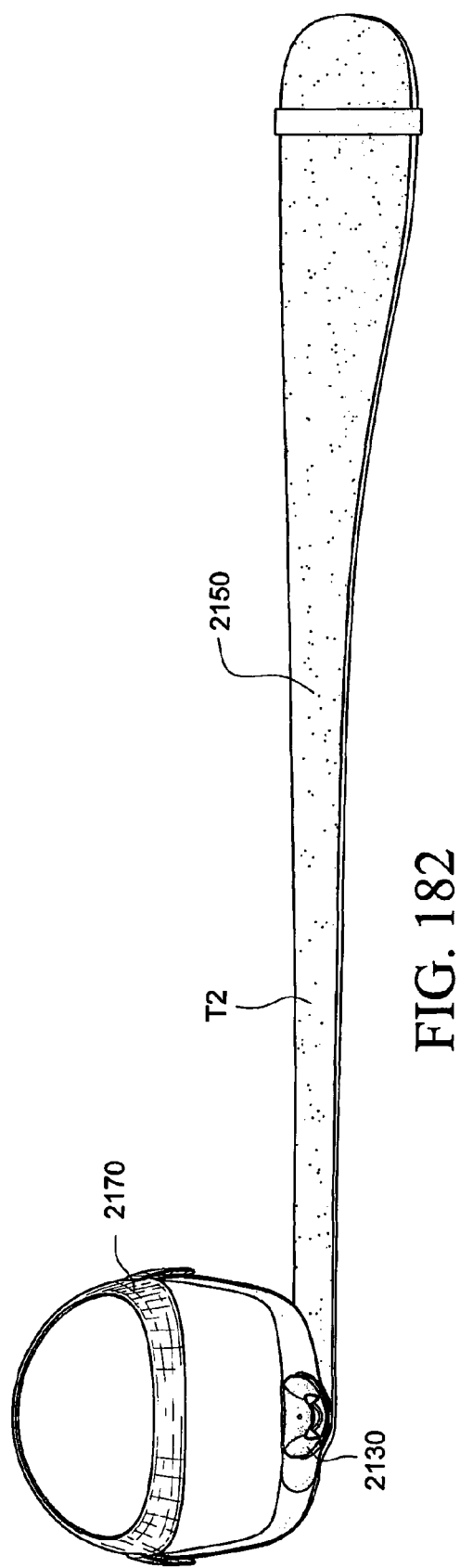
Figure 183:
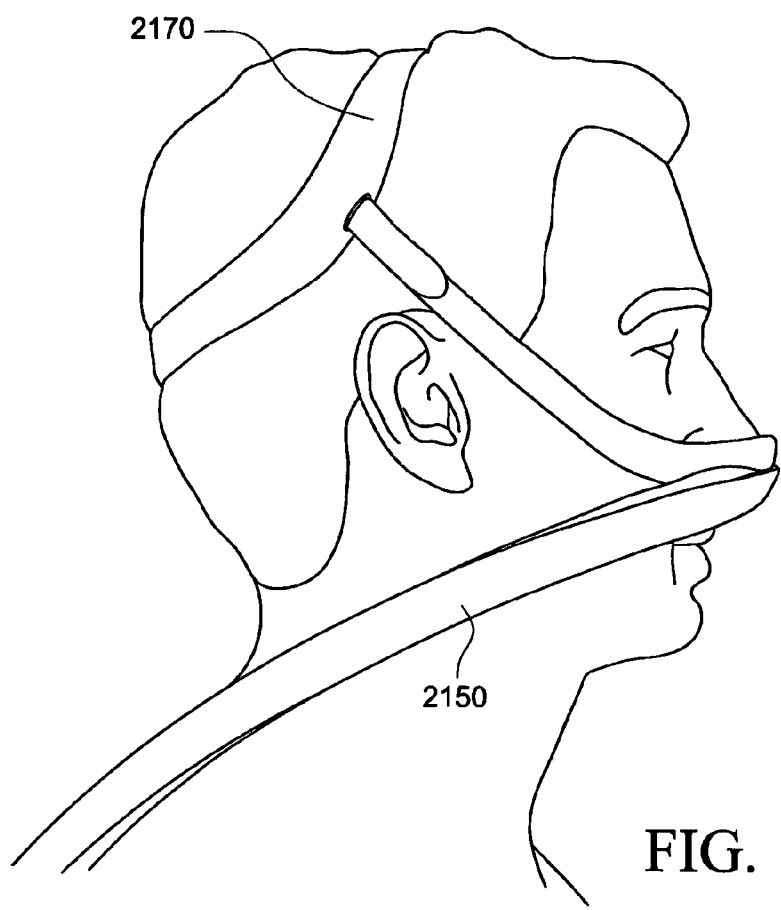
FIGS. 183-189 show various views of a PAP system according to an example of the present technology.
Figure 184:
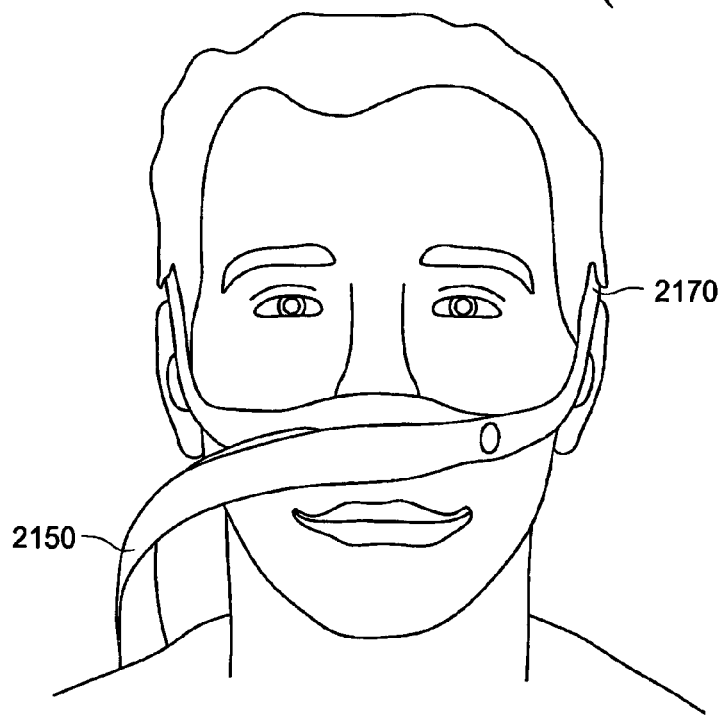

FIGS. 180 to 182 show alternative views of the cover 2150, headgear 2170, and patient interface 2130 of the PAP system described above. The cover 2150 completely encloses the entire system to provide an impression of an all-in-one or complete system rather than separate components. The cover may also reduce the medical look of the system and hide, veil or conceal the connection points between the different components of the system, such as, the patient interface, air delivery tubing and PAP device connection points. As shown, the system may have different textiles, e.g., textile T1 and textile T2, on opposing sides of the system that may assist in orienting the system. The type of textile may be selectable by the patient.

Figure 185:
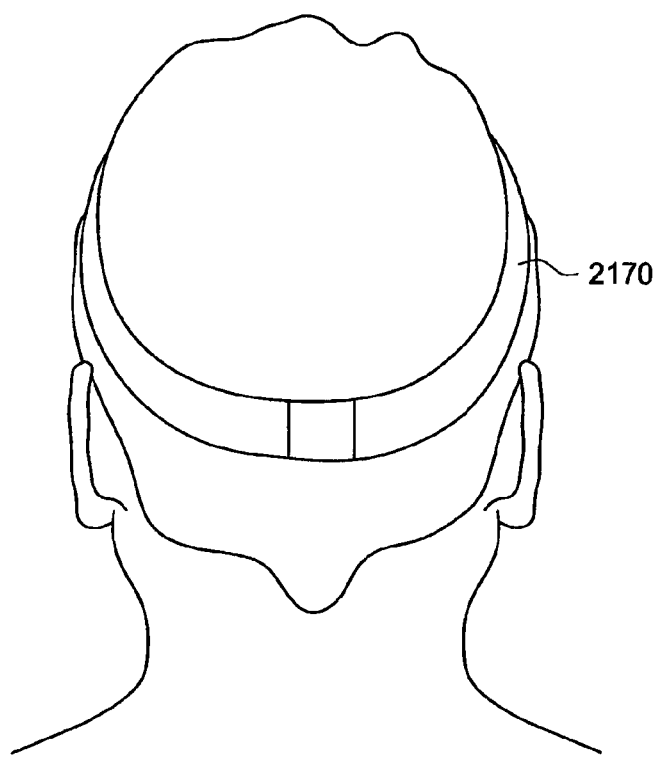
Figure 186:
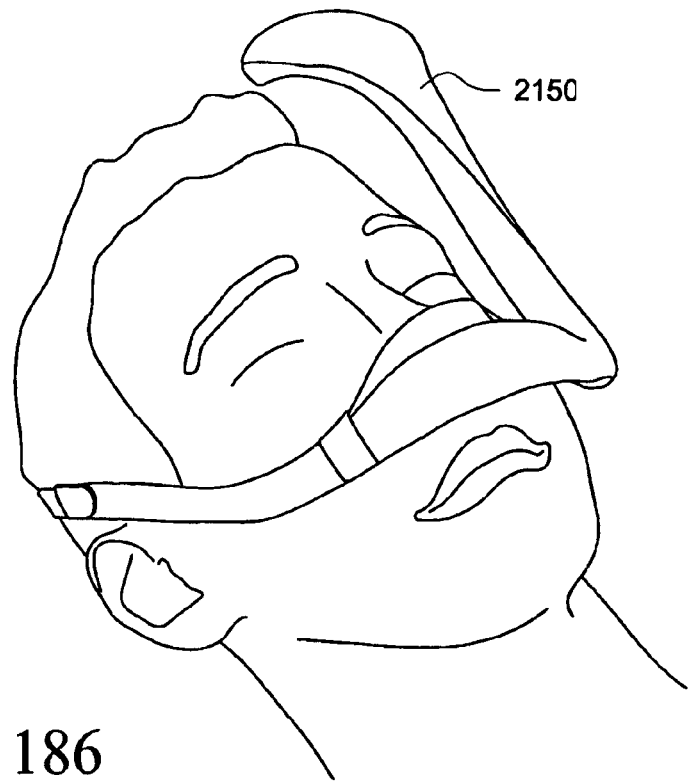
Figure 187:
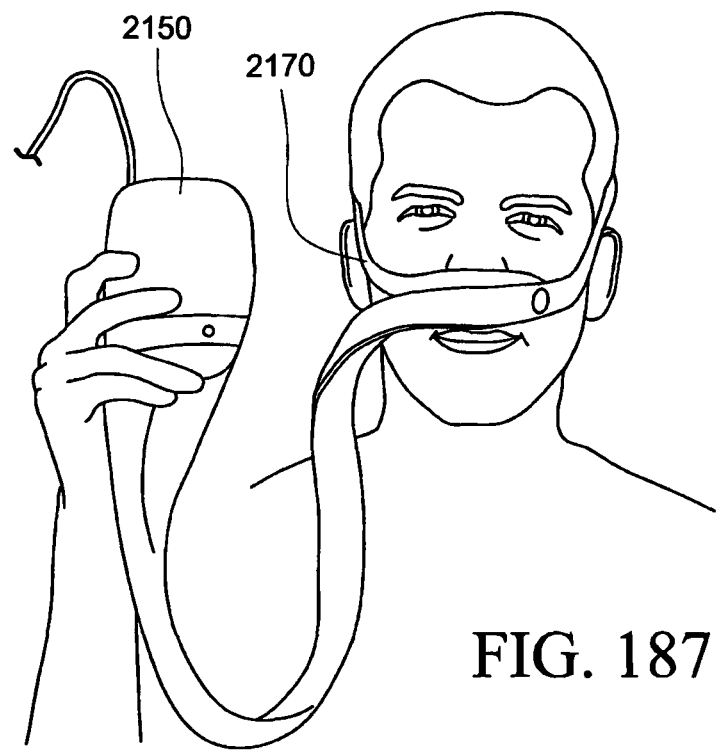
Figure 188:
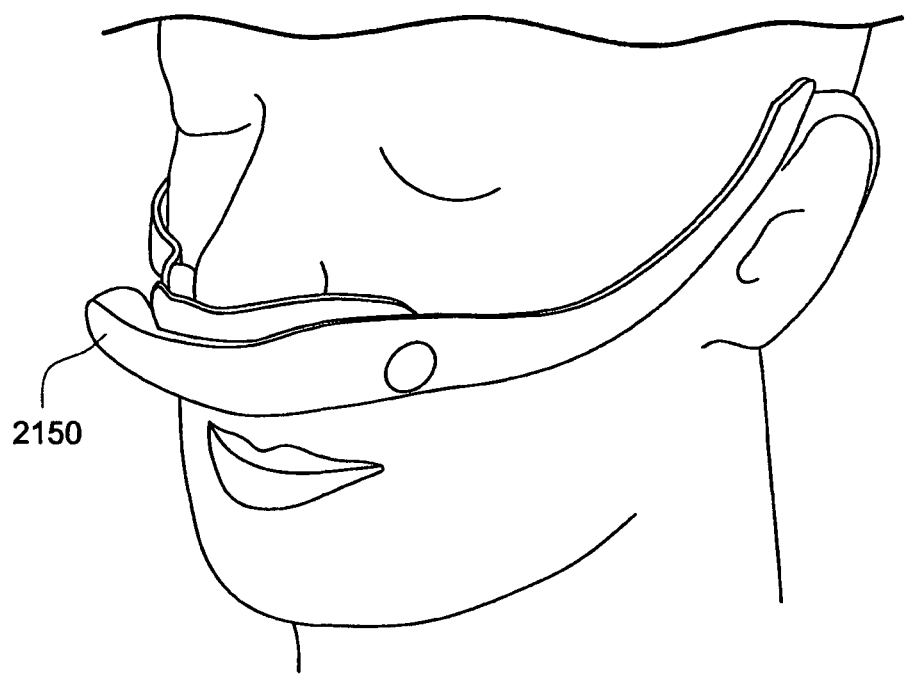
Figure 189:
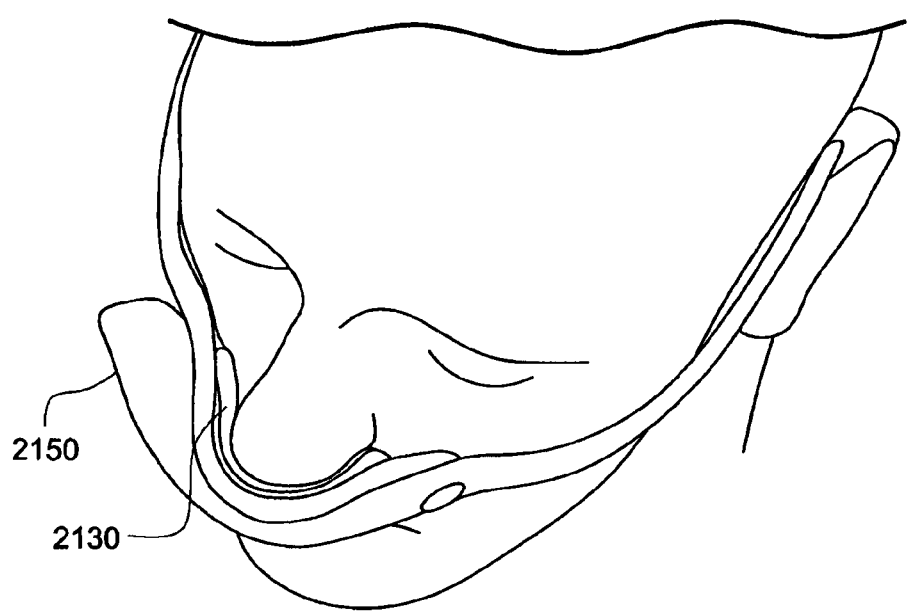

FIGS. 183 to 189 also show alternative views of the cover 2150, headgear 2170, and patient interface 2130 of the PAP system described above, and show the PAP system in position with the patient interface and a portion of the air delivery tubing on a patient's head and the PAP device portion within the scarf-like cover located over the patient's shoulder when the patient is in the upright position (FIGS. 183-184) and beside the patient (FIG. 186) when the patient is in the supine position. A back headgear strap supports the patient interface 2130 and a portion of the air delivery tubing within the cover 2150 on the face as seen in FIG. 185. FIG. 187 illustrates the patient holding the PAP device portion of the PAP system within the cover 2150. The advantage of the wrap or scarf-like arrangement means that the system is more portable, small, and lighter to allow the patient to freely move around even when connected to the system. FIGS. 188 and 189 illustrate the patient interface arrangement and the connection to the cover 2150.

Figure 190:
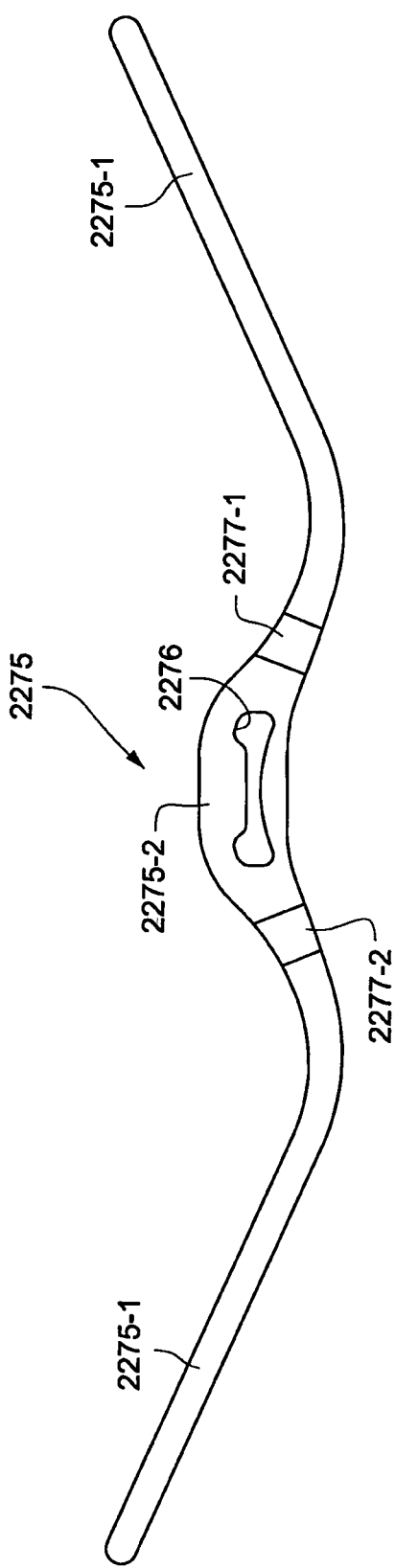
FIGS. 190 and 191 show back and front views of headgear according to an example of the present technology.
Figure 191:
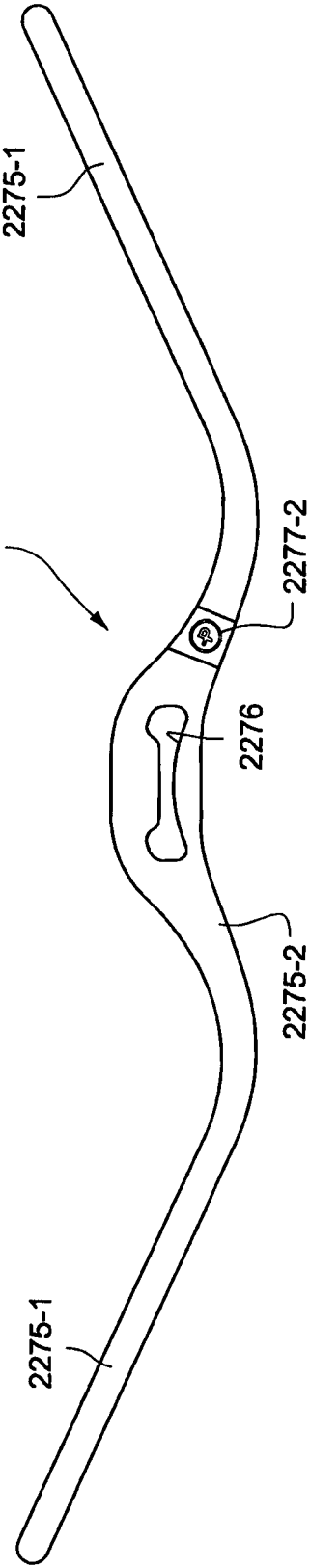

FIGS. 190 and 191 show an example of a front strap for headgear according to an example of the present technology. As illustrated, the front strap 2275 includes side strap portions 2275-1 adapted to engage respective slots on opposing sides of the "halo" type rear strap described above, e.g., via hook and loop fastening arrangement. The side strap portions may be compressed (e.g., 2 mm thickness) to facilitate insertion through the slots. The central portion 2275-2 of the front strap is structured to support the patient interface (e.g., nozzle arrangement, nasal cushion) and includes an opening 2276 that allows air delivery tubing to communicate with the patient interface. Sides of the central portion may include a tag 2277-1 and/or tube member 2277-2 wrapped around the strap (e.g., constructed of cobalt nylon lycra and attached by ultrasonic welding), e.g., for identifying information and/or for retaining portions of the cover in use.

Figure 163:
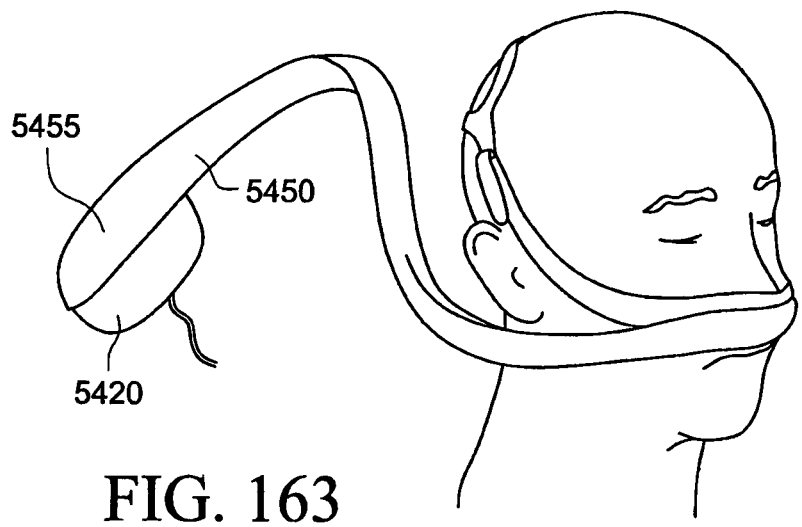
FIG. 163 shows a PAP system with a cover according to another example of the present technology.

In an alternative example, the cover may be structured to only cover a portion of the PAP device while leaving the remaining portion of the PAP device exposed. For example, FIGS. 159 to 162 illustrate examples of covers 5350 including a strap portion 5355 adapted to wrap around the PAP device 5320 and FIG. 163 illustrates an example of a cover 5450 including a pouch 5455 adapted to receive and enclose a side of the PAP device 5420.

8.1 Occlusion Prevention

As shown in FIGS. 96, 98, 100, and 101, at least a portion of the air intake to the PAP device is provided adjacent to the outlet or outlet tube. If the PAP device is used without a cover, the outlet tube protrudes sufficiently past the air intake to engage bed sheets or other obstructions and create a small gap or gaps surrounding the air intake, e.g., gap or gaps G shown in FIGS. 96 and 100. Such gaps prevent occlusion of the air intake in use, e.g., if the PAP device is covered by bed sheets.

If the PAP device is used with a cover as shown in FIGS. 99 and 102 for example, the cover is bonded to the air delivery tube or otherwise formed to create a gap or gaps within the cover adjacent to the air intake, e.g., gap or gaps G in cover shown in FIGS. 99 and 102, to prevent occlusion. The gaps may also help to muffle or suppress noise. In addition, the fabric material of the cover may help to muffle or suppress noise. It should be appreciated that the cover is constructed of fabric or other suitable materials (e.g., weave, layers, etc.) that allow air therethrough to the air intake.

9. Exemplary PAP Device

In an example, the PAP device includes a housing that encloses a blower for generating a supply of pressurized air and other internal components. For example, along with the blower, the housing encloses or otherwise supports a suspension device, driver circuitry, a user interface, a power supply (e.g., battery or direct), a filter, a dampening device (e.g., foam), and/or a bladder.

Figure 103:
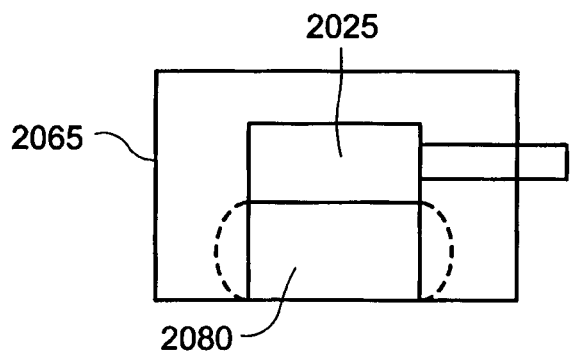
FIG. 103 is a schematic view of a bladder for a blower according to an example of the present technology.

As schematically shown in FIG. 103, the blower 2025 within housing 2065 may be communicated with a bladder 2080 structured to expand and contract in response to patient expiration and inspiration. For example, the bladder 2080 may expand (e.g., as shown in dashed lines) during patient expiration (e.g., due to back flow) and subsequently contract during patient inspiration (e.g., contraction of bladder may provide bolus of air to patient).

Such bladder arrangement may allow the use of a constant speed blower, as the bladder helps deal with expiratory positive airway pressure (EPAP), inspiratory positive airway pressure (IPAP), pressure swings, etc.

Figure 104:
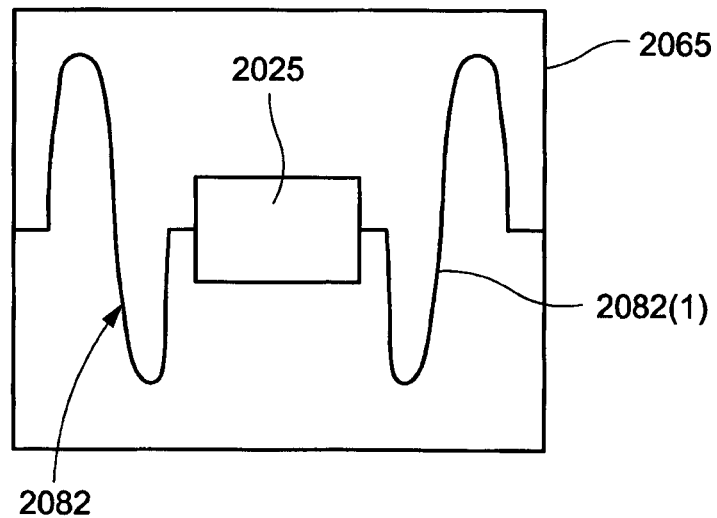
FIG. 104 is a schematic view of a suspension device for a blower according to an example of the present technology.

As schematically shown in FIG. 104, the blower 2025 may be supported within the housing 2065 by a suspension device 2082, e.g., constructed of silicone, to keep the blower out of contact with the housing and allow movement of the blower with respect to the housing in use. In an example, the suspension device 2082 may be integrated with the bladder 2080. As illustrated, the suspension device 2082 includes generally S-shaped support members 2082(1) structured to absorb shock applied to sides of the housing as well as top and bottom walls of the housing, e.g., absorb shock applied both axially and radially.

In an example, the suspension device includes an overall exterior shape that substantially matches the shape of the housing interior. However, the suspension device may include other suitable shapes that may not correspond to the housing shape, e.g., suspension device includes a general cylindrical shape while housing includes a general rectangular shape. Also, the suspension device may include one or more side walls with windows or openings to reduce material and help avoid resonant frequency and its associated vibrations.

Figure 105:
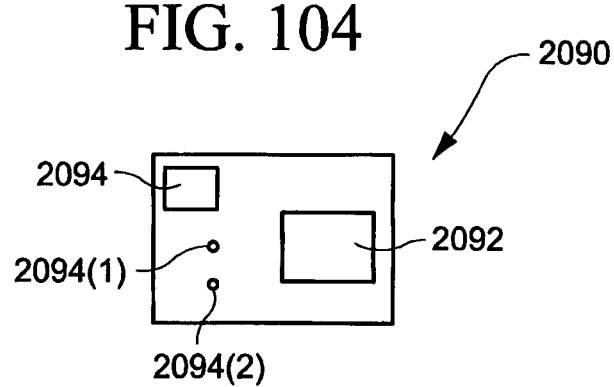
FIG. 105 is a schematic view of a printed circuit board according to an example of the present technology.
Figure 106:
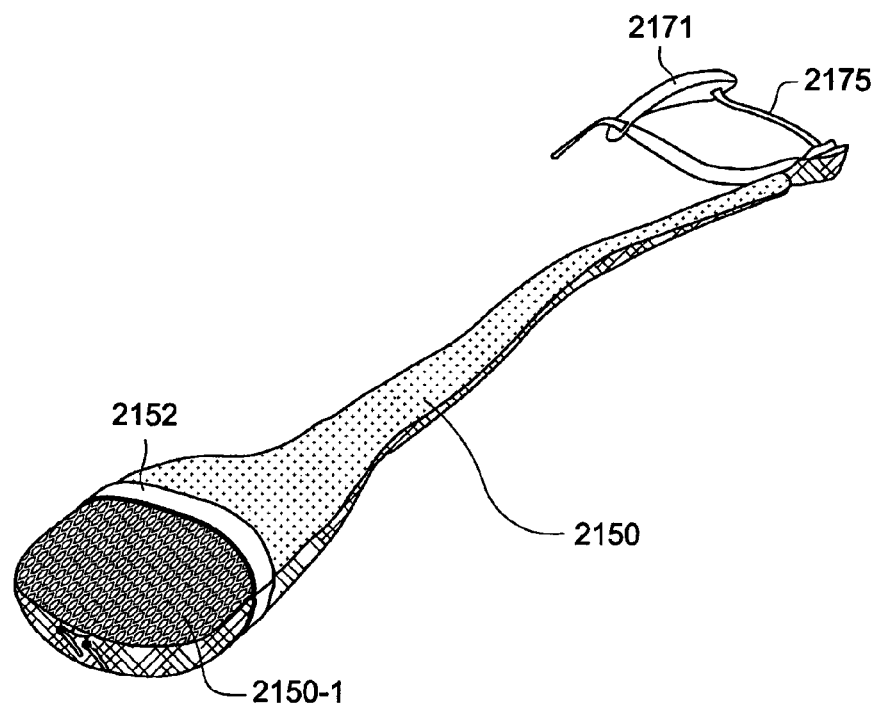
FIGS. 106 to 125 show a PAP system according to another example of the present technology.
Figure 107:
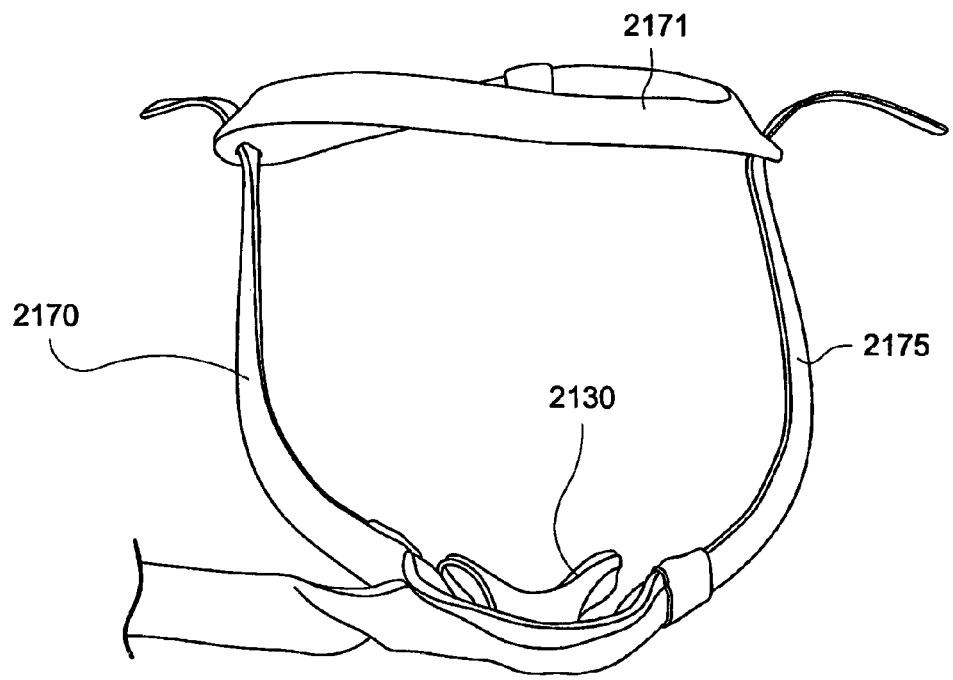

FIG. 105 schematically shows a printed circuit board (PCB) 2090 including driver circuitry 2092 for controlling the blower and a user interface, e.g., display 2094, user inputs, etc. In an example, the PCB may include one or more monitors to monitor the patient, e.g., temperature sensor 2094(1), microphone 2094(2), etc. The microphone is preferably but not necessarily provided in the air flow path.

10. Evaluation Result

In an example, a microphone may monitor the patient's breathing and noises imparted while the patient sleeps, e.g., snoring, and provide such information to a controller which determines a result or evaluation (e.g., snore evaluation result, quiet evaluation result, snore index, AHI, etc.) based on such information, i.e., diagnosis of problems. For example, the controller may analyze the amplitude and duration of the patient's snoring (e.g., detect snores in frequency band between 0-250 Hz, e.g., 30-150 Hz, or 50-150 Hz) and generate a result based on such analysis, such result being provided to the patient so the patient can determine whether the current PAP system is appropriate for the patient or whether to adjust treatment, e.g., raise or lower pressure, and/or consult a physician or dentist for different treatment, e.g., different PAP system, CPAP system providing more pressure, mandibular advancement device, etc.

Figure 201:
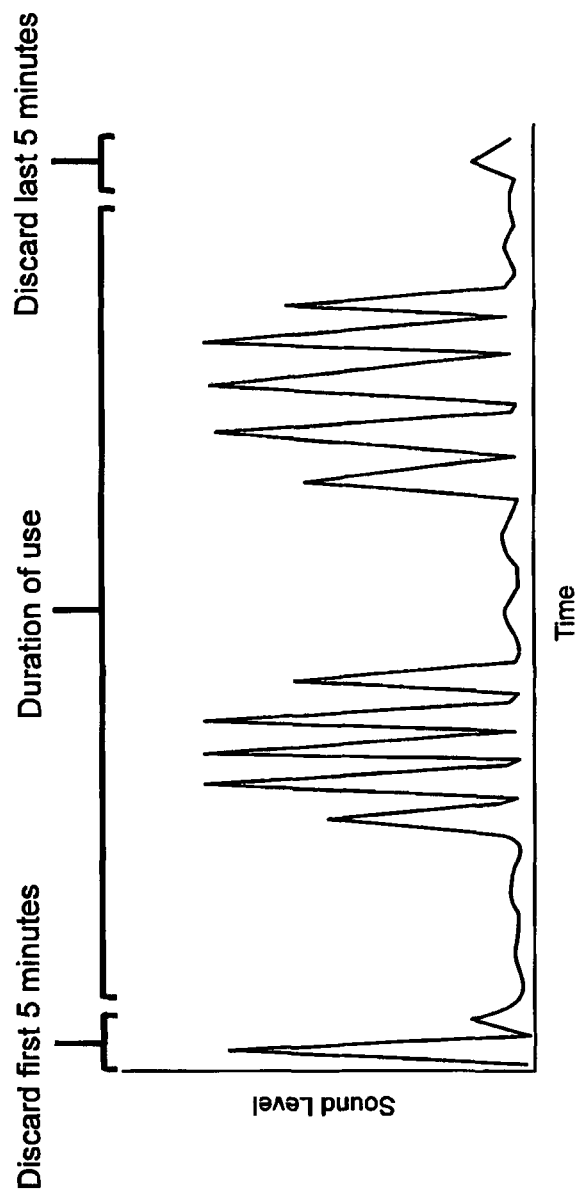
Figure 202:
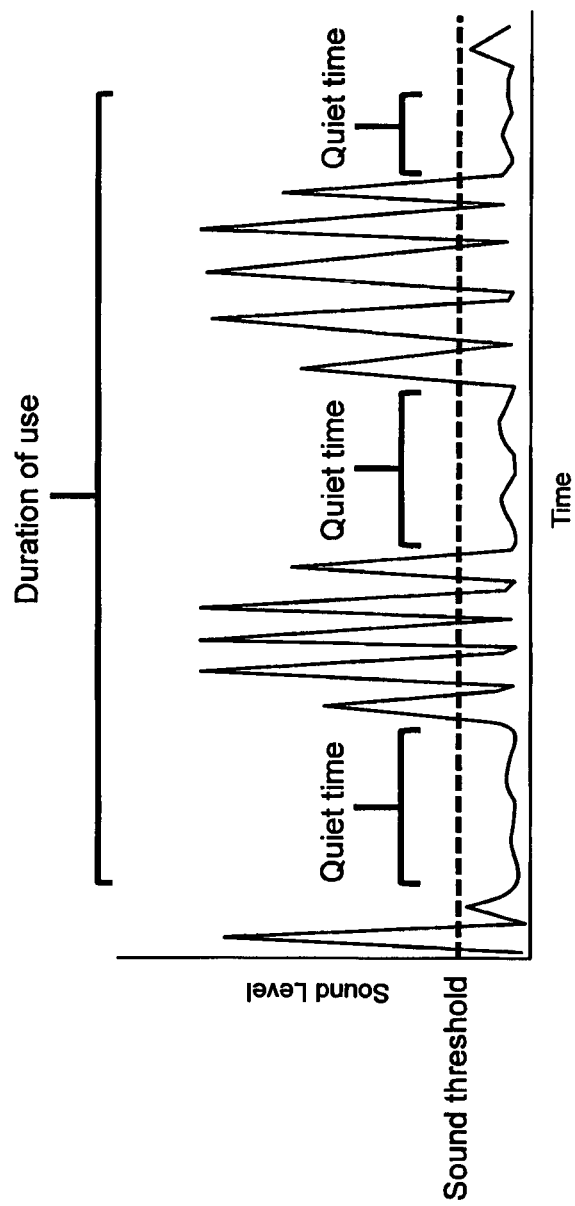

In an example, the result may be a quiet evaluation result equal to the ratio of noise-free duration over the duration of use. That is, the quiet evaluation result provides a percentage of the night that the user was quiet, i.e., a percentage of no snoring. As shown in FIG. 201, the duration of use is the total usage time of the system and may be measured from the time the system is powered on to when the system is powered off. Leading and trailing minutes of the usage time (e.g., first five minutes and last five minutes) may be discarded to remove sound that may not be snoring. As shown in FIG. 202, the noise-free duration or total quiet time is the total time that the sound level is below a certain predetermined sound threshold within the duration of use. Pauses between consecutive snores should not be counted as "quiet time."

In an example, the quiet evaluation result may require a specified duration of usage (e.g., 1 hour, 2 hours, or more), e.g., to avoid showing results that could be inaccurate due to lack of time/sound data. Also, in an example, the quiet evaluation result may reset after a specified duration of non-use (e.g., resets after 3, 4, 5, or more hours of non-use). For example, if the user does not use the system for 3 hours, a new quiet evaluation result is computed the next time the system is turned on to ensure that the user is provided with a new result for each nap/sleep. If the user turns off the system and then turns it back on within 3 hours, the new session is aggregated with the previous one to allow the result to reflect an entire night's usage, even when the user turns the system on/off continuously during the night (e.g., bathroom break, etc.).

This information may be useful in determining whether the current PAP system is appropriate for the patient or whether to adjust treatment, e.g., raise or lower pressure, and/or consult a physician or dentist for different treatment, e.g., different PAP system, CPAP system providing more pressure, mandibular advancement device, etc.

The display of the PAP system may provide feedback to the patient to enhance user engagement, e.g., result or analysis may provide positive feedback to the patient that current treatment is effective, display simply acknowledges successful night of treatment, display acknowledges a percentage of time that room was quiet (i.e., percentage of no snoring), etc., to help encourage the patient to make use of the device and to better acclimate the patient in the event more comprehensive/upgraded therapy is required.

As noted above, the microphone may be provided to the PCB within the housing. Alternatively, the microphone may be mounted on another part of the blower or on the patient interface, e.g., in the air path. Another alternative is to provide the microphone as a separate stand-alone device that may be positioned adjacent the patient and/or in communication with the blower, patient interface.

11. Display

Figure 140:
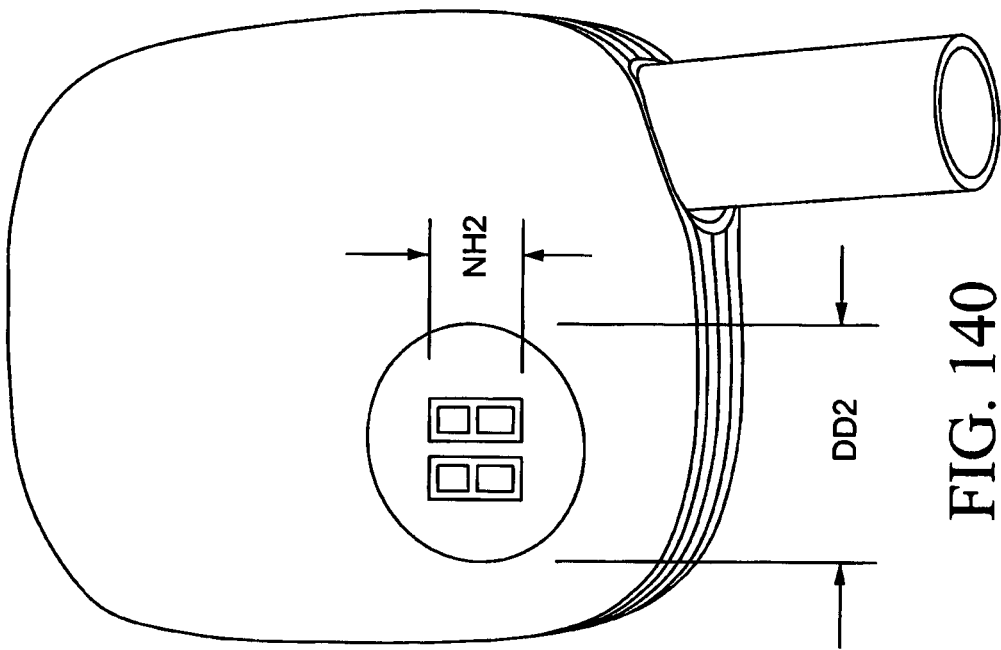
FIGS. 139 and 140 show a PAP device including alternative display sizes according to alternative examples of the present technology.
Figure 139:
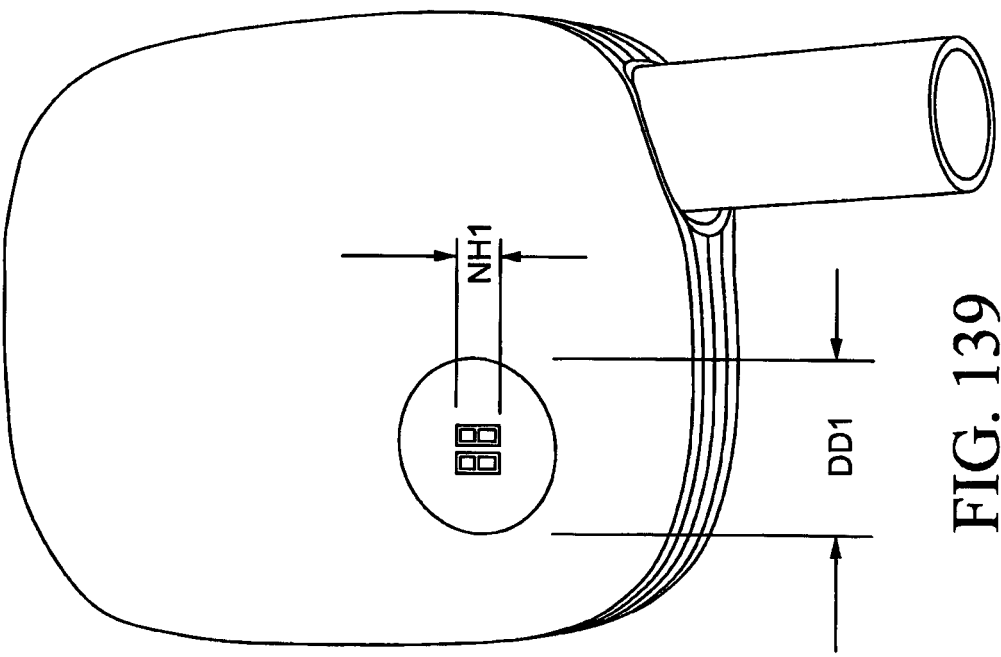
Figure 143:
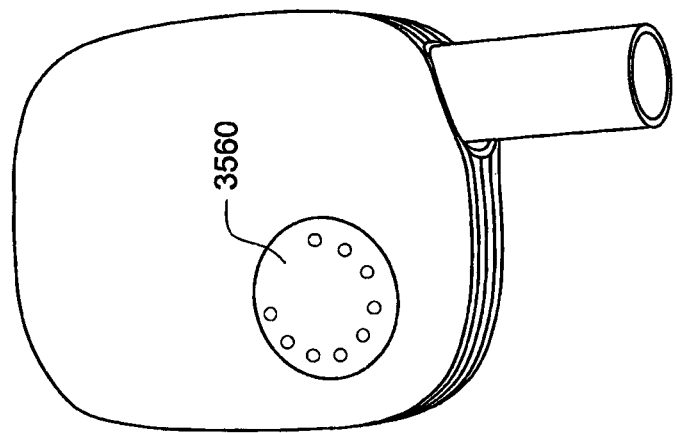
FIG. 143 shows a PAP device with a non-numeric display including a pie chart according to an example of the present technology.
Figures 2, 142:
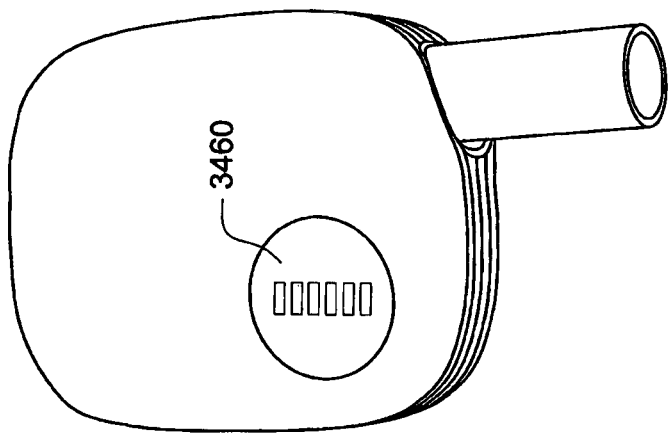
Figures 1, 142:
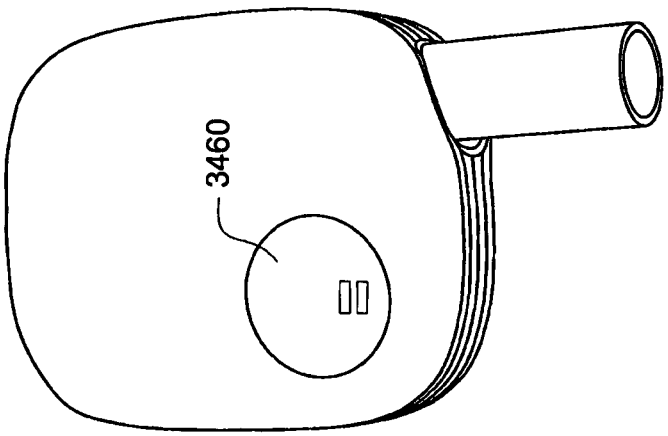
Figure 144:
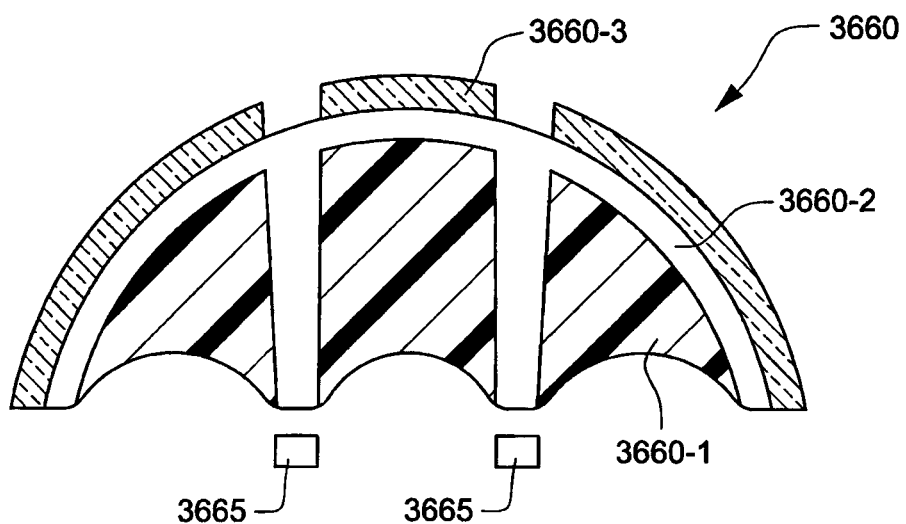
FIG. 144 shows a display including a black resin layer, a clear resin layer, and an IMD layer according to an example of the present technology.

In an example, the display or user interface of the PAP system may be relative simple, e.g., on/off button, series of different colored lights (e.g., LEDs). For example, the display may simply include one or more lights to provide patient feedback. For example, FIGS. 142-1 and 142-2 show a non-numeric display 3460 including a bar graph to indicate results. FIG. 143 shows a non-numeric display 3560 including a circular chart with segments to indicate results, e.g., greater proportion or number of segments may suggest that user should adjust degree of pressurized air or simply suggest seeing a doctor. In one example, the display may include a single light that changes color/intensity (e.g., red, green, yellow) based on pressure, breathing pattern, etc. For example, FIGS. 141-1 to 141-3 show a non-numeric display 3360 configured to change color/intensity (e.g., red, green, yellow). In an example, color/intensity may be used to indicate sleep quality, e.g., green (good), yellow (ok, but could be better), red (not good—see doctor). In another example, the display may include a light that changes color based on whether power is on or off. In another example, the display may include a light indicating an operating mode and/or an error. It should be appreciated that the button or display may be provided at any suitable location, e.g., depending on desired aesthetic, electrical components, etc. In an example, the LED display may include an in-mold-decoration (IMD) housing which creates a pathway for the light for keeping lines crisp against the fabric cover in use. For example, FIG. 144 shows a display 3660 including a black resin layer 3660-1, a clear resin layer 3660-2, and an IMD layer 3660-3 structured to provide a pathway for LEDs 3665 to shine therethrough. In an example, the size of the button may be increased to increase the available space for a display and hence increase the numerical height of the numerical display in use, e.g., display diameter may be in the range of about 20-40 mm (e.g., display diameter DD1 about 27 mm in FIG. 139 and display diameter DD2 about 37 mm in FIG. 140) with a numerical height in the range of about 5-15 mm (e.g., numerical height NH1 about 7 mm in FIG. 139 and numerical height NH2 about 14 mm in FIG. 140).

In an example, the display or user interface is structured to assure proper usage of the system (e.g., alerting user when a failure occurs (e.g., improper seal, blocked airflow), alerting user when system is used correctly), enhance trust (e.g., accessible and understandable user interface will provide user with confidence in using the system), and/or provide proper feedback (providing user with feedback that system is helping will ensure continued usage).

Figures 129, 130:
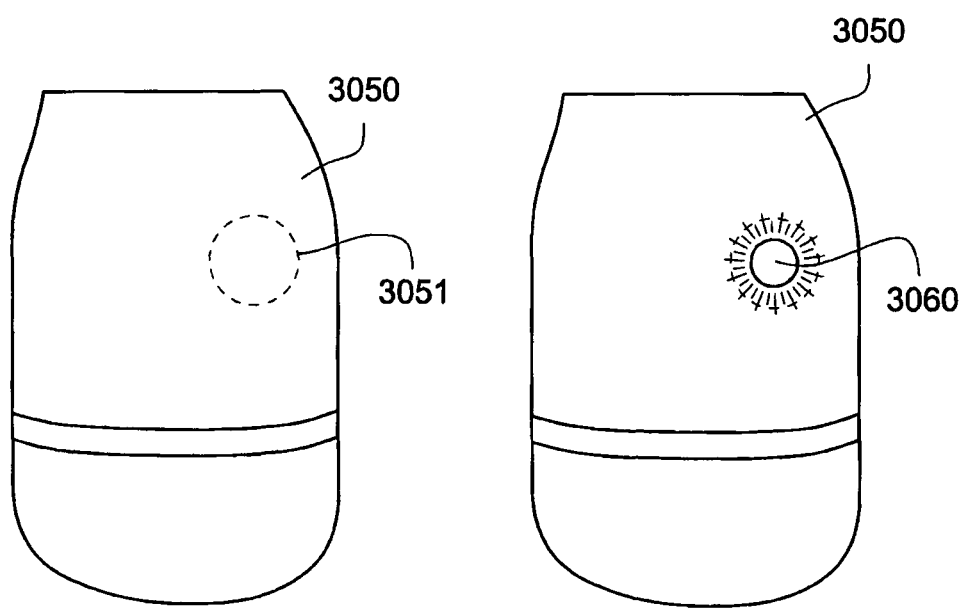
FIGS. 129 and 130 show a PAP system including a user interface according to an example of the present technology.

The user interface may include alternative configurations to indicate status of the system. For example, FIGS. 129 and 130 illustrate an example of a user interface, i.e., an on/off button, including a bi-color (e.g., red, blue) LED 3060 to indicate status of the device. The fabric cover or wrap 3050 of the system which encloses the PAP device and the on/off button includes stitching 3051 to indicate where the button is located. The cover may also include a recessed portion adapted to align with the button to help locate the button's position. In use, the user may locate the button by feeling for the recessed portion and/or by locating it visually from the stitching. The button may be depressed to turn the system on/off. In an example, one color of the LED 3060 (e.g., a blue light) may indicate that the device is working correctly, and another color of the LED 3060 (e.g., a red light) may provide a warning that something is wrong with the device or that the device is not being used properly, e.g., blower overheated (e.g., blocked airflow) or had to shut down for any other reason (such as improper nose seal).

In another example, as shown in FIGS. 131-134, the user interface, i.e., an on/off button, includes a tri-color (e.g., red, blue, and yellow) light ring 3160 to guide the user and indicate status of the device. As noted above, the fabric cover 3150 may include stitching 3151, and/or a recessed portion to indicate where the button is located.

In use, as shown in FIG. 132, the light ring 3160 glows in a full circle when the device is turned on to indicate that the device is starting up. As the user breaths through the nose piece, the brightness of the light ring changes, e.g., light ring includes pulse-width modulation or similar to vary light intensity. For example, when the user exhales, the ring 3160 becomes brighter (e.g., see FIG. 133) and when the user inhales, it dims (e.g., see FIG. 134). The system shows awareness by pulsing the light ring in the same rhythm as the user's breathing, which increase the user's trust in the device.

In an example first time use, the user may put on the patient interface and feel unsure of what to do., e.g., the user feels air coming through the patient interface but is intimidated by the sensation. The system may detect that airflow is not being sent properly and the light ring turns to yellow, e.g., user isn't breathing or nozzle arrangement is off/blocked. The user sees this and knows that they are doing something wrong. As the user starts breathing, the light turns to blue and pulses with their breathing, indicating to the user that they are using the device correctly. The user proceeds to go to sleep. In the middle of the night, a pillow covers the blower which prevents it from drawing enough air. The light ring turns to red, indicating that airflow was blocked. The user wakes up in the morning and notices that system is off. The user checks the device and sees the red light, thereby indicating that the airflow was blocked, blower overheated, or system shut down so the can adjust its placement the next night. Such light ring arrangement guides the user and assures proper usage by indicating correct usage and errors with the light ring.

In another example, as shown in FIGS. 135-138, the user interface, i.e., an on/off button, includes a numeric display 3260 configured to display a result that tells the user the percentage of the night that was quiet, i.e., percentage of no snoring. As noted above, the fabric cover 3250 may include stitching 3251 and/or a recessed portion to indicate where the button is located. In an example, the user may depress and hold the button to turn the system on/off. In an example, the user may double-click the button to show the previous result, whether the system is on/off.

Figure 135:
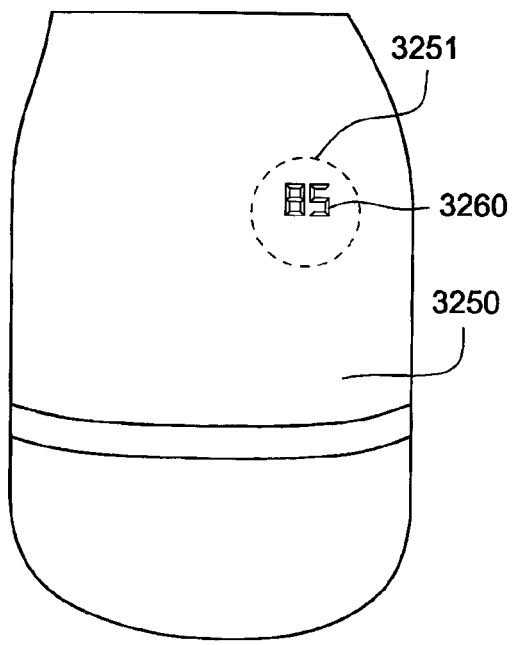
FIGS. 135 to 138 show a PAP system including a user interface according to another example of the present technology.
Figure 136:
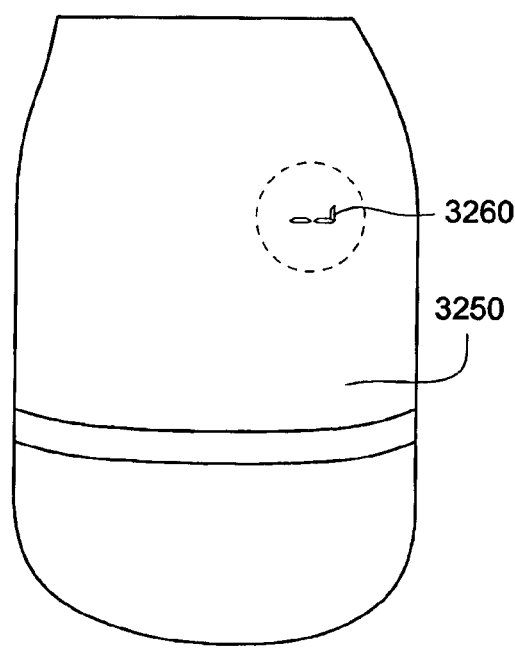
Figure 137:
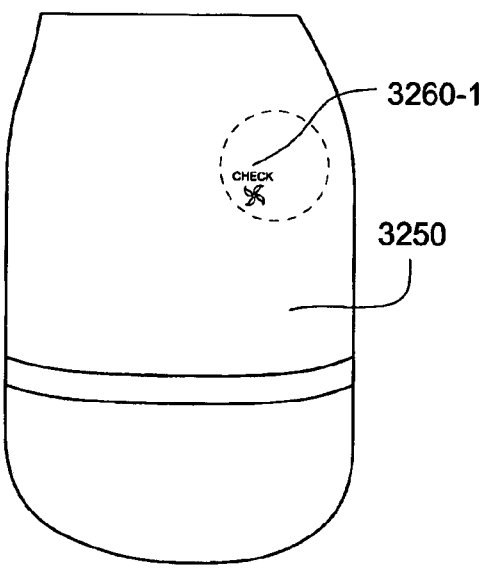
Figure 138:
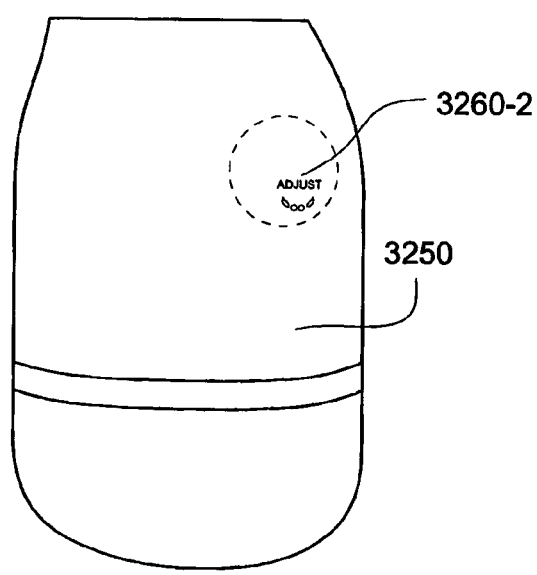

In an example use, the user turns on the system, puts on the patient interface, and proceeds to go to sleep. As shown FIG. 136, the display 3260 shows a little animation, e.g., animation of a completing circle, indicating that the device is starting up. When the user wakes up, the user wonders if they snored or not. The user can check the evaluation result which tells the user a noise-free percentage, e.g., user was quiet (snore-free) 85% of the night as shown in FIG. 135. Another use may indicate consistently low results, and the user's partner may complain about snoring. This tells the user that they may have a possible medical issue and the user decides to consult a doctor. As shown in FIG. 137, a warning, e.g., check fan display 3260-1, may be displayed when the system is not properly operating, e.g., blower cannot draw air properly (e.g., intake covered and the blower overheats). As shown in FIG. 138, another warning, e.g., adjust seal display 3260-2, may be displayed when the user needs to adjust the patient interface (e.g., nozzle arrangement), e.g., improper seal detected. As shown in FIGS. 137 and 138, the display may include backlit icons for warning. The system may include a microphone for noise detection, a timer for quiet time and usage, and sensor for measuring RPM of the blower to detect irregular airflow.

12. Alternative Inlet/Filter Arrangements

Figures 1, 145:
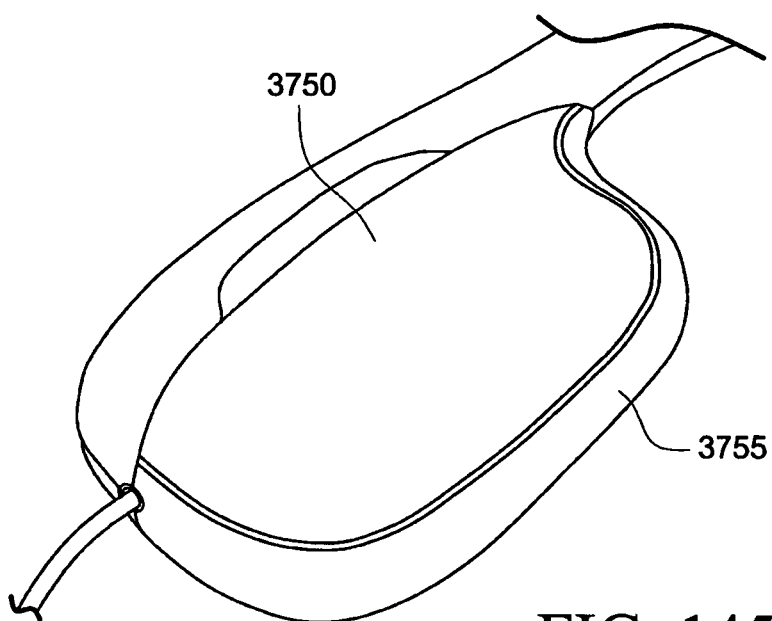
Figures 2, 145:
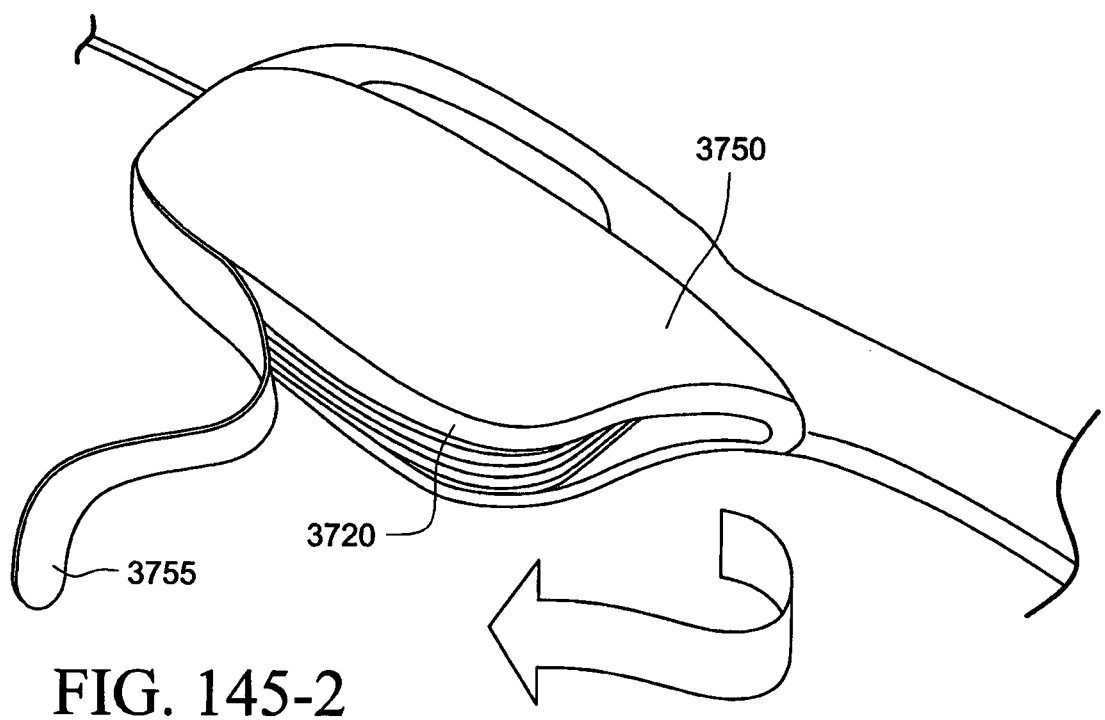
Figures 3, 145:
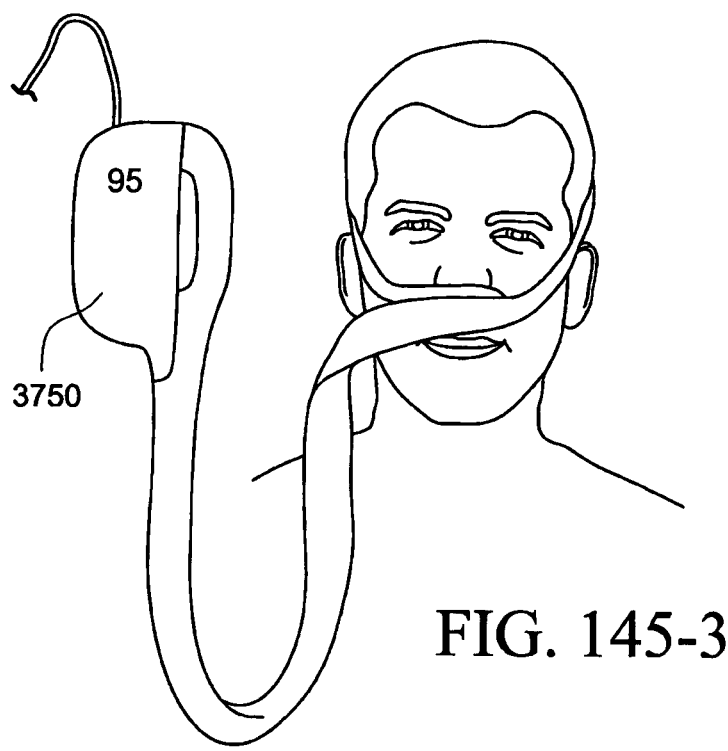

The portion of the cover along the intake opening or air inlet of the PAP device may include alternative arrangements. For example, FIGS. 145-1 to 145-3 shows a cover 3750 including an elongated fabric filter 3755 arranged to extend along at least the air inlet of the PAP device 3720. The fabric filter provides part of the exterior cover so it is easily accessible and easily visible to determine cleaning/replacement. In an example, the fabric filter may be removably attached to the remainder of the cover, e.g., by a hook and loop arrangement. However, the fabric filter may be attached in other suitable manners, e.g., adhesive. In an example, the filter may be arranged to maintain the remainder of the cover in position on the PAP device, e.g., filter structured to engage and enclose open end of cover.

Figures 1, 146:
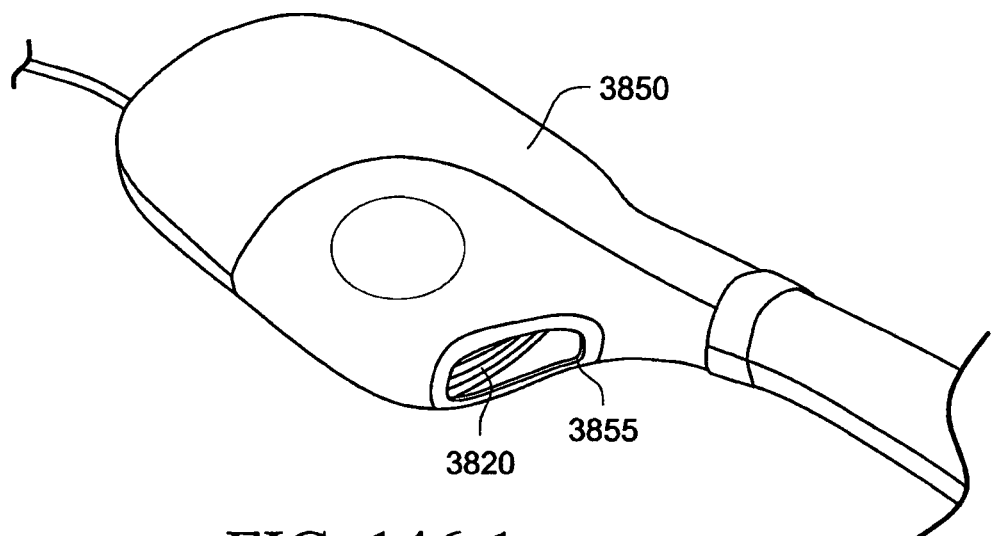
Figures 2, 146:
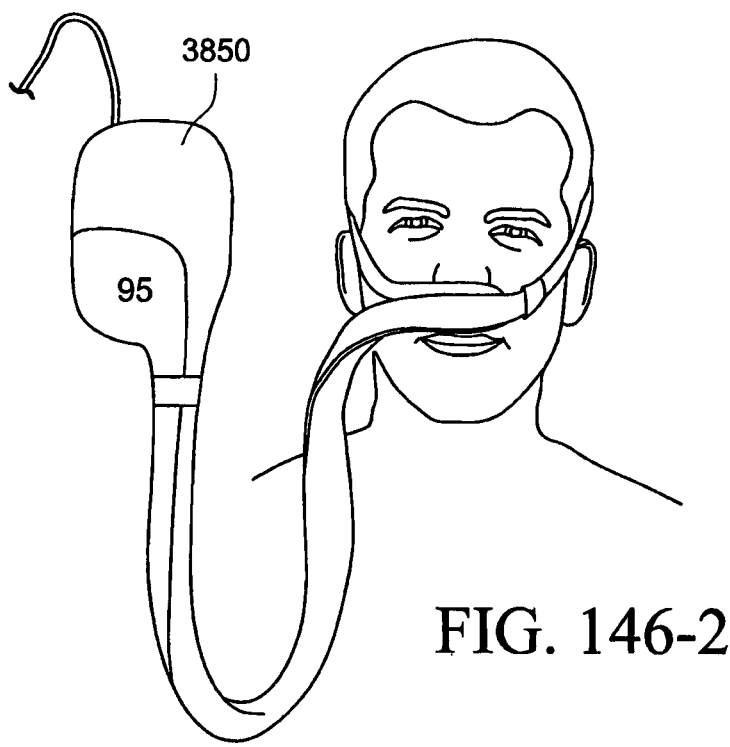

FIGS. 146-1 to 146-2 show a cover 3850 including open hole 3855 adjacent the air inlet of the PAP device 3820. Such arrangement does not restrict the air inlet and removes the likelihood of any problems with air path biocompatibility.

Figures 1, 147:
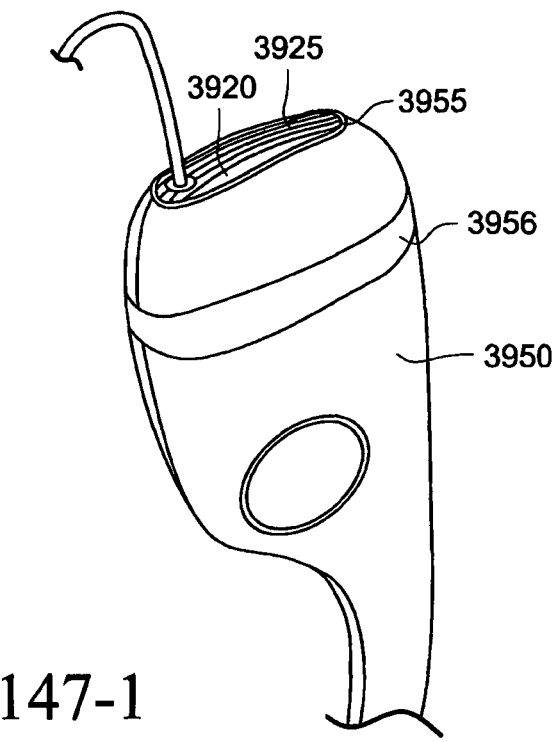
Figures 2, 147:
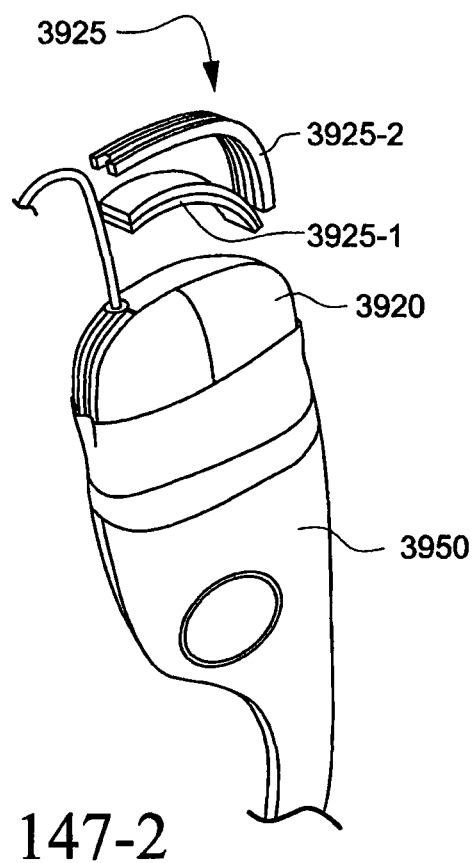
Figures 3, 147:
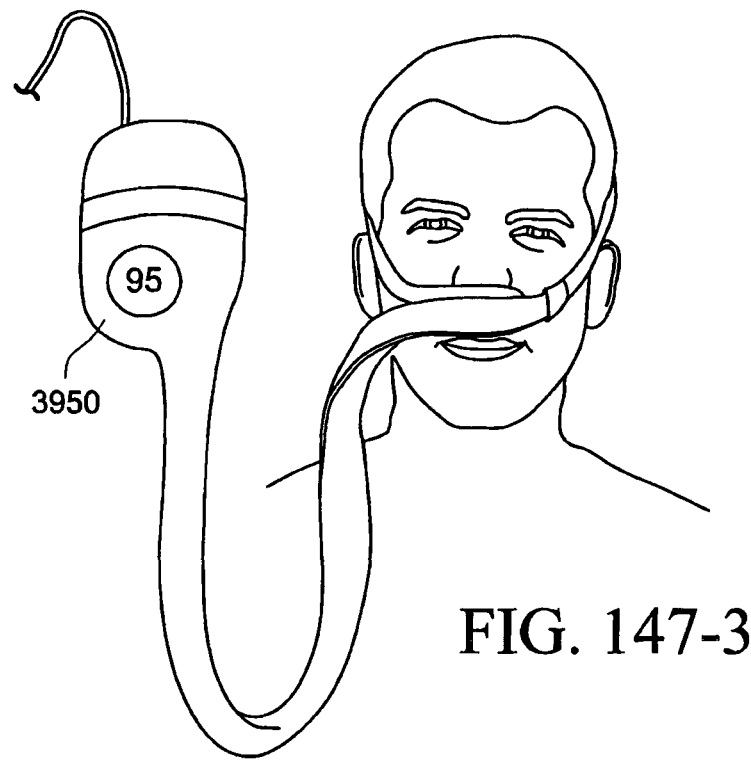
Figures 1, 152:
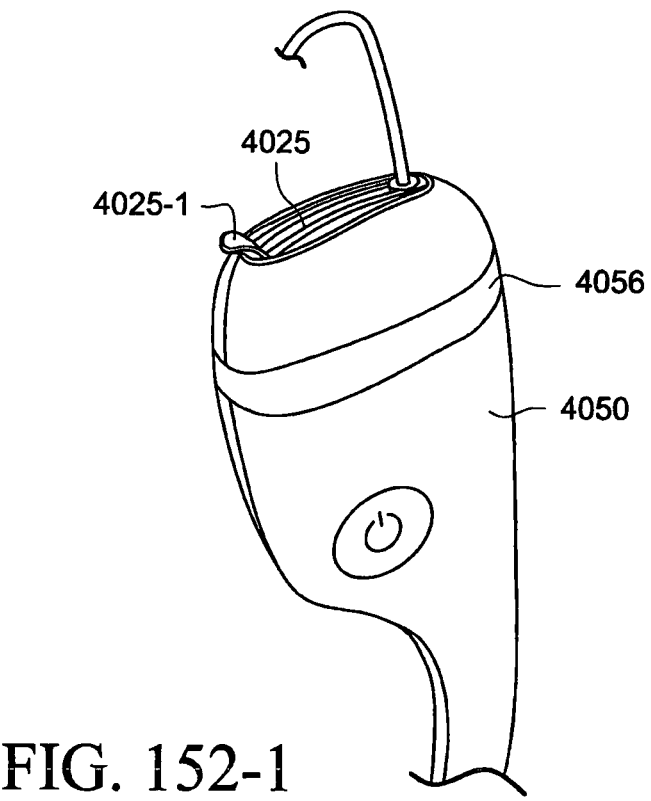
Figures 2, 152:
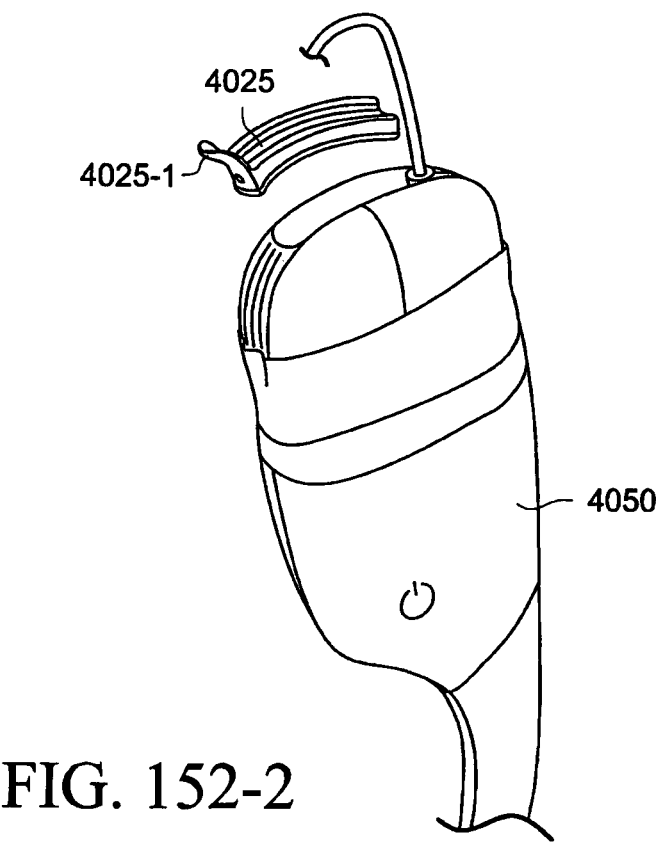
Figures 3, 152:
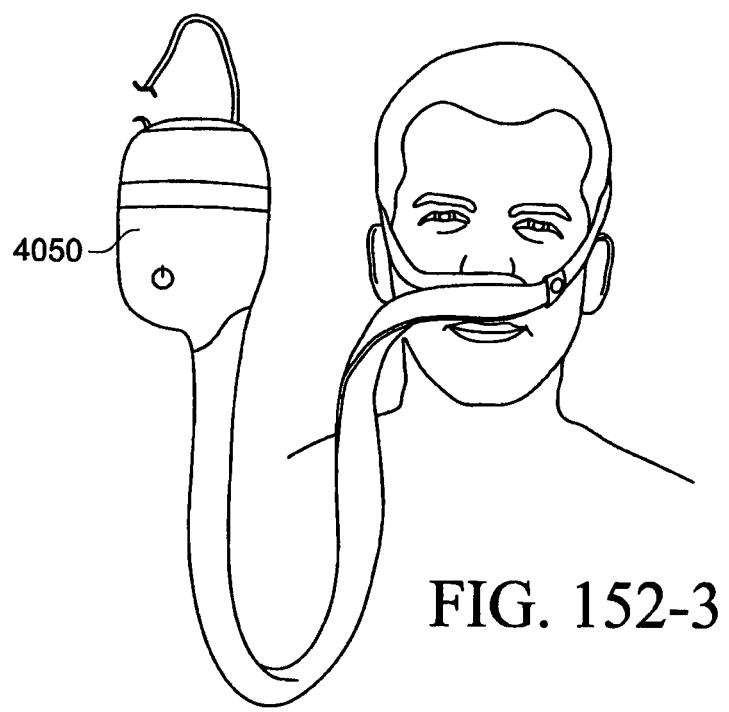

FIGS. 147-1 to 147-3 show a cover 3950 with an open bottom 3955 adapted to expose a filter arrangement 3925 provided to the PAP device 3920. As illustrated, the filter arrangement 3925 includes a filter 3925-1 and a door structure 3925-2 to retain the filter to the PAP device. The bottom of the cover adjacent the open bottom includes an elastic band 3956 that allows the cover to be pulled back from the filter arrangement for easy access and cleaning/replacement. The open bottom allows the filter arrangement to easily accessible and easily visible to determine cleaning/replacement. Also, the open bottom provides an unrestricted air path so biocompatibility and restricted inlet are low risk. FIGS. 152-1 to 152-3 show another example a cover 4050 with an elastic band 4056 adjacent the open bottom to facilitate access of the filter arrangement 4025. In this example, the filter arrangement 4025 includes a one-piece removable filter with a pull-tab 4025-1 to facilitate removal.

Figures 1, 153:
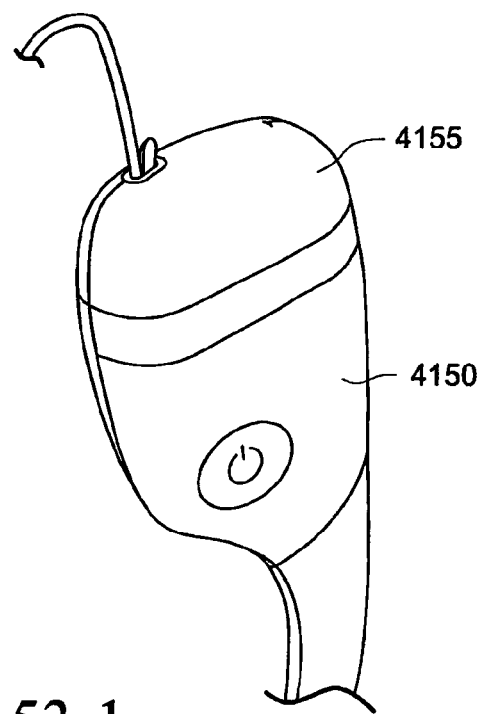
Figures 2, 153:
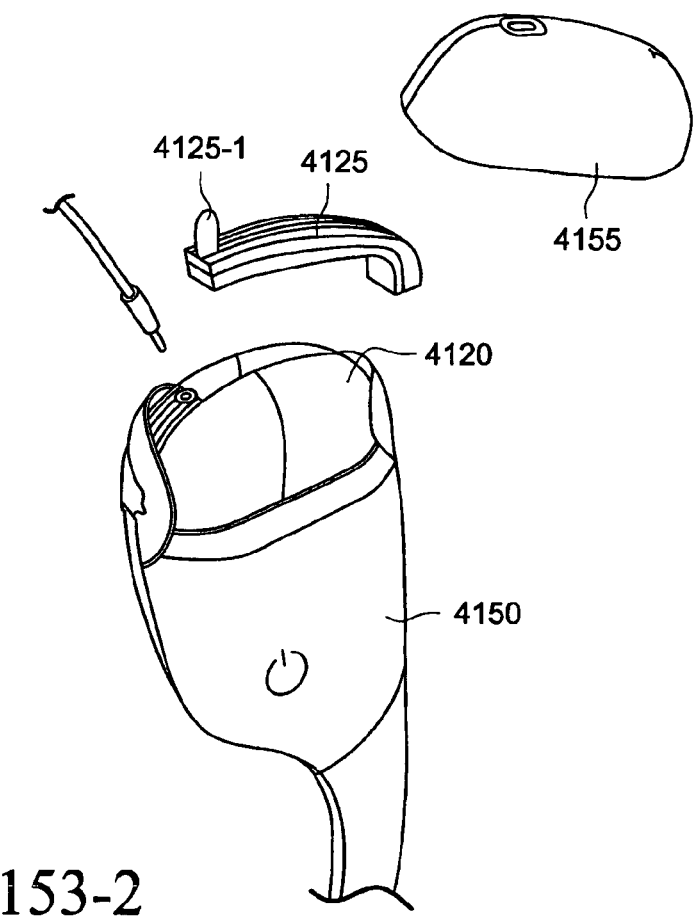
Figures 3, 153:
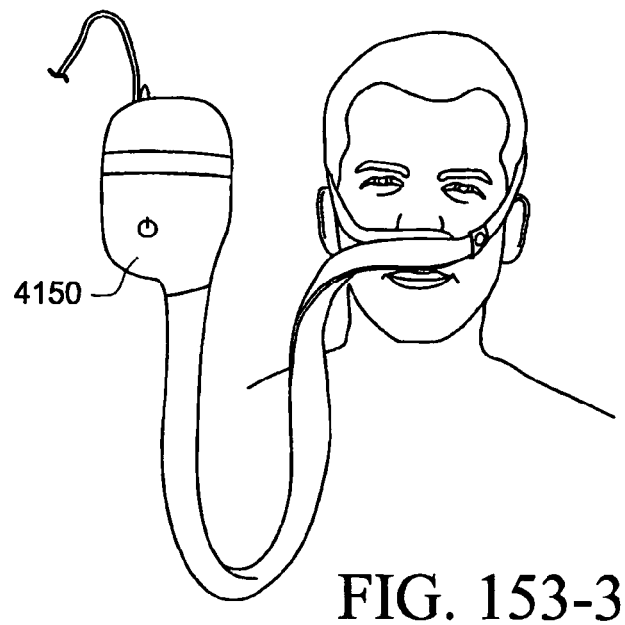

FIGS. 153-1 to 153-3 show a cover 4150 with a removable pillow slip 4155 adapted to expose a filter arrangement 4125 provided to the PAP device 4120. As illustrated, the filter arrangement includes a one-piece removable filter with a pull-tab 4125-1 to facilitate removal.

Figures 1, 155:
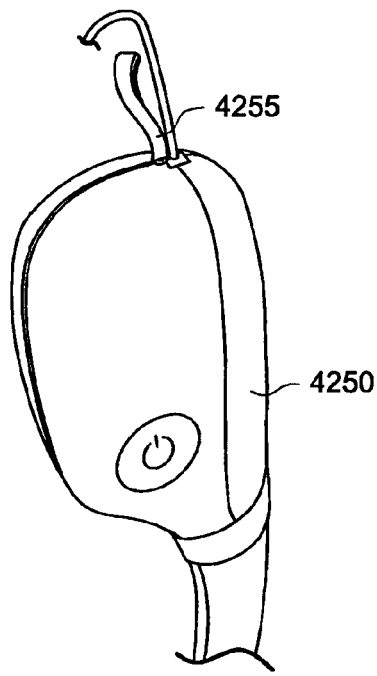
Figures 2, 155:
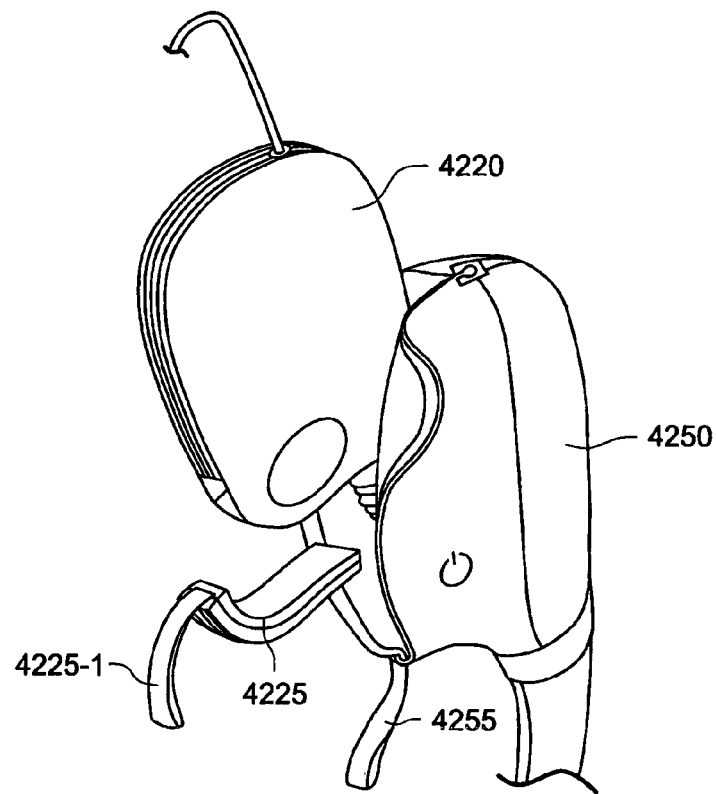
Figures 3, 155:
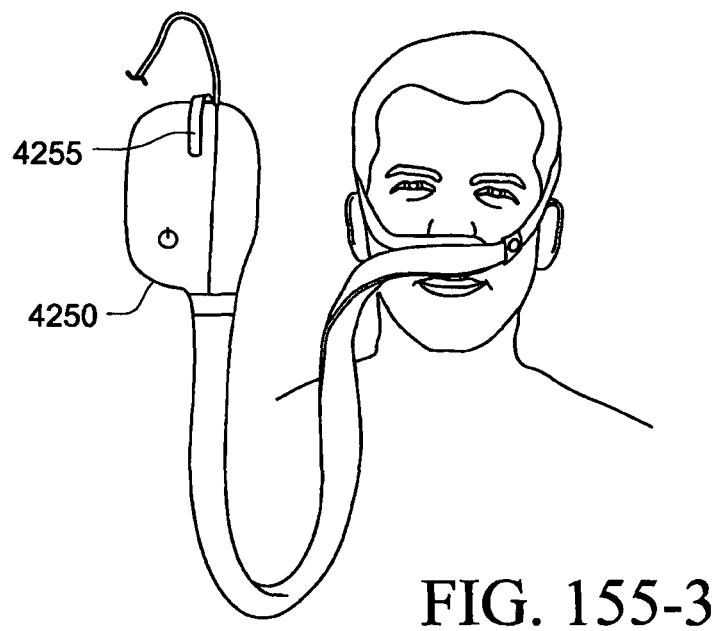

FIGS. 155-1 to 155-3 show a cover 4250 with a single zipper 4255 along the pouch portion thereof to access the PAP device 4220 and its filter arrangement 4225. As illustrated, the filter arrangement 4225 includes a one-piece removable filter with a pull-tab 4225-1 to facilitate removal.

13. Exemplary Cover Manufacturing Techniques

Figure 149:
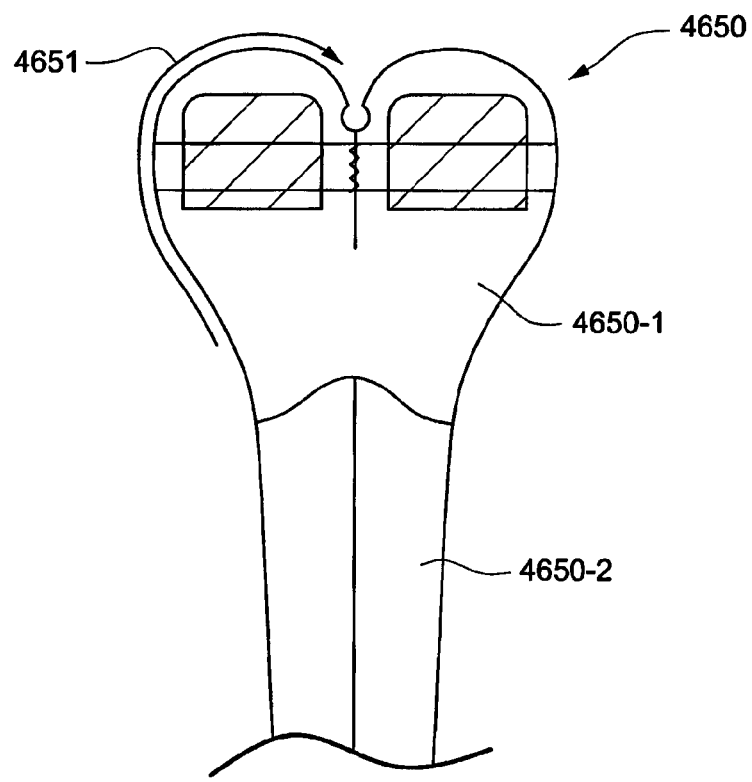
FIG. 149 is a schematic view showing an exemplary technique for manufacturing a cover according to an example of the present technology.

In an example, as shown in FIG. 149, the cover 4650 may include a single piece of textile material that is folded over and attached along its length by a single seam to form the pouch portion 4650-1 and tube portion 4650-2 of the cover. In an example, the pouch portion and tube portion may be provided as separate pieces of textile material that attached to one another, e.g., overlapped and attached by seam tape or attached by stitching.

Figure 150:
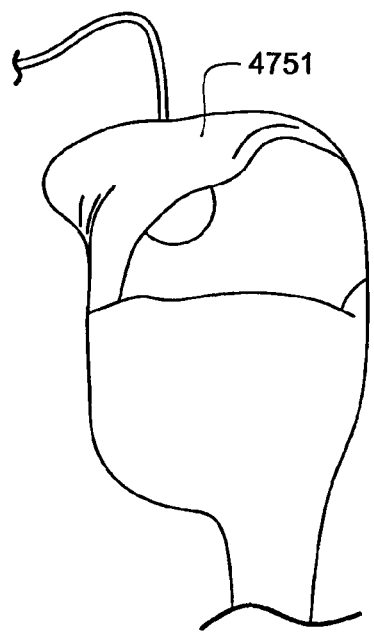
FIG. 150 shows a PAP system with a cover according to an example of the present technology.
Figure 151:
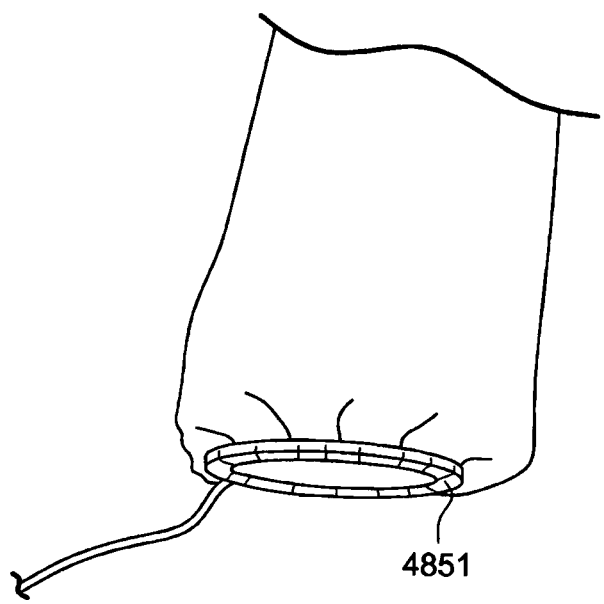
FIG. 151 shows a PAP system with a cover according to an example of the present technology.

A zipper 4651 (e.g., single direction zip) is provided along an end of the pouch portion (e.g., bound with heat melt TPU film) to releasably close the end. However, the end of the pouch portion may be opened/closed in other suitable manners, e.g., elastic band 3956 (e.g., FIGS. 147-1 to 147-3), pillow slip 4751 provided to end of cover (e.g., FIG. 150), or drawstring 4851 provided to end of cover (e.g., FIG. 151).

In other examples, the cover may be manufactured using a single piece of textile material that is folded over and attached along its length by, e.g., seam tape (e.g., which may include texturized portions, piping detail, etc.), an ultrasonic roller (e.g., which provides a seamless edge for reduced bulk), or circular knit.

Figures 1, 2, 154:
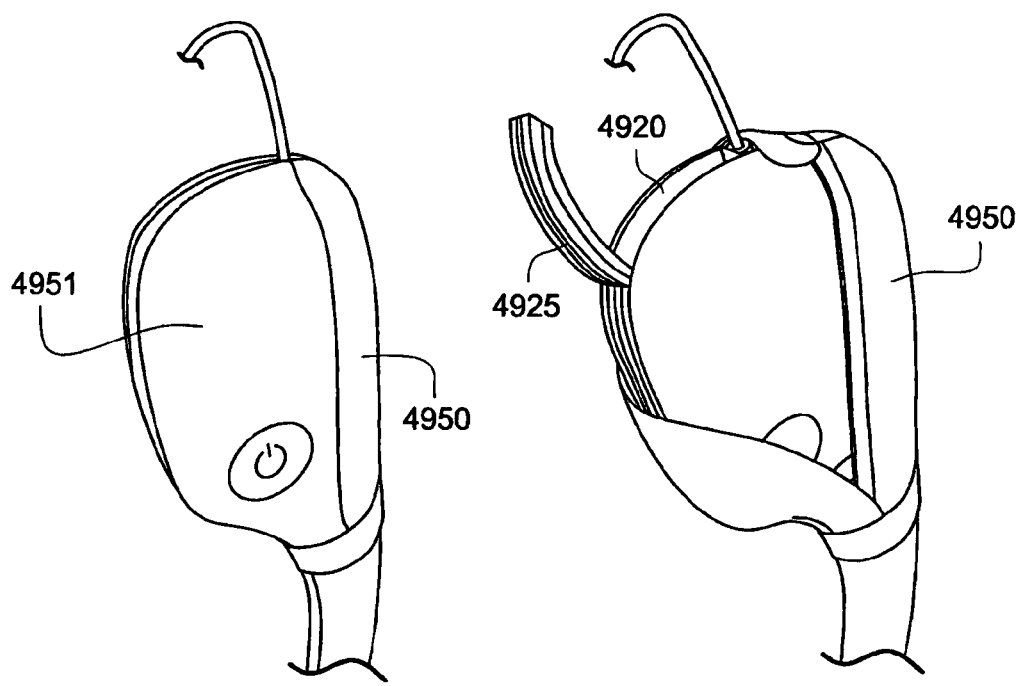
Figures 3, 154:
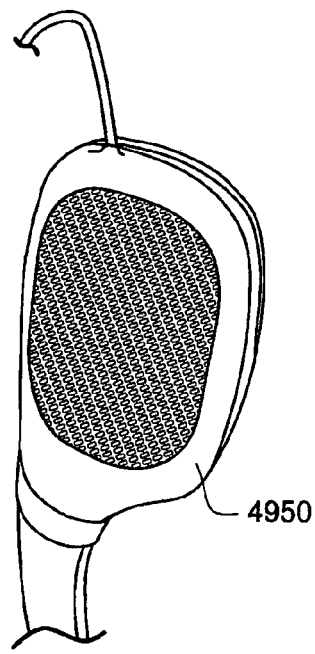

In an example, the cover may constructed of a textile material that is disposable, bio-compatible for skin and airway, changes color over time (e.g., over the course of 1-3 months), changes color based on air exposure and/or not UV activated. FIGS. 154-1 to 154-3 show another example of a cover 4950 with a removable pillow slip 4951 adapted to expose a filter arrangement 4925 provided to the PAP device 4920.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A PAP system, comprising:
a PAP device to generate a supply of pressurized air;
a patient interface adapted to form a seal with a patient's face;
air delivery tubing to interconnect the patient interface and the PAP device; and
a cover that substantially encloses at least a portion of the PAP device and a portion of the air delivery tubing,
wherein the cover includes a wrap or scarf-like arrangement including a headgear strap portion that cooperates with another headgear strap adapted to wrap entirely around a patient's head to stabilize and support the system on the patient's head,
wherein the PAP device is supported within the cover such that the PAP device is suspendible from the patient's head by the air delivery tubing, and
wherein the cover includes a tube portion to substantially enclose one or more portions of the air delivery tubing and a pouch portion to substantially enclose one or more portions of the PAP device, and at least a portion of the pouch portion comprises a diffuse material structured and arranged to allow air therethrough to an air inlet of the PAP device to allow operation of the PAP device when enclosed by the pouch portion.

2. The PAP system according to claim 1, wherein the cover substantially encloses one or more portions of the patient interface.

3. The PAP system according to claim 1, wherein the PAP device generates a supply of pressurized air in the range of about 2-30 cm $H_2O$.

4. The PAP system according to claim 1, wherein the patient interface includes a nozzle, nasal prong, pillow, cradle or cushion arrangement.

5. The PAP system according to claim 1, wherein the air delivery tubing includes a non-cylindrical cross-sectional shape structured such that the air delivery tubing may move between a first open phase and a second at least partially collapsed phase.

6. The PAP system according to claim 1, wherein the cover is constructed of a textile material.

7. The PAP system according to claim 1, wherein the patient interface, air delivery tubing, cover, and/or headgear strap is constructed of materials including different colors, patterns, and/or surface texture so as to blend in with the patient's skin and/or hair.

8. The PAP system according to claim 1, wherein the cover is structured to hide, veil or conceal one or more connection points between the PAP device, patient interface, and air delivery tubing.

9. The PAP system according to claim 1, wherein the PAP device is adapted to be located over the patient's shoulder when the patient is in an upright position and/or adapted to be located beside, near or adjacent the patient when the patient is in a supine position.

10. The PAP system according to claim 9, wherein the PAP device is adapted to be located near the patient's chest when the patient is in the supine position.

11. The PAP system according to claim 1, wherein the system is portable and lightweight to allow the patient to freely move around while wearing the system.

12. The PAP system according to claim 1, wherein the headgear strap portion and the headgear strap are structured to overlap by the patient's nose.

13. The PAP system according to claim 12, wherein the headgear strap portion and the headgear strap are connected to one another at the overlap.

14. The PAP system according to claim 1, wherein the PAP device is adapted to be positioned relatively close to the patient's nose to provide the air delivery tubing with a reduced tube diameter.

15. The PAP system according to claim 14, wherein the PAP device is adapted to be positioned about 50 cm to 80 cm from the patient's nose resulting in the air delivery tubing having a tube diameter of about 10 mm to 20 mm.

16. The PAP system according to claim 1, wherein the system is reversible which allows the air delivery tubing to extend from either side of the patient interface.

17. The PAP system according to claim 1, wherein the system is configured to wrap across to either the left side or the right side of the patient's body or face.

18. The PAP system according to claim 1, wherein the system defines a loop adapted to pass generally along an underside of the patient's nose, along the cheek regions, above the ears, and over the crown and parietal portion of the patient's head.

19. The PAP system according to claim 1, wherein the headgear strap portion is adapted to wrap along the cheek region, above the ear, and around the back of the patient's head, and connect to an intermediate portion of the headgear strap so as to define a back strap for supporting the system.

20. The PAP system according to claim 1, wherein the headgear strap is adapted to wrap under the patient's nose, along the cheek region, above the ear, and over the crown of the patient's head, and connect to an intermediate portion of the headgear strap portion to as to define a crown strap for supporting the system.

21. The PAP system according to claim 1, wherein at least a portion of the PAP device extends out of the cover to allow access to one or more controls provided to the PAP device.

22. The PAP system according to claim 1, wherein the headgear strap portion and the headgear strap are structured to overlap by the patient's nose, the headgear strap portion and the headgear strap are connected to one another at the overlap by a connector, and the connector provides a vent from the patient interface.

23. The PAP system according to claim 22, wherein the connector comprises a button.

24. The PAP system according to claim 1, wherein the diffuse material of the pouch portion allows the air inlet of the PAP device to communicate with atmosphere.

25. The PAP system according to claim 24, wherein the cover is structured and arranged to create a gap adjacent the air inlet of the PAP device to prevent occlusion of the air inlet of the PAP device in use.

26. The PAP system according to claim 1, wherein the diffuse material of the pouch portion covers the air inlet and allows air to pass through a thickness of the pouch portion to the air inlet of the PAP device.

27. The PAP system according to claim 1, wherein said portion of the pouch portion comprises an opening adjacent the air inlet of the PAP device.

28. A system for delivery of pressurized air to a patient for therapy, the system comprising:
   a base unit including a blower configured to generate a supply of air at positive pressure;
   a patient interface adapted to be provided to a patient's face;
   a tube to deliver the supply of air at positive pressure from the base unit to the patient interface; and
   a controller configured to monitor and automatically control adjustment of the system so that the patient interface is automatically positioned optimally for the patient for therapy,
   wherein the controller is configured to (1) receive one or more of data from a force sensor, data regarding the positioning of the tube, data regarding the patient's sleeping position, and data regarding the patient's breathing patterns in order to analyse the patient's activity and positioning, and based on said data, (2) automatically modify a shape of the tube in order to move the patient interface to achieve satisfactory seal and comfort for optimal treatment, and wherein the system is adapted to adjust the total force applied to the patient's face by the patient interface in response to leak or patient discomfort.

29. The system according to claim 28, further comprising an interface controller structured to adjust an angle of interface between the patient interface and the patient's face in response to leak or patient discomfort.

30. The system according to claim 28, wherein the patient interface is adapted to engage the patient's face.

31. The system according to claim 28, wherein the patient interface is adapted to be positioned adjacent to the patient's face.

32. The system according to claim 28, wherein the system is adapted to fit itself to the patient while the patient is unaware or asleep.

33. The system according to claim 28, wherein the system is adapted to provide a minimum required force to achieve satisfactory seal and comfort by adapting force and force angle provided by the patient interface in real time.

34. The system according to claim 28, wherein the tube includes a series of active elements along its length, each of the active elements structured to selectively contract and/or extend to adjust a length of the tube.

35. The system according to claim 28, further comprising a force sensor to measure force and torque between the patient interface and the patient's face.

36. The system according to claim 28, wherein the tube includes one or more sensors configured to sense movement of the patient and an adjustment device configured to automatically adjust the position of the tube to compliment the patient's position.

37. The system according to claim 28, further comprising one or more magnets or electromagnets arranged to allow the tube to follow movements of the patient.

38. The system according to claim 28, wherein the tube is structured to provide a force to the patient interface to seal the patient interface onto the patient's face without the use of headgear.

39. The system according to claim 28, wherein the system is adapted to adjust the force angle applied to the patient's face by the patient interface in response to leak or patient discomfort.

* * * * *